United States Patent
Elmén et al.

(10) Patent No.: US 9,133,455 B2
(45) Date of Patent: Sep. 15, 2015

(54) PHARMACEUTICAL COMPOSITION COMPRISING ANTI-MIRNA ANTISENSE OLIGONUCLEOTIDES

(71) Applicant: Santaris Pharma A/S, Hørsholm (DK)

(72) Inventors: Joacim Elmén, Malmö (SE); Phil Kearney, Picton (AU); Sakari Kauppinen, Smørum (DK)

(73) Assignee: Roche Innovation Center Copenhagen A/S, Horsholm (DE)

( * ) Notice: Subject to any disclaimer, the term of this patent is extended or adjusted under 35 U.S.C. 154(b) by 0 days.

(21) Appl. No.: 14/245,557

(22) Filed: Apr. 4, 2014

(65) Prior Publication Data

US 2014/0329883 A1 Nov. 6, 2014

Related U.S. Application Data

(63) Continuation of application No. 13/415,685, filed on Mar. 8, 2012, now Pat. No. 8,729,250, which is a continuation of application No. 12/295,960, filed as application No. PCT/DK2007/000168 on Mar. 30, 2007, now Pat. No. 8,163,708.

(60) Provisional application No. 60/788,995, filed on Apr. 3, 2006, provisional application No. 60/796,813, filed on May 1, 2006, provisional application No. 60/838,710, filed on Aug. 18, 2006.

(30) Foreign Application Priority Data

Apr. 3, 2006 (DK) .................. 2006 00478
May 1, 2006 (DK) .................. 2006 00615
Oct. 30, 2006 (DK) .................. 2006 01401

(51) Int. Cl.
*C07H 21/04* (2006.01)
*C12N 15/113* (2010.01)

(52) U.S. Cl.
CPC ........ *C12N 15/113* (2013.01); *C12N 2310/113* (2013.01); *C12N 2310/321* (2013.01); *C12N 2310/322* (2013.01); *C12N 2310/3231* (2013.01); *C12N 2310/3515* (2013.01)

(58) Field of Classification Search
CPC .................. C12N 15/113; C12N 2310/113
See application file for complete search history.

(56) References Cited

U.S. PATENT DOCUMENTS

2010/0004320 A1 * 1/2010 Elmen et al. ................ 514/44 R

OTHER PUBLICATIONS

Davis et al. Nucleic Acids Res. (2006) vol. 34, pp. 2294-2304.*
Applicant's response filed Aug. 14, 2013 in U.S. Appl. No. 13/415,685.*

* cited by examiner

*Primary Examiner* — Jon E Angell
(74) *Attorney, Agent, or Firm* — Sterne, Kessler, Goldstein & Fox P.L.L.C.

(57) ABSTRACT

The invention provides pharmaceutical compositions comprising short single stranded oligonucleotides, of length of between 8 and 26 nucleobases which are complementary to human microRNAs selected from the group consisting of miR19b, miR21, miR122a, miR155 and miR375. The short oligonucleotides are particularly effective at alleviating miRNA repression in vivo. It is found that the incorporation of high affinity nucleotide analogs into the oligonucleotides results in highly effective anti-microRNA molecules which appear to function via the formation of almost irreversible duplexes with the miRNA target, rather than RNA cleavage based mechanisms, such as mechanisms associated with RNaseH or RISC.

21 Claims, 20 Drawing Sheets

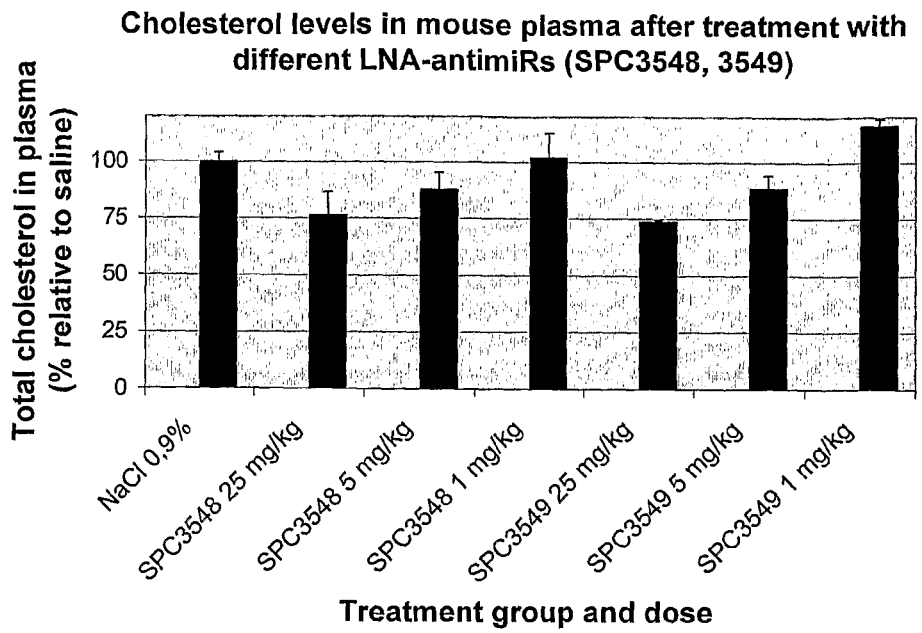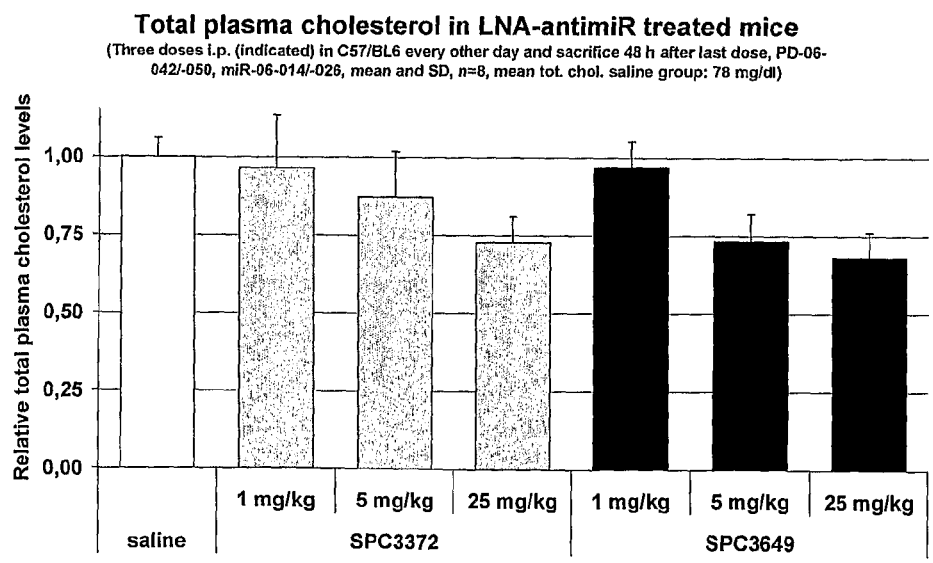
Figure 3 (A and B)

PHARMACEUTICAL COMPOSITION COMPRISING ANTI-MIRNA ANTISENSE OLIGONUCLEOTIDES

FIELD OF THE INVENTION

The present invention concerns pharmaceutical compostions comprising LNA-containing single stranded oligonucleotides capable of inhibiting disease-inducing microRNAs particularly human micro-RNAs miR-19b, miR-21, miR-122A, miR-155 and miR-375.

BACKGROUND OF THE INVENTION

MicroRNAs

Novel Regulators of Gene Expression

MicroRNAs (miRNAs) are an abundant class of short endogenous RNAs that act as post-transcriptional regulators of gene expression by base-pairing with their target mRNAs. The mature miRNAs are processed sequentially from longer hairpin transcripts by the RNAse III ribonucleases Drosha (Lee et al. 2003) and Dicer (Hutvagner et al. 2001, Ketting et al. 2001). To date more than 3400 miRNAs have been annotated in vertebrates, invertebrates and plants according to the miRBase microRNA database release 7.1 in October 2005 (Griffith-Jones 2004, Griffith-Jones et al. 2006), and many miRNAs that correspond to putative genes have also been identified.

Most animal miRNAs recognize their target sites located in 3'-UTRs by incomplete base-pairing, resulting in translational repression of the target genes (Bartel 2004). An increasing body of research shows that animal miRNAs play fundamental biological roles in cell growth and apoptosis (Brennecke et al. 2003), hematopoietic lineage differentiation (Chen et al. 2004), life-span regulation (Boehm and Slack 2005), photoreceptor differentiation (Li and Carthew 2005), homeobox gene regulation (Yekta et al. 2004, Hornstein et al. 2005), neuronal asymmetry (Johnston et al. 2004), insulin secretion (Poy et al. 2004), brain morphogenesis (Giraldez et al. 2005), muscle proliferation and differentiation (Chen, Mandel et al. 2005, Kwon et al. 2005, Sokol and Ambros 2005), cardiogenesis (Zhao et al. 2005) and late embryonic development in vertebrates (Wienholds et al. 2005).

MicroRNAs in Human Diseases miRNAs are involved in a wide variety of human diseases. One is spinal muscular atrophy (SMA), a paediatric neurodegenerative disease caused by reduced protein levels or loss-of-function mutations of the survival of motor neurons (SMN) gene (Paushkin et al. 2002). A mutation in the target site of miR-189 in the human SLITRK1 gene was recently shown to be associated with Tourette's syndrome (Abelson et al. 2005), while another recent study reported that the hepatitis C virus (HCV) RNA genome interacts with a host-cell microRNA, the liver-specific miR-122a, to facilitate its replication in the host (Jopling et al. 2005). Other diseases in which miRNAs or their processing machinery have been implicated, include fragile X mental retardation (FXMR) caused by absence of the fragile X mental retardation protein (FMRP) (Nelson et al. 2003, Jin et al. 2004) and DiGeorge syndrome (Landthaler et al. 2004).

In addition, perturbed miRNA expression patterns have been reported in many human cancers. For example, the human miRNA genes miR15a and miR16-1 are deleted or downregulated in the majority of B-cell chronic lymphocytic leukemia (CLL) cases, where a unique signature of 13 miRNA genes was recently shown to associate with prognosis and progression (Calin et al. 2002, Calin et al. 2005). The role of miRNAs in cancer is further supported by the fact that more than 50% of the human miRNA genes are located in cancer-associated genomic regions or at fragile sites (Calin et al. 2004). Recently, systematic expression analysis of a diversity of human cancers revealed a general down-regulation of miRNAs in tumors compared to normal tissues (Lu et al. 2005). Interestingly, miRNA-based classification of poorly differentiated tumors was successful, whereas mRNA profiles were highly inaccurate when applied to the same samples. miRNAs have also been shown to be deregulated in breast cancer (Iorio et al. 2005), lung cancer (Johnson et al. 2005) and colon cancer (Michael et al. 2004), while the miR-17-92 cluster, which is amplified in human B-cell lymphomas and miR-155 which is upregulated in Burkitt's lymphoma have been reported as the first human miRNA oncogenes (Eis et al. 2005, He et al. 2005). Thus, human miRNAs would not only be highly useful as biomarkers for future cancer diagnostics, but are rapidly emerging as attractive targets for disease intervention by oligonucleotide technologies.

Inhibition of microRNAs Using Single Stranded Oligonucleotides

Several oligonucleotide approaches have been reported for inhibition of miRNAs.

WO03/029459 (Tuschl) claims oligonucleotides which encode microRNAs and their complements of between 18-25 nucleotides in length which may comprise nucleotide analogues. LNA is suggested as a possible nucleotide analogue, although no LNA containing oligonucleotides are disclosed. Tuschl claims that miRNA oligonucleotides may be used in therapy.

US2005/0182005 discloses a 24mer 2'OMe RNA oligoribonucleotide complementary to the longest form of miR 21 which was found to reduce miR 21 induced repression, whereas an equivalent DNA containing oligonucleotide did not. The term 2'OMe-RNA refers to an RNA analogue where there is a substitution to methyl at the 2' position (2'OMethyl).

US2005/0227934 (Tuschl) refers to antimir molecules with up to 50% DNA residues. It also reports that antimirs containing 2' OMe RNA were used against pancreatic microRNAs but it appears that no actual oligonucleotide structures are disclosed.

US20050261218 (ISIS) claims an oligomeric compound comprising a first region and a second region, wherein at least one region comprises a modification and a portion of the oligomeric compound is targeted to a small non-coding RNA target nucleic acid, wherein the small non-coding RNA target nucleic acid is a miRNA. Oligomeric compounds of between 17 and 25 nucleotides in length are claimed. The examples refer to entirely 2' OMe PS compounds, 21mers and 20mers, and 2'OMe gapmer oligonucleotides targeted against a range of pre-miRNA and mature miRNA targets.

Boutla et al, 2003 (Nucleic Acids Research 31: 4973-4980) describe the use of DNA antisense oligonucleotides complementary to 11 different miRNAs in *Drosophila* as well as their use to inactivate the miRNAs by injecting the DNA oligonucleotides into fly embryos. Of the 11 DNA antisense oligonucleotides, only 4 constructs showed severe interference with normal development, while the remaining 7 oligonucleotides didn't show any phenotypes presumably due to their inability to inhibit the miRNA in question.

An alternative approach to this has been reported by Hutvagner et al. (2004) and Leaman et al. (2005), in which 2'-O-methyl antisense oligonucleotides, complementary to the mature miRNA could be used as potent and irreversible inhibitors of short interfering RNA (siRNA) and miRNA function in vitro and in vivo in *Drosophila* and *C. elegans*, thereby inducing a loss-of-function phenotype. A drawback of this method is the need of high 2'-O-methyl oligonucleotide concentrations (100 micromolar) in transfection and injection experiments, which may be toxic to the animal. This method was recently applied to mice studies, by conjugating 2'-O-methyl antisense oligonucleotides complementary to four different miRNAs with cholesterol for silencing miRNAs in vivo (Krützfedt et al. 2005). These so-called antagomirs were administered to mice by intravenous injections. Although these experiments resulted in effective silencing of endogenous miRNAs in vivo, which was found to be specific, efficient and long-lasting, a major drawback was the need of high dosage (80 mg/kg) of 2'-O-Me antagomir for efficient silencing.

Inhibition of microRNAs using LNA-modified oligonucleotides have previously been described by Chan et al. *Cancer Research* 2005, 65 (14) 6029-6033, Lecellier et al. *Science* 2005, 308, 557-560, Naguibneva et al. *Nature Cell Biology* 2006 8 (3), 278-84 and Ørum et al. Gene 2006, (Available online 24 Feb. 2006). In all cases, the LNA-modified anti-mir oligonucleotides were complementary to the entire mature microRNA, i.e. 20-23 nucleotides in length, which hampers efficient in vivo uptake and wide biodistribution of the molecules. Naguibneva (Naguibneva et al. Nature Cell Biology 2006 8 describes the use of mixmer DNA-LNA-DNA antisense oligonucleotide anti-mir to inhibit microRNA miR-181 function in vitro, in which a block of 8 LNA nucleotides is located at the center of the molecule flanked by 6 DNA nucleotides at the 5' end, and 9 DNA nucleotides at the 3' end, respectively. A major drawback of this antisense design is low in vivo stability due to low nuclease resistance of the flanking DNA ends.

While Chan et al. (Chan et al. *Cancer Research* 2005, 65 (14) 6029-6033), and Ørum et al. (Ørum et al. Gene 2006, (Available online 24 Feb. 2006) do not disclose the design of the LNA-modified anti-mir molecules used in their study, Lecellier et al. (Lecellier et al. *Science* 2005, 308, 557-560) describes the use of gapmer LNA-DNA-LNA antisense oligonucleotide anti-mir to inhibit microRNA function, in which a block of 4 LNA nucleotides is located both at the 5' end, and at the 3' end, respectively, with a window of 13 DNA nucleotides at the center of the molecule. A major drawback of this antisense design is low in vivo uptake, as well as low in vivo stability due to the 13 nucleotide DNA stretch in the anti-mir oligonucleotide.

Thus, there is a need in the field for improved oligonucleotides capable of inhibiting microRNAs.

SUMMARY OF THE INVENTION

The present invention is based upon the discovery that the use of short oligonucleotides designed to bind with high affinity to miRNA targets are highly effective in alleviating the repression of mRNA by microRNAs in vivo.

Whilst not wishing to be bound to any specific theory, the evidence disclosed herein indicates that the highly efficient targeting of miRNAs in vivo is achieved by designing oligonucleotides with the aim of forming a highly stable duplex with the miRNA target in vivo. This is achieved by the use of high affinity nucleotide analogues such as at least one LNA units and suitably further high affinity nucleotide analogues, such as LNA, 2'-MOE RNA or 2'-Fluoro nucleotide analogues, in a short, such as 10-17 or 10-16 nucleobase oligonucleotides. In one aspect the aim is to generate an oligonucleotide of a length which is unlikely to form a siRNA complex (i.e. a short oligonucleotide), and with sufficient loading of high affinity nucleotide analogues that the oligonucleotide sticks almost permanently to its miRNA target, effectively forming a stable and non-functional duplex with the miRNA target. We have found that such designs are considerably more effective than the prior art oligonucleotides, particularly gapmer and blockmer designs and oligonucleotides which have a long length, e.g. 20-23mers. The term 2'fluor-DNA refers to a DNA analogue where the is a substitution to fluor at the 2' position (2'F).

The invention provides a pharmaceutical composition comprising an oligonucleotide having a length of between 8 and 17, such as 10 and 17, such as 8-16 or 10-16 nucleobase units, a pharmaceutically acceptable diluent, carrier, or adjuvant, wherein at least one of the nucleobase units of the single stranded oligonucleotide is a high affinity nucleotide analogue, such as a Locked Nucleic Acid (LNA) nucleobase unit, and wherein the single stranded oligonucleotide is complementary to a human microRNA sequence selected from the group consisting of human micro-RNAs miR-19b, miR-21, miR-122A, miR-155 and miR-375.

The invention provides for a pharmaceutical composition comprising an oligonucleotide having a length of from 10 to 26 nucleobase units, and a pharmaceutically acceptable diluent, carrier, or adjuvant, wherein the oligonucleotide comprises a core DNA sequence from positions two to seven or from positions three to eight, counting from the 3' end of 3' acgttt 5' (SEQ ID NO 6, 5'tttgca3'), wherein at least one, such as one, preferably at least two, such as two or three, DNA units in said sequence have been substituted by their corresponding LNA unit and optionally wherein said oligonucleotide does not comprise a region of more than 7 contiguous DNA units.

The invention provides for a pharmaceutical composition comprising an oligonucleotide having a length of from 10 to 26 nucleobase units, and a pharmaceutically acceptable diluent, carrier, or adjuvant, wherein the oligonucleotide comprises a core DNA sequence from positions two to seven or from positions three to eight, counting from the 3' end of 3' ctcaca 5' (SEQ ID NO 7, 5' acactc 3') wherein at least one, such as one, preferably at least two, such as two or three, DNA units in said sequence have been substituted by their corresponding LNA unit and optionally wherein said oligonucleotide does not comprise a region of more than 7 contiguous DNA units.

The invention provides for a pharmaceutical composition comprising an oligonucleotide having a length of from 10 to 26 nucleobase units, and a pharmaceutically acceptable diluent, carrier, or adjuvant, wherein the oligonucleotide comprises a core DNA sequence from positions two to seven or from positions three to eight, counting from the 3' end of 3' ttacga 5' (SEQ ID NO 8, 5'agcatt3') wherein at least one, such as one, preferably at least two, such as two or three, DNA units in said sequence have been substituted by their corresponding LNA unit and optionally wherein said oligonucleotide does not comprise a region of more than 7 contiguous DNA units.

The invention provides for a pharmaceutical composition comprising a single stranded oligonucleotide having a length of from 10 to 26 nucleobase units, and a pharmaceutically acceptable diluent, carrier, or adjuvant, wherein the oligonucleotide comprises a core DNA sequence from positions two to seven or from positions three to eight, counting from the 3' end of 3' acaagc 5' (SEQ ID NO 9, 5' cgaaca 3') wherein at least one, such as one, preferably at least two, such as two or three, DNA units in said sequence have been substituted by their corresponding LNA unit and optionally wherein said oligonucleotide does not comprise a region of more than 7 contiguous DNA units.

The invention provides for a pharmaceutical composition comprising a single stranded oligonucleotide having a length of from 10 to 26 nucleobase units, and a pharmaceutically acceptable diluent, carrier, or adjuvant, wherein the oligonucleotide comprises a core DNA sequence from positions two to seven or from positions three to eight, counting from the 3' end of 3' cgaata 5' (SEQ ID NO 10, 5' ataagc3') wherein at least one, such as one, preferably at least two, such as two or three, DNA units in said sequence have been substituted by their corresponding LNA unit and wherein said oligonucleotide does not comprise a region of more than 7 contiguous DNA units.

The high affinity nucleotide analogues are nucleotide analogues which result in oligonucleotide which has a higher thermal duplex stability with a complementary RNA nucleotide than the binding affinity of an equivalent DNA nucleotide. This is typically determined by measuring the $T_m$.

We have not identified any significant off-target effects when using these short, high affinity oligonucleotides targeted against specific miRNAs. Indeed, the evidence provided herein indicates the effects on mRNA expression are either due to the presence of a complementary sequence to the targeted miRNA (primary mRNA targets) within the mRNA or secondary effects on mRNAs which are regulated by primary mRNA targets (secondary mRNA targets). No toxicity effects were identified indicating no significant detrimental off-target effects.

The invention further provides for the use of an oligonucleotide according to the invention, such as those which may form part of the pharmaceutical composition, for the manufacture of a medicament for the treatment of a disease or medical disorder associated with the presence or over-expression (upregulation) of the microRNA.

The invention further provides for a method for the treatment of a disease or medical disorder associated with the presence or over-expression of the microRNA, comprising the step of administering a composition (such as the pharmaceutical composition) according to the invention to a person in need of treatment.

The invention further provides for a method for reducing the effective amount of a miRNA in a cell or an organism, comprising administering a composition (such as the pharmaceutical composition) according to the invention or a single stranded oligonucleotide according to the invention to the cell or the organism. Reducing the effective amount in this context refers to the reduction of functional miRNA present in the cell or organism. It is recognised that the preferred oligonucleotides according to the invention may not always significantly reduce the actual amount of miRNA in the cell or organism as they typically form very stable duplexes with their miRNA targets.

The invention further provides for a method for de-repression of a target mRNA of a miRNA in a cell or an organism, comprising administering a composition (such as the pharmaceutical composition) or a single stranded oligonucleotide according to the invention to the cell or the organism.

The invention further provides for the use of a single stranded oligonucleotide of between 8-16 such as 8-16 such as between 10-16 nucleobases in length, for the manufacture of a medicament for the treatment of a disease or medical disorder associated with the presence or over-expression of the microRNA.

The invention further provides for a method for the treatment of a disease or medical disorder associated with the presence or over-expression of the microRNA, comprising the step of administering a composition (such as the pharmaceutical composition) comprising a single stranded oligonucleotide of between 8-16 such as between 10-16 nucleobases in length to a person in need of treatment.

The invention further provides for a method for reducing the effective amount of a miRNA target (i.e. the amount of miRNA which is available to repress target mRNAs) in a cell or an organism, comprising administering a composition (such as the pharmaceutical composition) comprising a single stranded oligonucleotide of between 8-16 such as between 10-16 nucleobases to the cell or the organism.

The invention further provides for a method for de-repression of a target mRNA of a miRNA in a cell or an organism, comprising a single stranded oligonucleotide of between 8-16 such as between 10-16 nucleobases or (or a composition comprising said oligonucleotide) to the cell or the organism.

The invention further provides for a method for the synthesis of a single stranded oligonucleotide targeted against a human microRNA selected from the group consisting of human micro-RNAs miR-19b, miR-21, miR-122A, miR-155 and miR-375, such as a single stranded oligonucleotide described herein, said method comprising the steps of:

a. Optionally selecting a first nucleobase, counting from the 3' end, which is a nucleotide analogue, such as an LNA nucleobase.

b. Optionally selecting a second nucleobase, counting from the 3' end, which is an nucleotide analogue, such as an LNA nucleobase.

c. Selecting a region of the single stranded oligonucleotide which corresponds to the miRNA seed region, wherein said region is as defined herein.

d. Optionally selecting a seventh and eight nucleobase is as defined herein.

e. Optionally selecting between 1 and 10 further nucleobases which may be selected from the group consisting of nucleotides (x) and nucleotide analogues (X), such as LNA.

f. Optionally selecting a 5' region of the single stranded oligonucleotide is as defined herein.

g. Optionally selecting a 5' terminal of the single stranded oligonucleotide is as defined herein.

Wherein the synthesis is performed by sequential synthesis of the regions defined in steps a-g, wherein said synthesis may be performed in either the 3'-5' (a to g) or 5'-3' (g to a) direction, and wherein said single stranded oligonucleotide is complementary to a sequence of the miRNA target.

In one embodiment the oligonucleotide of the invention is designed not to be recruited by RISC or to mediate RISC directed cleavage of the miRNA target. It has been considered that by using long oligonucleotides, e.g. 21 or 22mers, particularly RNA oligonucleotides, or RNA 'analogue' oligonucleotide which are complementary to the miRNA target, the oligonucleotide can compete against the target mRNA in terms of RISC complex association, and thereby alleviate miRNA repression of miRNA target mRNAs via the introduction of an oligonucleotide which competes as a substrate for the miRNA.

However, the present invention seeks to prevent such undesirable target mRNA cleavage or translational inhibition by providing oligonucleotides capable of complementary, and apparently in some cases almost irreversible binding to the mature microRNA. This appears to result in a form of protection against degradation or cleavage (e.g. by RISC or RNAseH or other endo or exo-nucleases), which may not result in substantial or even significant reduction of the miRNA (e.g. as detected by northern blot using LNA probes)

within a cell, but ensures that the effective amount of the miRNA, as measured by de-respression analysis is reduced considerably. Therefore, in one aspect, the invention provides oligonucleotides which are purposefully designed not to be compatible with the RISC complex, but to remove miRNA by titration by the oligonucleotide. Although not wishing to be bound to a specific theory of why the oligonucleotides of the present invention are so effective, in analogy with the RNA based oligonucleotides (or complete 2'OMe oligonucleotides), it appears that the oligonucleotides according to the present invention work through non-competitive inhibition of miRNA function as they effectively remove the available miRNA from the cytoplasm, where as the prior art oligonucleotides provide an alternative miRNA substrate, which may act as a competitor inhibitor, the effectiveness of which would be far more dependant upon the concentration of the oligonucleotide in the cytoplasm, as well as the concentration of the target mRNA and miRNA.

Whilst not wishing to be bound to any specific theory, one further possibility that may exist with the use of oligonucleotides of approximately similar length to the miRNA targets (i.e. the miRNA) is that the oligonucleotides could form a siRNA like duplex with the miRNA target, a situation which would reduce the effectiveness of the oligonucleotide. It is also possible that the oligonucleotides themselves could be used as the guiding strand within the RISC complex, thereby generating the possibility of RISC directed degradation of non-specific targets which just happen to have sufficient complementarity to the oligonucleotide guide.

By selecting short oligonucleotides for targeting miRNA sequences, such problems are avoided.

Short oligonucleotides which incorporate LNA are known from the reagents area, such as the LNA (see for example WO2005/098029 and WO 2006/069584). However the molecules designed for diagnostic or reagent use are very different in design than those for pharmaceutical use. For example, the terminal nucleobases of the reagent oligos are typically not LNA, but DNA, and the internucleoside linkages are typically other than phosphorothioate, the preferred linkage for use in the oligonucleotides of the present invention. The invention therefore provides for a novel class of oligonucleotide per se.

The invention further provides for a (single stranded) oligonucleotide as described in the context of the pharmaceutical composition of the invention, wherein said oligonucleotide comprises either
  i) at least one phosphorothioate linkage and/or
  ii) at least one 3' terminal LNA unit, and/or
  iii) at least one 5' terminal LNA unit.

It is preferable for most therapeutic uses that the oligonucleotide is fully phosphorothiolated—the exception being for therapeutic oligonucleotides for use in the CNS, such as in the brain or spine where phosphorothioation can be toxic, and due to the absence of nucleases, phosphodiester bonds may be used, even between consecutive DNA units. As referred to herein, other preferred aspects of the oligonucleotide according to the invention is that the second 3' nucleobase, and/or the $9^{th}$ and $10^{th}$ (from the 3' end), may also be LNA.

The inventors have found that other methods of avoiding RNA cleavage (such as exo-nuclease degradation in blood serum, or RISC associated cleavage of the oligonucleotide according to the invention are possible, and as such the invention also provides for a single stranded oligonucleotide which comprises of either:

a. an LNA unit at position 1 and 2 counting from the 3' end and/or
  b. an LNA unit at position 9 and/or 10, also counting from the 3' end, and/or
  c. either one or two 5' LNA units.

Whilst the benefits of these other aspects may be seen with longer oligonucleotides, such as nucleotide of up to 26 nucleobase units in length, it is considered these features may also be used with the shorter oligonucleotides referred to herein, such as the oligonucleotides of between 8-17, 8-16, 10-17 or 10-16 nucleobases described herein. It is highly preferably that the oligonucleotides comprise high affinity nucleotide analogues, such as those referred to herein, most preferably LNA units.

The inventors have therefore surprisingly found that carefully designed single stranded oligonucleotides comprising locked nucleic acid (LNA) units in a particular order show significant silencing of microRNAs, resulting in reduced microRNA levels. It was found that tight binding of said oligonucleotides to the so-called seed sequence, nucleotides 2 to 8 or 2-7, counting from the 5' end, of the target microRNAs was important. Nucleotide 1 of the target microRNAs is a non-pairing base and is most likely hidden in a binding pocket in the Ago 2 protein. Whilst not wishing to be bound to a specific theory, the present inventors consider that by selecting the seed region sequences, particularly with oligonucleotides that comprise LNA, preferably LNA units in the region which is complementary to the seed region, the duplex between miRNA and oligonucleotide is particularly effective in targeting miRNAs, avoiding off target effects, and possibly providing a further feature which prevents RISC directed miRNA function.

The inventors have surprisingly found that microRNA silencing is even more enhanced when LNA-modified single stranded oligonucleotides do not contain a nucleotide at the 3' end corresponding to this non-paired nucleotide 1. It was further found that two LNA units in the 3' end of the oligonucleotides according to the present invention made said oligonucleotides highly nuclease resistant.

It was further found that the oligonucleotides of the invention which have at least one nucleotide analogue, such as an LNA nucleotide in the positions corresponding to positions 10 and 11, counting from the 5' end, of the target microRNA may prevent cleavage of the oligonucleotides of the invention Accordingly, in one aspect of the invention relates to an oligonucleotide having a length of from 12 to 26 nucleotides, wherein
  i) the first nucleotide, counting from the 3' end, is a locked nucleic acid (LNA) unit;
  ii) the second nucleotide, counting from the 3' end, is an LNA unit; and
  iii) the ninth and/or the tenth nucleotide, counting from the 3' end, is an LNA unit.

The invention further provides for the oligonucleotides as defined herein for use as a medicament.

The invention further relates to compositions comprising the oligonucleotides defined herein and a pharmaceutically acceptable carrier.

As mentioned above, microRNAs are related to a number of diseases. Hence, a fourth aspect of the invention relates to the use of an oligonucleotide as defined herein for the manufacture of a medicament for the treatment of a disease associated with the expression of microRNAs selected from the group consisting of spinal muscular atrophy, Tourette's syndrome, hepatitis C virus, fragile X mental retardation, DiGeorge syndrome and cancer, such as chronic lymphocytic leukemia, breast cancer, lung cancer and colon cancer, in particular cancer.

A further aspect of the invention is a method to reduce the levels of target microRNA by contacting the target microRNA to an oligonucleotide as defined herein, wherein the oligonucleotide
1. is complementary to the target microRNA
2. does not contain a nucleotide at the 3' end that corresponds to the first 5' end nucleotide of the target microRNA.

The invention further provides for an oligonucleotide comprising a nucleobase sequence selected from the group consisting of SEQ ID NO 20, SEQ ID NO 21, SEQ ID NO 22, SEQ ID NO 23, SEQ ID NO 24, SEQ ID NO 25, SEQ ID NO 28, SEQ ID NO 26, SEQ ID NO 27, SEQ ID NO 82, SEQ ID NO 83, SEQ ID NO 84, SEQ ID NO 85, SEQ ID NO 86, SEQ ID NO 87, SEQ ID NO 88, and SEQ ID NO 89; wherein a lowercase letter identifies the nitrogenous base of a DNA unit and an uppercase letter identifies the nitrogenous base of an LNA unit; and wherein the LNA cytosines are optionally methylated, or a conjugate thereof.

The invention further provides for an oligonucleotide comprising a nucleobase sequence selected from the group consisting of SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 90, SEQ ID NO 91, SEQ ID NO 92, SEQ ID NO 93, SEQ ID NO 94, SEQ ID NO 95, SEQ ID NO 96, SEQ ID NO 97, SEQ ID NO 98, SEQ ID NO 99, SEQ ID NO 100, and SEQ ID NO 101; wherein a lowercase letter identifies the nitrogenous base of a DNA unit and an uppercase letter identifies the nitrogenous base of an LNA unit; and wherein the LNA cytosines are optionally methylated, or a conjugate thereof.

The invention further provides for an oligonucleotide comprising a nucleobase sequence selected from the group consisting of SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 102, SEQ ID NO 103, SEQ ID NO 104, and SEQ ID NO 105; wherein a lowercase letter identifies the nitrogenous base of a DNA unit and an uppercase letter identifies the nitrogenous base of an LNA unit; and wherein the LNA cytosines are optionally methylated, or a conjugate thereof.

The invention further provides for an oligonucleotide comprising a nucleobase sequence selected from the group consisting of SEQ ID NO 47, SEQ ID NO 48, SEQ ID NO 49, SEQ ID NO 50, SEQ ID NO 51, SEQ ID NO 52, SEQ ID NO 53, SEQ ID NO 54, SEQ ID NO 55, SEQ ID NO 106, SEQ ID NO 107, SEQ ID NO 108 and SEQ ID NO 109; wherein a lowercase letter identifies the nitrogenous base of a DNA unit and an uppercase letter identifies the nitrogenous base of an LNA unit, and wherein the LNA cytosines are optionally methylated, or a conjugate thereof.

The invention further provides for an oligonucleotide comprising a nucleobase sequence selected from the group consisting of SEQ ID NO 65, SEQ ID NO 66, SEQ ID NO 67, SEQ ID NO 68, and SEQ ID NO 69, SEQ ID NO 38, SEQ ID NO 39, SEQ ID NO 40, SEQ ID NO 41, SEQ ID NO 42, SEQ ID NO 43, SEQ ID NO 44, SEQ ID NO 45, and SEQ ID NO 46, wherein a lowercase letter identifies the nitrogenous base of a DNA unit and an uppercase letter identifies the nitrogenous base of an LNA unit; and wherein the LNA cytosines are optionally methylated, or a conjugate thereof.

In one embodiment, the oligonucleotide may have a nucleobase sequence of between 1-17 nucleobases, such as 8, 9, 10, 11, 12, 13, 14, 15, 16 or 17 nucleobases, and as such the oligonucleobase in such an embodiment may be a contiguous subsequence within the oligonucleotides disclosed herein.

The inventors of the present invention have surprisingly found that antisense oligonucleotides of a certain length comprising a particular core DNA sequence and locked nucleic acids (LNAs) in said core sequence exhibit superior microRNA-inhibiting properties.

BRIEF DESCRIPTION OF THE DRAWINGS

FIG. 3. Assessment of plasma cholesterol levels in LNA-antimiR-122a treated mice compared to the control mice that received saline.

DETAILED DESCRIPTION OF THE INVENTION

Figure 1:
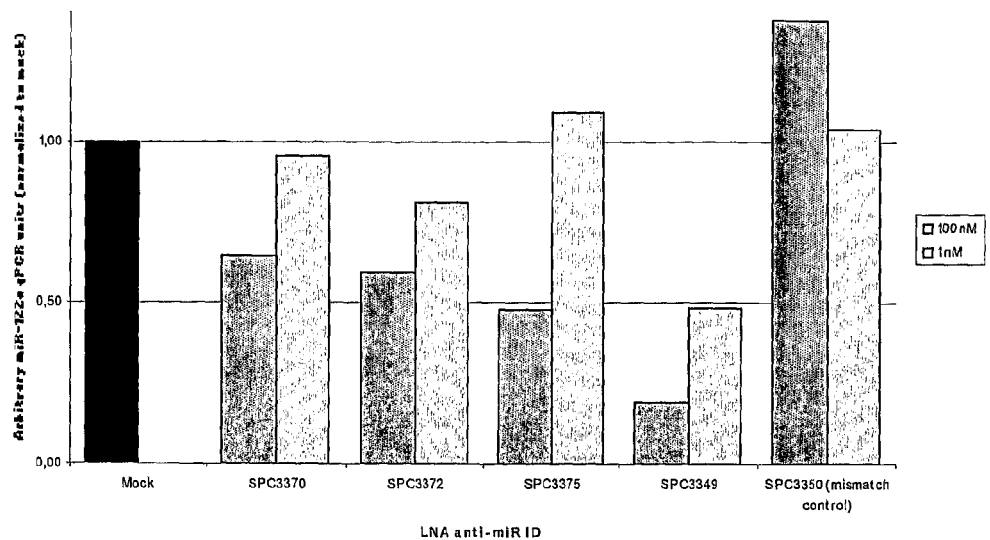
FIG. 1. The effect of treatment with different LNA anti-miR oligonucleotides on target nucleic acid expression in the miR-122a expressing cell line Huh-7. Shown are amounts of miR-122a (arbitrary units) derived from miR-122a specific qRT-PCR as compared to untreated cells (mock). The LNA anti-miR oligonucleotides were used at two concentrations, 1 and 100 nM, respectively. Included is also a mismatch control (SPC3350) to SPC3349 (also referred to herein as SPC3549).

The oligonucleotide of the invention is typically single stranded. It will therefore be understood that within the context of the invention the term oligonucleotide may be used interchangeably with the term single stranded oligonucleotide.

In one embodiment, the invention provides pharmaceutical compositions comprising short (single stranded) oligonucleotides, of length of between 8 and 17 nucleobases in length, such as between 10 and 17 nucleobases which are complementary to human microRNAs. The short oligonucleotides are particularly effective at alleviating miRNA repression in vivo. It is found that the incorporation of high affinity nucleotide analogues into the oligonucleotides results in highly effective anti-microRNA molecules which appear to function via the formation of almost irreversible duplexes with the miRNA target, rather than RNA cleavage based mechanisms, such as mechanisms associated with RNaseH or RISC.

It is highly preferable that the single stranded oligonucleotide according to the invention comprises a region of contiguous nucleobase sequence which is 100% complementary to the human microRNA seed region.

It is preferable that single stranded oligonucleotide according to the invention is complementary to the mature human microRNA sequence.

Preferred oligonucleotides according to the invention are complementary to a microRNA sequence selected from the group consisting of has-miR19b, hsa-miR21, hsa-miR 122, hsa-miR 142 a7b, hsa-miR 155, hsa-miR 375.

In one embodiment, the oligonucleotide according to the invention does not comprise a nucleobase at the 3' end that corresponds to the first 5' end nucleotide of the target microRNA.

In one embodiment, the first nucleobase of the single stranded oligonucleotide according to the invention, counting from the 3' end, is a nucleotide analogue, such as an LNA unit.

In one embodiment, the second nucleobase of the single stranded oligonucleotide according to the invention, counting from the 3' end, is a nucleotide analogue, such as an LNA unit.

In one embodiment, the ninth and/or the tenth nucleotide of the single stranded oligonucleotide according to the invention, counting from the 3' end, is a nucleotide analogue, such as an LNA unit.

In one embodiment, the ninth nucleobase of the single stranded oligonucleotide according to the invention, counting from the 3' end is a nucleotide analogue, such as an LNA unit.

In one embodiment, the tenth nucleobase of the single stranded oligonucleotide according to the invention, counting from the 3' end is a nucleotide analogue, such as an LNA unit.

In one embodiment, both the ninth and the tenth nucleobase of the single stranded oligonucleotide according to the invention, calculated from the 3' end is a nucleotide analogue, such as an LNA unit.

In one embodiment, the single stranded oligonucleotide according to the invention does not comprise a region of more than 5 consecutive DNA nucleotide units. In one embodiment, the single stranded oligonucleotide according to the invention does not comprise a region of more than 6 consecutive DNA nucleotide units. In one embodiment, the single stranded oligonucleotide according to the invention does not comprise a region of more than 7 consecutive DNA nucleotide units. In one embodiment, the single stranded oligonucleotide according to the invention does not comprise a region of more than 8 consecutive DNA nucleotide units. In one embodiment, the single stranded oligonucleotide according to the invention does not comprise a region of more than 3 consecutive DNA nucleotide units. In one embodiment, the single stranded oligonucleotide according to the invention does not comprise a region of more than 2 consecutive DNA nucleotide units.

In one embodiment, the single stranded oligonucleotide comprises at least region consisting of at least two consecutive nucleotide analogue units, such as at least two consecutive LNA units.

In one embodiment, the single stranded oligonucleotide comprises at least region consisting of at least three consecutive nucleotide analogue units, such as at least three consecutive LNA units.

In one embodiment, the single stranded oligonucleotide of the invention does not comprise a region of more than 7 consecutive nucleotide analogue units, such as LNA units. In one embodiment, the single stranded oligonucleotide of the invention does not comprise a region of more than 6 consecutive nucleotide analogue units, such as LNA units. In one embodiment, the single stranded oligonucleotide of the invention does not comprise a region of more than 5 consecutive nucleotide analogue units, such as LNA units. In one embodiment, the single stranded oligonucleotide of the invention does not comprise a region of more than 4 consecutive nucleotide analogue units, such as LNA units. In one embodiment, the single stranded oligonucleotide of the invention does not comprise a region of more than 3 consecutive nucleotide analogue units, such as LNA units. In one embodiment, the single stranded oligonucleotide of the invention does not comprise a region of more than 2 consecutive nucleotide analogue units, such as LNA units.

In one embodiment, the first or second 3' nucleobase of the single stranded oligonucleotide corresponds to the second 5' nucleotide of the microRNA sequence.

In one embodiment, nucleobase units 1 to 6 (inclusive) of the single stranded oligonucleotide as measured from the 3' end the region of the single stranded oligonucleotide are complementary to the microRNA seed region sequence.

In one embodiment, nucleobase units 1 to 7 (inclusive) of the single stranded oligonucleotide as measured from the 3' end the region of the single stranded oligonucleotide are complementary to the microRNA seed region sequence.

In one embodiment, nucleobase units 2 to 7 (inclusive) of the single stranded oligonucleotide as measured from the 3' end the region of the single stranded oligonucleotide are complementary to the microRNA seed region sequence.

In one embodiment, the single stranded oligonucleotide comprises at least one nucleotide analogue unit, such as at least one LNA unit, in a position which is within the region complementary to the miRNA seed region. The single stranded oligonucleotide may, in one embodiment comprise at between one and 6 or between 1 and 7 nucleotide analogue units, such as between 1 and 6 and 1 and 7 LNA units, in a position which is within the region complementary to the miRNA seed region.

In one embodiment, the nucleobase sequence of the single stranded oligonucleotide which is complementary to the sequence of the microRNA seed region, is selected from the group consisting of (X)Xxxxxx, (X)xXxxxx, (X)xxXxxx, (X)xxxXxx, (X)xxxxXx and (X)xxxxxX, as read in a 3'-5'direction, wherein "X" denotes a nucleotide analogue, (X) denotes an optional nucleotide analogue, such as an LNA unit, and "x" denotes a DNA or RNA nucleotide unit.

In one embodiment, the single stranded oligonucleotide comprises at least two nucleotide analogue units, such as at least two LNA units, in positions which are complementary to the miRNA seed region.

In one embodiment, the nucleobase sequence of the single stranded oligonucleotide which is complementary to the sequence of the microRNA seed region, is selected from the group consisting of (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, wherein "X" denotes a nucleotide analogue, such as an LNA unit, (X) denotes an optional nucleotide analogue, such as an LNA unit, and "x" denotes a DNA or RNA nucleotide unit.

In one embodiment, the single stranded oligonucleotide comprises at least three nucleotide analogue units, such as at least three LNA units, in positions which are complementary to the miRNA seed region.

In one embodiment, the nucleobase sequence of the single stranded oligonucleotide which is complementary to the sequence of the microRNA seed region, is selected from the group consisting of (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)xXxXXx, (X)xXxxXX, (X)xxXxXX, (X)xXxXxX and (X)XxXxXx, wherein "X" denotes a nucleotide analogue, such as an LNA unit, (X) denotes an optional nucleotide analogue, such as an LNA unit, and "x" denotes a DNA or RNA nucleotide unit.

In one embodiment, the single stranded oligonucleotide comprises at least four nucleotide analogue units, such as at least four LNA units, in positions which are complementary to the miRNA seed region.

In one embodiment the nucleobase sequence of the single stranded oligonucleotide which is complementary to the sequence of the microRNA seed region, is selected from the group consisting of (X)xxXXX, (X)xXxXXX, (X)xXXxXX, (X)xXXXxX, (X)xXXXXx, (X)XxxXXX, (X)XxXxXX, (X)XxXXxX, (X)XxXXx, (X)XXxxXX, (X)XXxXxX, (X)XXxXXx, (X)XXXxxX, (X)XXXxXx, and (X)XXXXxx, wherein "X" denotes a nucleotide analogue, such as an LNA unit, (X) denotes an optional nucleotide analogue, such as an LNA unit, and "x" denotes a DNA or RNA nucleotide unit.

In one embodiment, the single stranded oligonucleotide comprises at least five nucleotide analogue units, such as at least five LNA units, in positions which are complementary to the miRNA seed region.

In one embodiment, the nucleobase sequence of the single stranded oligonucleotide which is complementary to the sequence of the microRNA seed region, is selected from the group consisting of (X)xXXXXX, (X)XxXXXX, (X)XXxXXX, (X)XXXxXX, (X)XXXXxX and (X)XXXXXx, wherein "X" denotes a nucleotide analogue, such as an LNA unit, (X) denotes an optional nucleotide analogue, such as an LNA unit, and "x" denotes a DNA or RNA nucleotide unit.

In one embodiment, the single stranded oligonucleotide comprises six or seven nucleotide analogue units, such as six or seven LNA units, in positions which are complementary to the miRNA seed region.

In one embodiment, the nucleobase sequence of the single stranded oligonucleotide which is complementary to the sequence of the microRNA seed region, is selected from the group consisting of XXXXXX, XxXXXXX, XXxXXXX, XXXxXXX, XXXXxXX, XXXXXxX and XXXXXXx, wherein "X" denotes a nucleotide analogue, such as an LNA unit, such as an LNA unit, and "x" denotes a DNA or RNA nucleotide unit.

In one embodiment, the two nucleobase motif at position 7 to 8, counting from the 3' end of the single stranded oligonucleotide is selected from the group consisting of xx, XX, xX and Xx, wherein "X" denotes a nucleotide analogue, such as an LNA unit, such as an LNA unit, and "x" denotes a DNA or RNA nucleotide unit.

In one embodiment, the two nucleobase motif at position 7 to 8, counting from the 3' end of the single stranded oligonucleotide is selected from the group consisting of XX, xX and Xx, wherein "X" denotes a nucleotide analogue, such as an LNA unit, such as an LNA unit, and "x" denotes a DNA or RNA nucleotide unit.

In one embodiment, the single stranded oligonucleotide comprises at least 12 nucleobases and wherein the two nucleobase motif at position 11 to 12, counting from the 3' end of the single stranded oligonucleotide is selected from the group consisting of xx, XX, xX and Xx, wherein "X" denotes a nucleotide analogue, such as an LNA unit, such as an LNA unit, and "x" denotes a DNA or RNA nucleotide unit.

In one embodiment, the single stranded oligonucleotide comprises at least 12 nucleobases and wherein the two nucleobase motif at position 11 to 12, counting from the 3' end of the single stranded oligonucleotide is selected from the group consisting of XX, xX and Xx, wherein "X" denotes a nucleotide analogue, such as an LNA unit, such as an LNA unit, and "x" denotes a DNA or RNA nucleotide unit.

In one embodiment, the single stranded oligonucleotide comprises at least 13 nucleobases and wherein the three nucleobase motif at position 11 to 13, counting from the 3' end, is selected from the group consisting of xxx, Xxx, xXx, xxX, XXx, XxX, xXX and XXX, wherein "X" denotes a nucleotide analogue, such as an LNA unit, such as an LNA unit, and "x" denotes a DNA or RNA nucleotide unit.

In one embodiment, the three nucleobase motif at position 11 to 13, counting from the 3' end of the single stranded oligonucleotide, is selected from the group consisting of Xxx, xXx, xxX, XXx, XxX, xXX and XXX, wherein "X" denotes a nucleotide analogue, such as an LNA unit, such as an LNA unit, and "x" denotes a DNA or RNA nucleotide unit.

In one embodiment, the single stranded oligonucleotide comprises at least 14 nucleobases and wherein the four nucleobase motif at positions 11 to 14, counting from the 3' end, is selected from the group consisting of xxxx, Xxxx, xXxx, xxXx, xxxX, XXxx, XxXx, XxxX, xXXx, xXxX, xxXX, XXXx, XxXX, xXXX, XXxX and XXXX wherein "X" denotes a nucleotide analogue, such as an LNA unit, such as an LNA unit, and "x" denotes a DNA or RNA nucleotide unit.

In one embodiment, the four nucleobase motif at position 11 to 14 of the single stranded oligonucleotide, counting from the 3' end, is selected from the group consisting of Xxxx, xXxx, xxXx, xxxX, XXxx, XxXx, XxxX, xXXx, xXxX, xxXX, XXXx, XxXX, xXXX, XXxX and XXXX, wherein "X" denotes a nucleotide analogue, such as an LNA unit, and "x" denotes a DNA or RNA nucleotide unit.

In one embodiment, the single stranded oligonucleotide comprises 15 nucleobases and the five nucleobase motif at position 11 to 15, counting from the 3' end, is selected from the group consisting of Xxxxx, xXxxx, xxXxx, xxxXx, xxxxX, XXxxx, XxXxx, XxxXx, XxxxX, xXXxx, xXxXx, xXxxX, xxXXx, xxXxX, xxxXX, XXXxx, XXxXx, XxxXX, XXXXx, xxXXX, XXxXX, XxXxX, XXXXx, XXXxX, XXxXX, XxXXXX, xXXXX, and XXXXX wherein "X" denotes a nucleotide analogue, such as an LNA unit, such as an LNA unit, and "x" denotes a DNA or RNA nucleotide unit.

In one embodiment, the single stranded oligonucleotide comprises 16 nucleobases and the six nucleobase motif at positions 11 to 16, counting from the 3' end, is selected from the group consisting of Xxxxxx, xXxxxx, xxXxxx, xxxXxx, xxxxXx, xxxxxX, XXxxxx, XxXxxx, XxxXxx, XxxxXx, XxxxxX, xXXxxx, xXXxxx, xXxXxx, xXxxXx, xXxxxX, xxXXxx, xxXxXx, xxXxxX, xxxXXx, xxxXxX, xxxxXX, XXXxxx, XXxXxx, XXxxXx, XXxxxX, XxXXxx, XxXxXx, XxXxxX, XxxXXx, XxxXxX, XxxxXX, xXXXxx, xXXxXx, xXXxxX, xXxXXx, xXxXxX, xXxxXX, xxXXXx, xxXXxX, xxXxXX, xxxXXX, XXXXxx, XXXxxX, XXxxXX, XxxXXX, xxXXXX, xXxXXX, XxXxXX, XXxXxX, XXXxXx, xXXxXX, XxXXxX, XXxXXx, xXXXxX, XxXXXx, xXXXXx, xXXXXX, XxXXXXX, XXxXXX, XXXxXX, XXXXxX, XXXXXx, and XXXXXX wherein "X" denotes a nucleotide analogue, such as an LNA unit, such as an LNA unit, and "x" denotes a DNA or RNA nucleotide unit.

In one embodiment, the six nucleobase motif at positions 11 to 16 of the single stranded oligonucleotide, counting from the 3' end, is xxXxxX, wherein "X" denotes a nucleotide analogue, such as an LNA unit, such as an LNA unit, and "x" denotes a DNA or RNA nucleotide unit.

In one embodiment, the three 5' most nucleobases, is selected from the group consisting of Xxx, xXx, xxX, XXx, XxX, xXX and XXX, wherein "X" denotes a nucleotide analogue, such as an LNA unit, such as an LNA unit, and "x" denotes a DNA or RNA nucleotide unit.

In one embodiment, x" denotes a DNA unit.

In one embodiment, the single stranded oligonucleotide comprises a nucleotide analogue unit, such as an LNA unit, at the 5' end.

In one embodiment, the nucleotide analogue units, such as X, are independently selected form the group consisting of: 2'-O-alkyl-RNA unit, 2'-OMe-RNA unit, 2'-amino-DNA unit, 2'-fluoro-DNA unit, LNA unit, PNA unit, HNA unit, INA unit.

In one embodiment, all the nucleobases of the single stranded oligonucleotide of the invention are nucleotide analogue units.

In one embodiment, the nucleotide analogue units, such as X, are independently selected form the group consisting of: 2'-OMe-RNA units, 2'-fluoro-DNA units, and LNA units, In one embodiment, the single stranded oligonucleotide comprises said at least one LNA analogue unit and at least one further nucleotide analogue unit other than LNA.

In one embodiment, the non-LNA nucleotide analogue unit or units are independently selected from 2'-OMe RNA units and 2'-fluoro DNA units.

In one embodiment, the single stranded oligonucleotide consists of at least one sequence XYX or YXY, wherein X is LNA and Y is either a 2'-OMe RNA unit and 2'-fluoro DNA unit.

In one embodiment, the sequence of nucleobases of the single stranded oligonucleotide consists of alternative X and Y units.

In one embodiment, the single stranded oligonucleotide comprises alternating LNA and DNA units (Xx) or (xX).

In one embodiment, the single stranded oligonucleotide comprises a motif of alternating LNA followed by 2 DNA units (Xxx), xXx or xxX.

In one embodiment, at least one of the DNA or non-LNA nucleotide analogue units are replaced with a LNA nucleobase in a position selected from the positions identified as LNA nucleobase units in any one of the embodiments referred to above.

In one embodiment, "X" donates an LNA unit.

In one embodiment, the single stranded oligonucleotide comprises at least 2 nucleotide analogue units, such as at least 3 nucleotide analogue units, such as at least 4 nucleotide analogue units, such as at least 5 nucleotide analogue units, such as at least 6 nucleotide analogue units, such as at least 7 nucleotide analogue units, such as at least 8 nucleotide analogue units, such as at least 9 nucleotide analogue units, such as at least 10 nucleotide analogue units.

In one embodiment, the single stranded oligonucleotide comprises at least 2 LNA units, such as at least 3 LNA units, such as at least 4 LNA units, such as at least 5 LNA units, such as at least 6 LNA units, such as at least 7 LNA units, such as at least 8 LNA units, such as at least 9 LNA units, such as at least 10 LNA units.

In one embodiment wherein at least one of the nucleotide analogues, such as LNA units, is either cytosine or guanine, such as between 1-10 of the of the nucleotide analogues, such as LNA units, is either cytosine or guanine, such as 2, 3, 4, 5, 6, 7, 8, or 9 of the of the nucleotide analogues, such as LNA units, is either cytosine or guanine.

In one embodiment at least two of the nucleotide analogues such as LNA units is either cytosine or guanine. In one embodiment at least three of the nucleotide analogues such as LNA units is either cytosine or guanine. In one embodiment at least four of the nucleotide analogues such as LNA units is either cytosine or guanine. In one embodiment at least five of the nucleotide analogues such as LNA units is either cytosine or guanine. In one embodiment at least six of the nucleotide analogues such as LNA units is either cytosine or guanine. In one embodiment at least seven of the nucleotide analogues such as LNA units is either cytosine or guanine. In one embodiment at least eight of the nucleotide analogues such as LNA units is either cytosine or guanine.

In a preferred embodiment the nucleotide analogues have a higher thermal duplex stability a complementary RNA nucleotide than the binding affinity of an equivalent DNA nucleotide to said complementary RNA nucleotide.

In one embodiment, the nucleotide analogues confer enhanced serum stability to the single stranded oligonucleotide.

In one embodiment, the single stranded oligonucleotide forms an A-helix conformation with a complementary single stranded RNA molecule.

A duplex between two RNA molecules typically exists in an A-form conformation, where as a duplex between two DNA molecules typically exits in a B-form conformation. A duplex between a DNA and RNA molecule typically exists in a intermediate conformation (A/B form). The use of nucleotide analogues, such as beta-D-oxy LNA can be used to promote a more A form like conformation. Standard circular dichromisms (CD) or NMR analysis is used to determine the form of duplexes between the oligonucleotides of the invention and complementary RNA molecules.

As recruitment by the RISC complex is thought to be dependant upon the specific structural conformation of the miRNA/mRNA target, the oligonucleotides according to the present invention may, in one embodiment form a A/B-form duplex with a complementary RNA molecule.

However, we have also determined that the use of nucleotide analogues which promote the A-form structure can also be effective, such as the alpha-L isomer of LNA.

In one embodiment, the single stranded oligonucleotide forms an A/B-form conformation with a complementary single stranded RNA molecule.

In one embodiment, the single stranded oligonucleotide forms an A-from conformation with a complementary single stranded RNA molecule.

In one embodiment, the single stranded oligonucleotide according to the invention does not mediate RNAseH based cleavage of a complementary single stranded RNA molecule.

Typically a stretch of at least 5 (typically not effective of RNAse H recruitment), more preferably at least 6, more preferably at least 7 or 8 consecutive DNA nucleobases (or alternative nucleobases which can recruit RNAseH, such as alpha L-amino LNA) are required in order for an oligonucleotide to be effective in recruitment of RNAseH.

EP 1 222 309 provides in vitro methods for determining RNaseH activity, which may be used to determine the ability to recruit RNaseH. A compound is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

A compound is deemed essentially incapable of recruiting RNaseH if, when provided with the complementary RNA target, and RNaseH, the RNaseH initial rate, as measured in pmol/l/min, is less than 1%, such as less than 5%, such as less than 10% or less than 20% of the initial rate determined using the equivalent DNA only oligonucleotide, with no 2' substitutions, with phosphiothiote linkage groups between all nucleotides in the oligonucleotide, using the methodology provided by Example 91-95 of EP 1 222 309.

In a highly preferred embodiment, the single stranded oligonucleotide of the invention is capable of forming a duplex with a complementary single stranded RNA nucleic acid molecule (typically of about the same length of said single stranded oligonucleotide) with phosphodiester internucleoside linkages, wherein the duplex has a $T_m$ of at least about 60° C., indeed it is preferred that the single stranded oligonucleotide is capable of forming a duplex with a complementary single stranded RNA nucleic acid molecule with phosphodiester internucleoside linkages, wherein the duplex has a $T_m$ of between about 70° C. to about 95° C., such as a $T_m$ of between about 70° C. to about 90° C., such as between about 70° C. and about 85° C.

In one embodiment, the single stranded oligonucleotide is capable of forming a duplex with a complementary single stranded DNA nucleic acid molecule with phosphodiester internucleoside linkages, wherein the duplex has a $T_m$ of between about 50° C. to about 95° C., such as between about 50° C. to about 90° C., such as at least about 55° C., such as at least about 60° C., or no more than about 95° C.

The single stranded oligonucleotide may, in one embodiment have a length of between 14-16 nucleobases, including 15 nucleobases.

In one embodiment, the LNA unit or units are independently selected from the group consisting of oxy-LNA, thio-LNA, and amino-LNA, in either of the D-β and L-α configurations or combinations thereof.

In one specific embodiment the LNA units may be an ENA nucleobase.

In one the embodiment the LNA units are beta D oxy-LNA.

In one embodiment the LNA units are in alpha-L amino LNA.

In a preferable embodiment, the single stranded oligonucleotide comprises between 3 and 17 LNA units.

In one embodiment, the single stranded oligonucleotide comprises at least one internucleoside linkage group which differs from phosphate.

In one embodiment, the single stranded oligonucleotide comprises at least one phosphorothioate internucleoside linkage.

In one embodiment, the single stranded oligonucleotide comprises phosphodiester and phosphorothioate linkages.

In one embodiment, the all the internucleoside linkages are phosphorothioate linkages.

In one embodiment, the single stranded oligonucleotide comprises at least one phosphodiester internucleoside linkage.

In one embodiment, all the internucleoside linkages of the single stranded oligonucleotide of the invention are phosphodiester linkages.

In one embodiment, pharmaceutical composition according to the invention comprises a carrier such as saline or buffered saline.

In one embodiment, the method for the synthesis of a single stranded oligonucleotide targeted against a human microRNA, is performed in the 3' to 5' direction a-f.

The method for the synthesis of the single stranded oligonucleotide according to the invention may be performed using standard solid phase oligonucleotide synthesis.

Further embodiments of the invention, which may be combined with the above embodiments are shown in the claims and under the title 'Further embodiments'.

DEFINITIONS

The term 'nucleobase' refers to nucleotides, such as DNA and RNA, and nucleotide analogues.

The term "oligonucleotide" (or simply "oligo") refers, in the context of the present invention, to a molecule formed by covalent linkage of two or more nucleobases. When used in the context of the oligonucleotide of the invention (also referred to the single stranded oligonucleotide), the term "oligonucleotide" may have, in one embodiment, for example between 8-26 nucleobases, such between 10 to 26 nucleobases such between 12 to 26 nucleobases. In a preferable embodiment, as detailed herein, the oligonucleotide of the invention has a length of between 8-17 nucleobases, such as between 20-27 nucleobases such as between 8-16 nucleobases, such as between 12-15 nucleobases, In such an embodiment, the oligonucleotide of the invention may have a length of 8, 9, 10, 11, 12, 13, 14, 15, 16, 17, 18, 19, 20, 21, 22, 23, 24, 25 or 26 nucleobases.

It will be recognised that for shorter oligonucleotides it may be necessary to increase the proportion of (high affinity) nucleotide analogues, such as LNA. Therefore in one embodiment at least about 30% of the nucleobases are nucleotide analogues, such as at least about 33%, such as at least about 40%, or at least about 50% or at least about 60%, such as at least about 66%, such as at least about 70%, such as at least about 80%, or at least about 90%. It will also be apparent that the oligonucleotide may comprise of a nucleobase sequence which consists of only nucleotide analogue sequences.

Herein, the term "nitrogenous base" is intended to cover purines and pyrimidines, such as the DNA nucleobases A, C, T and G, the RNA nucleobases A, C, U and G, as well as non-DNA/RNA nucleobases, such as 5-methylcytosine ($^{Me}C$), isocytosine, pseudoisocytosine, 5-bromouracil, 5-propynyluracil, 5-propyny-6-fluorouracil, 5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine, in particular $^{Me}C$. It will be understood that the actual selection of the non-DNA/RNA nucleobase will depend on the corresponding (or matching) nucleotide present in the microRNA strand which the oligonucleotide is intended to target. For example, in case the corresponding nucleotide is G it will normally be necessary to select a non-DNA/RNA nucleobase which is capable of establishing hydrogen bonds to G. In this specific case, where the corresponding nucleotide is G, a typical example of a preferred non-DNA/RNA nucleobase is $^{Me}C$.

The term "internucleoside linkage group" is intended to mean a group capable of covalently coupling together two nucleobases, such as between DNA units, between DNA units and nucleotide analogues, between two non-LNA units, between a non-LNA unit and an LNA unit, and between two LNA units, etc. Preferred examples include phosphate, phosphodiester groups and phosphorothioate groups.

The internucleoside linkage may be selected form the group consisting of: —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, and/or the internucleoside linkage may be selected form the group consisting of: —O—CO—O—, —O—CO—NR$^H$—, —NR$^H$—CO—CH$_2$—, —O—CH$_2$—CO—NR$^H$—, —O—CH$_2$—CH$_2$—NR$^H$—, —CO—NR$^H$—CH$_2$—, —CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl. Suitably, in some embodiments, sulphur (S) containing internucleoside linkages as provided above may be preferred The terms "corresponding to" and "corresponds to" as used in the context of oligonucleotides refers to the comparison between either a nucleobase sequence of the compound of the invention, and the reverse complement thereof, or in one embodiment between a nucleobase sequence and an equivalent (identical) nucleobase sequence which may for example comprise other nucleobases but retains the same base sequence, or complement thereof. Nucleotide analogues are compared directly to their equivalent or corresponding natural nucleotides. Sequences which form the reverse complement of a sequence are referred to as the complement sequence of the sequence.

When referring to the length of a nucleotide molecule as referred to herein, the length corresponds to the number of monomer units, i.e. nucleobases, irrespective as to whether those monomer units are nucleotides or nucleotide analogues. With respect to nucleobases, the terms monomer and unit are used interchangeably herein.

It should be understood that when the term "about" is used in the context of specific values or ranges of values, the disclosure should be read as to include the specific value or range referred to.

Preferred DNA analogues includes DNA analogues where the 2'-H group is substituted with a substitution other than —OH (RNA) e.g. by substitution with —O—CH$_3$, —O—CH$_2$—CH$_2$—O—CH$_3$, —O—CH$_2$—CH$_2$—CH$_2$—NH$_2$, —O—CH$_2$—CH$_2$—CH$_2$—OH or —F.

Preferred RNA analogues includes RNA analogues which have been modified in its 2'-OH group, e.g. by substitution with a group other than —H (DNA), for example —O—CH$_3$, —O—CH$_2$—CH$_2$—O—CH$_3$, —O—CH$_2$—CH$_2$—CH$_2$—NH$_2$, —O—CH$_2$—CH$_2$—CH$_2$—OH or —F.

In one embodiment the nucleotide analogue is "ENA".

When used in the present context, the terms "LNA unit", "LNA monomer", "LNA residue", "locked nucleic acid unit", "locked nucleic acid monomer" or "locked nucleic acid residue", refer to a bicyclic nucleoside analogue. LNA units are described in inter alia WO 99/14226, WO 00/56746, WO 00/56748, WO 01/25248, WO 02/28875, WO 03/006475 and WO 03/095467. The LNA unit may also be defined with respect to its chemical formula. Thus, an "LNA unit", as used herein, has the chemical structure shown in Scheme 1 below:

Scheme 1

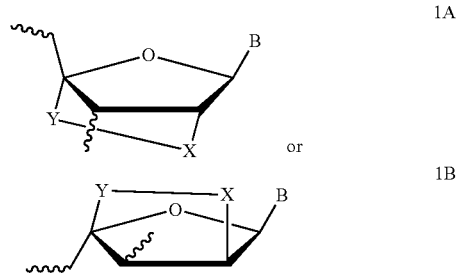

wherein
X is selected from the group consisting of O, S and NR$^H$, where R$^H$ is H or C$_{1-4}$-alkyl;
Y is (—CH$_2$)$_r$, where r is an integer of 1-4; and
B is a nitrogenous base.

When referring to substituting a DNA unit by its corresponding LNA unit in the context of the present invention, the term "corresponding LNA unit" is intended to mean that the DNA unit has been replaced by an LNA unit containing the same nitrogenous base as the DNA unit that it has replaced, e.g. the corresponding LNA unit of a DNA unit containing the nitrogenous base A also contains the nitrogenous base A. The exception is that when a DNA unit contains the base C, the corresponding LNA unit may contain the base C or the base $^{Me}C$, preferably $^{Me}C$.

Herein, the term "non-LNA unit" refers to a nucleoside different from an LNA-unit, i.e. the term "non-LNA unit" includes a DNA unit as well as an RNA unit. A preferred non-LNA unit is a DNA unit.

The terms "unit", "residue" and "monomer" are used interchangeably herein.

In the present context the term "conjugate" is intended to indicate a heterogenous molecule formed by the covalent attachment of an oligonucleotide as described herein to one or more non-nucleotide or non-polynucleotide moieties. Examples of non-nucleotide or non-polynucleotide moieties include macromolecular agents such as proteins, fatty acid chains, sugar residues, glycoproteins, polymers, or combinations thereof. Typically proteins may be antibodies for a target protein. Typical polymers may be polyethelene glycol.

The term "at least one" encompasses an integer larger than or equal to 1, such as 1, 2, 3, 4, 5, 6, 7, 8, 9, 10, 11, 12, 13, 14, 15, 16, 17, 18, 19, 20 and so forth.

The terms "a" and "an" as used about a nucleotide, an agent, an LNA unit, etc., is intended to mean one or more. In particular, the expression "a component (such as a nucleotide, an agent, an LNA unit, or the like) selected from the group consisting of . . . " is intended to mean that one or more of the cited components may be selected. Thus, expressions like "a component selected from the group consisting of A, B and C" is intended to include all combinations of A, B and C, i.e. A, B, C, A+B, A+C, B+C and A+B+C.

The term "thio-LNA unit" refers to an LNA unit in which X in Scheme 1 is S. A thio-LNA unit can be in both the beta-D form and in the alpha-L form. Generally, the beta-D form of the thio-LNA unit is preferred. The beta-D-form and alpha- L-form of a thio-LNA unit are shown in Scheme 3 as compounds 3A and 3B, respectively.

The term "amino-LNA unit" refers to an LNA unit in which X in Scheme 1 is NH or $NR^H$, where $R^H$ is hydrogen or $C_{1-4}$-alkyl. An amino-LNA unit can be in both the beta-D form and in the alpha-L form. Generally, the beta-D form of the amino-LNA unit is preferred. The beta-D-form and alpha-L-form of an amino-LNA unit are shown in Scheme 4 as compounds 4A and 4B, respectively.

The term "oxy-LNA unit" refers to an LNA unit in which X in Scheme 1 is O. An Oxy-LNA unit can be in both the beta-D form and in the alpha-L form. Generally, the beta-D form of the oxy-LNA unit is preferred. The beta-D form and the alpha-L form of an oxy-LNA unit are shown in Scheme 5 as compounds 5A and 5B, respectively.

In the present context, the term "$C_{1-6}$-alkyl" is intended to mean a linear or branched saturated hydrocarbon chain wherein the longest chains has from one to six carbon atoms, such as methyl, ethyl, n-propyl, isopropyl, n-butyl, isobutyl, sec-butyl, tert-butyl, pentyl, isopentyl, neopentyl and hexyl. A branched hydrocarbon chain is intended to mean a $C_{1-6}$-alkyl substituted at any carbon with a hydrocarbon chain.

In the present context, the term "$C_{1-4}$-alkyl" is intended to mean a linear or branched saturated hydrocarbon chain wherein the longest chains has from one to four carbon atoms, such as methyl, ethyl, n-propyl, isopropyl, n-butyl, isobutyl, sec-butyl and tert-butyl. A branched hydrocarbon chain is intended to mean a $C_{1-4}$-alkyl substituted at any carbon with a hydrocarbon chain.

When used herein the term "$C_{1-6}$-alkoxy" is intended to mean $C_{1-6}$-alkyl-oxy, such as methoxy, ethoxy, n-propoxy, isopropoxy, n-butoxy, isobutoxy, sec-butoxy, tert-butoxy, pentoxy, isopentoxy, neopentoxy and hexoxy.

In the present context, the term "$C_{2-5}$-alkenyl" is intended to mean a linear or branched hydrocarbon group having from two to six carbon atoms and containing one or more double bonds. Illustrative examples of $C_{2-6}$-alkenyl groups include allyl, homo-allyl, vinyl, crotyl, butenyl, butadienyl, pentenyl, pentadienyl, hexenyl and hexadienyl. The position of the unsaturation (the double bond) may be at any position along the carbon chain.

In the present context the term "$C_{2-6}$-alkynyl" is intended to mean linear or branched hydrocarbon groups containing from two to six carbon atoms and containing one or more triple bonds. Illustrative examples of $C_{2-6}$-alkynyl groups include acetylene, propynyl, butynyl, pentynyl and hexynyl. The position of unsaturation (the triple bond) may be at any position along the carbon chain. More than one bond may be unsaturated such that the "$C_{2-6}$-alkynyl" is a di-yne or enediyne as is known to the person skilled in the art.

As used herein, "hybridisation" means hydrogen bonding, which may be Watson-Crick, Hoogsteen, reversed Hoogsteen hydrogen bonding, etc., between complementary nucleoside or nucleotide bases. The four nucleobases commonly found in DNA are G, A, T and C of which G pairs with C, and A pairs with T. In RNA T is replaced with uracil (U), which then pairs with A. The chemical groups in the nucleobases that participate in standard duplex formation constitute the Watson-Crick face. Hoogsteen showed a couple of years later that the purine nucleobases (G and A) in addition to their Watson-Crick face have a Hoogsteen face that can be recognised from the outside of a duplex, and used to bind pyrimidine oligonucleotides via hydrogen bonding, thereby forming a triple helix structure.

In the context of the present invention "complementary" refers to the capacity for precise pairing between two nucleotides sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA strand are considered complementary to each other when a sufficient number of nucleotides in the oligonucleotide can form hydrogen bonds with corresponding nucleotides in the target DNA or RNA to enable the formation of a stable complex. To be stable in vitro or in vivo the sequence of an oligonucleotide need not be 100% complementary to its target microRNA.

The terms "complementary" and "specifically hybridisable" thus imply that the oligonucleotide binds sufficiently strong and specific to the target molecule to provide the desired interference with the normal function of the target whilst leaving the function of non-target RNAs unaffected In a preferred example the oligonucleotide of the invention is 100% complementary to a human microRNA sequence, such as one of the microRNA sequences referred to herein.

In a preferred example, the oligonucleotide of the invention comprises a contiguous sequence which is 100% complementary to the seed region of the human microRNA sequence.

MicroRNAs are short, non-coding RNAs derived from endogenous genes that act as post-transcriptional regulators of gene expression. They are processed from longer (ca 70-80 nt) hairpin-like precursors termed pre-miRNAs by the RNAse III enzyme Dicer. MicroRNAs assemble in ribonucleoprotein complexes termed miRNPs and recognize their target sites by antisense complementarity thereby mediating down-regulation of their target genes. Near-perfect or perfect complementarity between the miRNA and its target site results in target mRNA cleavage, whereas limited complementarity between the microRNA and the target site results in translational inhibition of the target gene.

The term "microRNA" or "miRNA", in the context of the present invention, means an RNA oligonucleotide consisting of between 18 to 25 nucleotides. In functional terms miRNAs are typically regulatory endogenous RNA molecules.

The terms "target microRNA" or "target miRNA" or "miRNA target" refer to a microRNA with a biological role in human disease, e.g. an upregulated, oncogenic miRNA or a tumor suppressor miRNA in cancer, thereby being a target for therapeutic intervention of the disease in question.

The terms "target gene" or "target mRNA" refer to regulatory mRNA targets of microRNAs, in which said "target gene" or "target mRNA" is regulated post-transcriptionally by the microRNA based on near-perfect or perfect complementarity between the miRNA and its target site resulting in target mRNA cleavage; or limited complementarity, often conferred to complementarity between the so-called seed sequence (nucleotides 2-7 of the miRNA) and the target site resulting in translational inhibition of the target mRNA.

In the context of the present invention the oligonucleotide is single stranded, this refers to the situation where the oligonucleotide is in the absence of a complementary oligonucleotide—i.e. it is not a double stranded oligonucleotide complex, such as an siRNA. In one embodiment, the composition according of the invention does not comprise a further oligonucleotide which has a region of complementarity with the single stranded oligonucleotide of five or more consecutive nucleobases, such as eight or more, or 12 or more of more consecutive nucleobases. It is considered that the further oligonucleotide is not covalently linked to the single stranded oligonucleotide.

LNA-Containing Oligonucleotides of the Invention

While LNA units and non-LNA units may be combined in a number of ways to form oligonucleotides, it has surprisingly been found by the inventors of the present invention that a certain core DNA sequence and a certain presence of LNA units in said DNA sequence results in a particularly high inhibition of microRNA. This presence of LNA units in said core sequence of the oligonucleotides of the present invention made said oligonucleotides highly nuclease resistant.

The nucleotides outside the core sequence may be both LNA units and/or non-LNA units. In one embodiment, the non-LNA units outside the core sequence are DNA units.

the Core Sequence

In order for the antisense oligonucleotides of the present invention to inhibit their target microRNAs as efficiently as possible there needs to be a certain degree of complementarity between the antisense oligonucleotide of the present invention and the corresponding target microRNA.

It is particularly important for the oligonucleotides of the present invention to be complementary with positions 3 to 8, counting from the 5' end, of the corresponding target microRNA. Nucleotide 1, counting from the 5' end, in some of the target microRNAs is a non-pairing base and is most likely hidden in a binding pocket in the Ago 2 protein. Accordingly, the oligonucleotide of the invention may or may not have a nucleotide in position 1, counting from the 3' end, corresponding to nucleotide 1, counting from the 5' end, of the corresponding target microRNA. In some cases, the first two nucleotides, counting from the 5' end, of the corresponding target microRNA may be left unmatched.

The core sequence of the oligonucleotides of the present invention is therefore a DNA sequence from positions one to six, two to seven or positions three to eight, counting from the 3' end, corresponding to positions three to eight, counting from the 5' end, of the corresponding target microRNA.

miR-19b

One particular target microRNA is termed miR-19b. The sequence of miR-19b from positions three to eight, counting from the 5' end, is ugcaaa (see GenBank loci A3421740 and AJ421739). The corresponding DNA sequence is acgttt. The inventors of the present invention have furthermore found that in order to maximize inhibition of the target microRNAs, the oligonucleotides of the present invention must contain at least one LNA unit in its core sequence.

Accordingly, a first aspect of the invention relates to an oligonucleotide according to the invention, such as an oligonucleotide having a length of from 12 to 26 nucleotides having the DNA sequence from positions one to six, two to seven or three to eight, preferably from positions two to seven or three to eight, counting from the 3' end:

acgttt, (SEQ ID NO 6)

wherein at least one, such as one, preferably at least two, such as two or three, DNA units in said sequence have been substituted by their corresponding LNA unit.

Complementarity with further nucleotides of the target microRNA may enhance the inhibition of said target microRNA. Therefore, one embodiment is the oligonucleotide as described above having a DNA sequence from positions one to seven, two to eight or three to nine, preferably from positions two to eight or three to nine, counting from the 3' end:

acgttta, (SEQ ID NO 70)

wherein at least one, such as one, preferably at least two, such as two, more preferably at least three, such as three or four, DNA units in said sequence have been substituted by their corresponding LNA unit.

In another embodiment, the oligonucleotide according to the present invention has a DNA sequence from positions one to eight, two to nine or three to ten, preferably from positions two to nine or three to ten, counting from the 3' end:

acgtttag, (SEQ ID NO 71)

wherein at least one, such as one, preferably at least two, such as two, more preferably at least three, such as three or four, DNA units in said sequence have been substituted by their corresponding LNA unit.

In yet another embodiment, the oligonucleotide according to the present invention has a DNA sequence from positions one to nine, two to ten or three to eleven, preferably from positions two to ten or three to eleven, counting from the 3' end:

acgtttagg, (SEQ ID NO 72)

wherein at least one, such as one, preferably at least two, such as two, more preferably at least three, such as three, even more preferably at least four, such as four or five, DNA units in said sequence have been substituted by their corresponding LNA unit.

miR-122a

Another interesting target microRNA is miR-122a. The sequence of miR-122a from positions three to eight, counting from the 5' end, is gagugu (see miRBase entry HGNC: MIRN122A). The corresponding DNA sequence is ctcaca.

Accordingly, a second aspect of the present invention relates to an oligonucleotide according to the invention, such as an oligonucleotide having a length of from 12 to 26 nucleotides having the DNA sequence from positions one to six, two to seven or three to eight, preferably from positions two to seven or three to eight, counting from the 3' end:

ctcaca, (SEQ ID NO 7)

wherein at least one, such as one, preferably at least two, such as two or three, DNA units in said sequence have been substituted by their corresponding LNA unit.

One embodiment relates to the miR-122a antagomir oligonucleotide as described above having a DNA sequence from positions one to seven, two to eight or three to nine, preferably from positions two to eight or three to nine, counting from the 3' end:

ctcacac,, (SEQ ID NO 73)

wherein at least one, such as one, preferably at least two, such as two, more preferably at least three, such as three or four, DNA units in said sequence have been substituted by their corresponding LNA unit.

In another embodiment, the oligonucleotide according to the present invention has a DNA sequence from positions one to eight, two to nine or three to ten, preferably from positions two to nine or three to ten, counting from the 3' end:

ctcacact,, (SEQ ID NO 74)

wherein at least one, such as one, preferably at least two, such as two, more preferably at least three, such as three or four, DNA units in said sequence have been substituted by their corresponding LNA unit.

In yet another embodiment, the oligonucleotide according to the present invention has a DNA sequence from positions one to nine, two to ten or three to eleven, preferably from positions two to ten or three to eleven, counting from the 3' end:

ctcacactg,, (SEQ ID NO 75)

wherein at least one, such as one, preferably at least two, such as two, more preferably at least three, such as three, even more preferably at least four, such as four or five, DNA units in said sequence have been substituted by their corresponding LNA unit.

miR-155

Another interesting target microRNA is miR-155. The sequence of miR-155 from positions three to eight, counting from the 5' end, is aaugcu (see miRBase entry HGNC: MIRN155). The corresponding DNA sequence is ttacga.

Accordingly, a third aspect of the invention relates to an oligonucleotide according to the invention, such as an oligonucleotide having a length of from 12 to 26 nucleotides having the DNA sequence from positions one to six, two to seven or three to eight, preferably from positions two to seven or three to eight, counting from the 3' end:

ttacga,, (SEQ ID NO 8)

wherein at least one, such as one, preferably at least two, such as two or three, DNA units in said sequence have been substituted by their corresponding LNA unit.

In one embodiment, the miR-155 antagomir oligonucleotide as described above has a DNA sequence from positions one to seven, two to eight or three to nine, preferably from positions two to eight or three to nine, counting from the 3' end:

ttacgat,, (SEQ ID NO 76)

wherein at least one, such as one, preferably at least two, such as two, more preferably at least three, such as three or four, DNA units in said sequence have been substituted by their corresponding LNA unit.

In another embodiment, the oligonucleotide according to the present invention has a DNA sequence from positions one to eight, two to nine or three to ten, preferably from positions two to nine or three to ten, counting from the 3' end:

ttacgatt,, (SEQ ID NO 77)

wherein at least one, such as one, preferably at least two, such as two, more preferably at least three, such as three or four, DNA units in said sequence have been substituted by their corresponding LNA unit.

In yet another embodiment, the oligonucleotide according to the present invention has a DNA sequence from positions one to nine, two to ten or three to eleven, preferably from positions two to ten or three to eleven, counting from the 3' end:

ttacgatta,, (SEQ ID NO 78)

wherein at least one, such as one, preferably at least two, such as two, more preferably at least three, such as three, even more preferably at least four, such as four or five, DNA units in said sequence have been substituted by their corresponding LNA unit.

miR-375

Yet another interesting target microRNA is miR-375. The sequence of miR-375 from positions three to eight, counting from the 5' end, is uguucg (see miRBase entry HGNC: MIRN375). The corresponding DNA sequence is acaagc.

Accordingly, a fourth aspect of the invention relates to an oligonucleotide according to the invention, such as an oligonucleotide having a length of from 12 to 26 nucleotides having the DNA sequence from positions one to six, two to seven or three to eight, preferably from positions two to seven or three to eight, counting from the 3' end:

acaagc,, (SEQ ID NO 9)

wherein at least one, such as one, preferably at least two, such as two or three, DNA units in said sequence have been substituted by their corresponding LNA unit.

In one embodiment, the miR-375 antagomir oligonucleotide as describe above has a DNA sequence from positions one to seven, two to eight or three to nine, preferably from positions two to eight or three to nine, counting from the 3' end:

acaagca,, (SEQ ID NO 79)

wherein at least one, such as one, preferably at least two, such as two, more preferably at least three, such as three or four, DNA units in said sequence have been substituted by their corresponding LNA unit.

In another embodiment, the oligonucleotide according to the present invention has a DNA sequence from positions one to eight, two to nine or three to ten, preferably from positions two to nine or three to ten, counting from the 3' end:

acaagcaa,, (SEQ ID NO 80)

wherein at least one, such as one, preferably at least two, such as two, more preferably at least three, such as three or four, DNA units in said sequence have been substituted by their corresponding LNA unit.

In yet another embodiment, the oligonucleotide according to the present invention has a DNA sequence from positions one to nine, two to ten or three to eleven, preferably from positions two to ten or three to eleven, counting from the 3' end:

acaagcaag, (SEQ ID NO 81)

wherein at least one, such as one, preferably at least two, such as two, more preferably at least three, such as three, even more preferably at least four, such as four or five, DNA units in said sequence have been substituted by their corresponding LNA unit.

Modification of Nucleotides in the Core Sequence

As mentioned above, in the core sequence of the oligonucleotides of the present invention at least one, such as one, preferably at least two, such as two or three, DNA units in said sequence have been substituted by their corresponding LNA unit. The present inventors have further found that inhibition of the target microRNAs may be further increased by making sure that two LNA units in said core sequence are separated by at least one DNA unit.

Accordingly, one embodiment of the invention relates to the oligonucleotide as described above, wherein at least two, such as two or three, DNA units from positions one to six, two to seven or three to eight, preferably from positions two to seven or three to eight, counting from the 3' end, have been substituted by their corresponding LNA unit and wherein the LNA units are separated by at least one DNA unit.

The present inventors have also found that inhibition of target microRNAs may be even further increased by making sure that two LNA units in the core sequence are separated by at most two DNA units. Accordingly, in one embodiment the present relates to the oligonucleotide as described above, wherein the number of consecutive DNA units from positions one to six, two to seven or three to eight, preferably from positions two to seven or three to eight, counting from the 3' end, is at most two.

Said findings apply to the core sequence per se, i.e. the finding applies to the positions of the oligonucleotides of the present invention corresponding to the core sequence. Hence, another embodiment relates to the oligonucleotide as described above, wherein at least two, such as two, three or four, DNA units from positions one to seven, two to eight or three to nine, preferably from positions two to eight or three to nine, counting from the 3' end, have been substituted by their corresponding LNA unit and wherein the LNA units are separated by at least one DNA unit. A further embodiment relates to the oligonucleotide as described above, wherein the number of consecutive DNA units from positions one to seven, two to eight or three to nine, preferably from positions two to eight or three to nine, counting from the 3' end, is at most two.

Yet another embodiment relates to the oligonucleotide as described above, wherein at least two, such as two, three or four, DNA units from positions one to eight, two to nine or three to ten, preferably from positions two to nine or three to ten, counting from the 3' end, have been substituted by their corresponding LNA unit and wherein the LNA units are separated by at least one DNA unit. Yet a further embodiment relates to the oligonucleotide as described above, wherein the number of consecutive DNA units from positions one to eight, two to nine or three to ten, preferably from positions two to nine or three to ten, counting from the 3' end, is at most two.

Still another embodiment relates to the oligonucleotide as described above, wherein at least two, such as two, three, four or five, DNA units from positions one to nine, two to ten or three to eleven, preferably from positions two to ten or three to eleven, counting from the 3' end, have been substituted by their corresponding LNA unit and wherein the LNA units are separated by at least one DNA unit. Still a further embodiment relates to the oligonucleotide as described above, wherein the number of consecutive DNA units from positions one to nine, two to ten or three to eleven, preferably from positions two to ten or three to eleven, counting from the 3' end, is at most two.

Modification of Nucleotides Outside the Core Sequence

As mentioned above, the nucleotides outside the core sequence may be both LNA units and/or non-LNA units. In one embodiment, the invention relates to the oligonucleotide as described above, wherein the number of LNA units outside the core sequence is at least one, such as one, two, three or four, and wherein said LNA units are separated by at least one non-LNA unit. In a further embodiment, the substitution pattern outside the core sequence is such that the number of consecutive non-LNA units outside the core sequence is at most two.

Modification of Nucleotides in Positions 3 to 8, Counting from the 3' End.

In the following embodiments which refer to the modification of nucleotides in positions 3 to 8, counting from the 3' end, the LNA units may be replaced with other nucleotide analogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In an interesting embodiment of the invention, the oligonucleotides of the invention are modified in positions 3 to 8, counting from the 3' end. The design of this sequence may be defined by the number of non-LNA units present or by the number of LNA units present. In a preferred embodiment of the former, at least one, such as one, of the nucleotides in positions three to eight, counting from the 3' end, is a non-LNA unit. In another embodiment, at least two, such as two, of the nucleotides in positions three to eight, counting from the 3' end, are non-LNA units. In yet another embodiment, at least three, such as three, of the nucleotides in positions three to eight, counting from the 3' end, are non-LNA units. In still another embodiment, at least four, such as four, of the nucleotides in positions three to eight, counting from the 3' end, are non-LNA units. In a further embodiment, at least five, such as five, of the nucleotides in positions three to eight, counting from the 3' end, are non-LNA units. In yet a further embodiment, all six nucleotides in positions three to eight, counting from the 3' end, are non-LNA units. In a preferred embodiment, said non-LNA unit is a DNA unit.

Alternatively defined, in a preferred embodiment, the oligonucleotide according to the invention comprises at least one LNA unit in positions three to eight, counting from the 3' end. In an embodiment thereof, the oligonucleotide according to the present invention comprises one LNA unit in positions three to eight, counting from the 3' end. The substitution pattern for the nucleotides in positions three to eight, counting from the 3' end, may be selected from the group consisting of Xxxxxx, xXxxxx, xxXxxx, xxxXxx, xxxxXx and xxxxxX, wherein "X" denotes an LNA unit and "x" denotes a non-LNA unit.

In another embodiment, the oligonucleotide according to the present invention comprises at least two LNA units in positions three to eight, counting from the 3' end. In an embodiment thereof, the oligonucleotide according to the present invention comprises two LNA units in positions three to eight, counting from the 3' end. The substitution pattern for the nucleotides in positions three to eight, counting from the 3' end, may be selected from the group consisting of XXxxxx, XxXxxx, XxxXxx, XxxxXx, XxxxxX, xXxxxx, xXxXxx, xXxxXx, xXxxxX, xxXXxx, xxXxXx, xxXxxX, xxxXXx, xxxXxX and xxxxXX, wherein "X" denotes an LNA unit and "x" denotes a non-LNA unit. In a preferred embodiment, the substitution pattern for the nucleotides in positions three to eight, counting from the 3' end, is selected from the group consisting of XxXxxx, XxxXxx, XxxxXx, XxxxxX, xXxXxx, xXxxXx, xXxxxX, xxXxXx, xxXxxX and xxxXxX, wherein "X" denotes an LNA unit and "x" denotes a non-LNA unit. In a more preferred embodiment, the substitution pattern for the nucleotides in positions three to eight, counting from the 3' end, is selected from the group consisting of xXxXxx, xXxxXx, xXxxxX, xxXxXx, xxXxxX and xxxXxX, wherein "X" denotes an LNA unit and "x" denotes a non-LNA unit. In an even more preferred embodiment, the substitution pattern for the nucleotides in positions three to eight, counting from the 3' end, is selected from the group consisting of xXxXxx, xXxxXx and xxXxXx, wherein "X" denotes an LNA unit and "x" denotes a non-LNA unit. In a most preferred embodiment, the substitution pattern for the nucleotides in positions three to eight, counting from the 3' end, is xXxXxx, wherein "X" denotes an LNA unit and "x" denotes a non-LNA unit.

In yet another embodiment, the oligonucleotide according to the present invention comprises at least three LNA units in positions three to eight, counting from the 3' end. In an embodiment thereof, the oligonucleotide according to the present invention comprises three LNA units in positions three to eight, counting from the 3' end. The substitution pattern for the nucleotides in positions three to eight, counting from the 3' end, may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In a preferred embodiment, the substitution pattern for the nucleotides in positions three to eight, counting from the 3' end, is selected from the group consisting of XXxxXxx, XXxxxXx, XXxxxxX, xXXxXx, xXXxxX, xxXXxX, XxxXXx, XxxxXX, XxxXXx, XxxxxX, xXxXXx, xXxxXX, xxXxXX, xXxXxX and XxXxXx, wherein "X" denotes an LNA unit and "x" denotes a non-LNA unit. In a more preferred embodiment, the substitution pattern for the nucleotides in positions three to eight, counting from the 3' end, is selected from the group consisting of xXXxXx, xXXxxX, xxXXxX, xXxXXx, xXxxXX, xxXxXX and xXxXxX, wherein "X" denotes an LNA unit and "x" denotes a non-LNA unit. In an even more preferred embodiment, the substitution pattern for the nucleotides in positions three to eight, counting from the 3' end, is xXxXxX or XxXxXx, wherein "X" denotes an LNA unit and "x" denotes a non-LNA unit. In a most preferred embodiment, the substitution pattern for the nucleotides, in positions three to eight, counting from the 3' end, is xXxXxX, wherein "X" denotes an LNA unit and "x" denotes a non-LNA unit.

In a further embodiment, the oligonucleotide according to the present invention comprises at least four LNA units in positions three to eight, counting from the 3' end. In an embodiment thereof, the oligonucleotide according to the present invention comprises four LNA units in positions three to eight, counting from the 3' end. The substitution pattern for the nucleotides in positions three to eight, counting from the 3' end, may be selected from the group consisting of xxXXXX, xXxXXX, xXXxXX, xXXXxX, xXXXXx, XxxXXX, XxXxXX, XxXXxX, XxXXXx, XXxxXX, XXxXxX, XXxXXx, XXXxxX, XXXxXx and XXXXxx, wherein "X" denotes an LNA unit and "x" denotes a non-LNA unit.

In yet a further embodiment, the oligonucleotide according to the present invention comprises at least five LNA units in positions three to eight, counting from the 3' end. In an embodiment thereof, the oligonucleotide according to the present invention comprises five LNA units in positions three to eight, counting from the 3' end. The substitution pattern for the nucleotides in positions three to eight, counting from the 3' end, may be selected from the group consisting of xXXXXX, XxXXXX, XXxXXX, XXXxXX, XXXXxX and XXXXXx, wherein "X" denotes an LNA unit and "x" denotes a non-LNA unit.

Preferably, the oligonucleotide according to the present invention comprises one or two LNA units in positions three to eight, counting from the 3' end. This is considered advantageous for the stability of the A-helix formed by the oligo:microRNA duplex, a duplex resembling an RNA:RNA duplex in structure.

In a preferred embodiment, said non-LNA unit is a DNA unit.

Variation of the Length of the Oligonucleotides

The length of the oligonucleotides of the invention need not match the length of the target microRNAs exactly. Indeed it is considered advantageous to have short oligonucleotides, such as between 10-17 or 10-16 nucleobases.

In one embodiment, the oligonucleotide according to the present has a length of from 8 to 24 nucleotides, such as 10 to 24, between 12 to 24 nucleotides, such as a length of 8, 9, 10, 11, 12, 13, 14, 15, 16, 17, 18, 19, 20, 21, 22, 23 or 24 nucleotides, preferably a length of from 10-22, such as between 12 to 22 nucleotides, such as a length of 10, 11, 12, 13, 14, 15, 16, 17, 18, 19, 20, 21 or 22 nucleotides, more preferably a length of from 10-20, such as between 12 to 20 nucleotides, such as a length of 10, 11, 12, 13, 14, 15, 16, 17, 18, 19 or 20 nucleotides, even more preferably a length of from 10 to 19, such as between 12 to 19 nucleotides, such as a length of 10, 11, 12, 13, 14, 15, 16, 17, 18 or 19 nucleotides, e.g. a length of from 10 to 18, such as between 12 to 18 nucleotides, such as a length of 10, 11, 12, 13, 14, 15, 16, 17 or 18 nucleotides, more preferably a length of from 10-17, such as from 12 to 17 nucleotides, such as a length of 10, 11, 12, 13, 14, 15, 16 or 17 nucleotides, most preferably a length of from 10 to 16, such as between 12 to 16 nucleotides, such as a length of 10, 11, 12, 13, 14, 15 or 16 nucleotides.

Modification of Nucleotides from Position 11, Counting from the 3' End, to the 5' End The substitution pattern for the nucleotides from position 11, counting from the 3' end, to the 5' end may include nucleotide analogue units (such as LNA) or it may not. In a preferred embodiment, the oligonucleotide according to the present invention comprises at least one nucleotide analogue unit (such as LNA), such as one nucleotide analogue unit, from position 11, counting from the 3' end, to the 5' end. In another preferred embodiment, the oligonucleotide according to the present invention comprises at least two nucleotide analogue units, such as LNA units, such as two nucleotide analogue units, from position 11, counting from the 3' end, to the 5' end.

In the following embodiments which refer to the modification of nucleotides in the nucleobases from position 11 to the 5' end of the oligonucleotide, the LNA units may be replaced with other nucleotide analogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In one embodiment, the oligonucleotide according to the present invention has the following substitution pattern, which is repeated from nucleotide eleven, counting from the 3' end, to the 5' end: xXxX or XxXx, wherein "X" denotes an LNA unit and "x" denotes a non-LNA unit. In another embodiment, the oligonucleotide according to the present invention has the following substitution pattern, which is repeated from nucleotide eleven, counting from the 3' end, to the 5' end: XxxXxx, xXxxXx or xxXxxX, wherein "X" denotes an LNA unit and "x" denotes a non-LNA unit. In yet another embodiment, the oligonucleotide according to the present invention has the following substitution pattern, which is repeated from nucleotide eleven, counting from the 3' end, to the 5' end: XxxxXxxx, xXxxxXxx, xxXxxxXx or xxxXxxxX, wherein "X" denotes an LNA unit and "x" denotes a non-LNA unit.

The specific substitution pattern for the nucleotides from position 11, counting from the 3' end, to the 5' end depends on the number of nucleotides in the oligonucleotides according to the present invention. In a preferred embodiment, the oligonucleotide according to the present invention contains 12 nucleotides and the substitution pattern for positions 11 to 12, counting from the 3' end, is selected from the group consisting of xX and Xx, wherein "X" denotes an LNA unit and "x" denotes a non-LNA unit. In a more preferred embodiment thereof, the substitution pattern for positions 11 to 12, counting from the 3' end, is xX, wherein "X" denotes an LNA unit and "x" denotes a non-LNA unit. Alternatively, no LNA units are present in positions 11 to 12, counting from the 3' end, i.e. the substitution pattern is xx.

In another preferred embodiment, the oligonucleotide according to the present invention contains 13 nucleotides and the substitution pattern for positions 11 to 13, counting from the 3' end, is selected from the group consisting of Xxx, xXx, xxX, XXx, XxX, xXX and XXX, wherein "X" denotes an LNA unit and "x" denotes a non-LNA unit. In a more preferred embodiment thereof, the substitution pattern for positions 11 to 13, counting from the 3' end, is selected from the group consisting of xXx, xxX and xXX, wherein "X" denotes an LNA unit and "x" denotes a non-LNA unit. In a most preferred embodiment thereof, the substitution pattern for positions 11 to 13, counting from the 3' end, is xxX, wherein "X" denotes an LNA unit and "x" denotes a non-LNA unit. Alternatively, no LNA units are present in positions 11 to 13, counting from the 3' end, i.e. the substitution pattern is xxx.

In yet another preferred embodiment, the oligonucleotide according to the present invention contains 14 nucleotides and the substitution pattern for positions 11 to 14, counting from the 3' end, is selected from the group consisting of Xxxx, xXxx, xxXx, xxxX, XXxx, XxXx, XxxX, xXXx, xXxX and xxXX, wherein "X" denotes an LNA unit and "x" denotes a non-LNA unit. In a preferred embodiment thereof, the substitution pattern for positions 11 to 14, counting from the 3' end, is selected from the group consisting of xXxx, xxXx, xxxX, xXxX and xxXX, wherein "X" denotes an LNA unit and "x" denotes a non-LNA unit. In a more preferred embodiment thereof, the substitution pattern for positions 11 to 14, counting from the 3' end, is xXxX, wherein "X" denotes an LNA unit and "x" denotes a non-LNA unit. Alternatively, no LNA units are present in positions 11 to 14, counting from the 3' end, i.e. the substitution pattern is xxxx In a further preferred embodiment, the oligonucleotide according to the present invention contains 15 nucleotides and the substitution pattern for positions 11 to 15, counting from the 3' end, is selected from the group consisting of Xxxxx, xXxxx, xxXxx, xxxXx, xxxxX, XXxxx, XxXxx, XxxXx, XxxxX, xXXxx, xXxXx, xXxxX, xxXXx, xxXxX, xxxXX and XxXxX, wherein "X" denotes an LNA unit and "x" denotes a non-LNA unit. In a preferred embodiment thereof, the substitution pattern for positions 11 to 15, counting from the 3' end, is selected from the group consisting of xxXxx, XxXxx, XxxXx, xXxXx, xXxxX and xxXxX, wherein "X" denotes an LNA unit and "x" denotes a non-LNA unit. In a more preferred embodiment thereof, the substitution pattern for positions 11 to 15, counting from the 3' end, is selected from the group consisting of xxXxx, xXxXx, xXxxX and xxXxX, wherein "X" denotes an LNA unit and "x" denotes a non-LNA unit. In an even more preferred embodiment thereof, the substitution pattern for positions 11 to 15, counting from the 3' end, is selected from the group consisting of xXxxX and xxXxX, wherein "X" denotes an LNA unit and "x" denotes a non-LNA unit. In a most preferred embodiment, the substitution pattern for positions 11 to 15, counting from the 3' end, is xxXxX, wherein "X" denotes an LNA unit and "x" denotes a non-LNA unit. Alternatively, no LNA units are present in positions 11 to 15, counting from the 3' end, i.e. the substitution pattern is xxxxx In yet a further preferred embodiment, the oligonucleotide according to the present invention contains 16 nucleotides and the substitution pattern for positions 11 to 16, counting from the 3' end, is selected from the group consisting of Xxxxxx, xXxxxx, xxXxxx, xxxXxx, xxxxXx, xxxxxX, XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX, xxxxXX, XXXxxx, XXxXxx, XXxxXx, XXxxxX, XxXXxx, XxXxXx, XxXxxX, XxxXXx, XxxXxX, XxxxXX, xXXXxx, xXXxXx, xXXxxX, xXxXXx, xXxXxX, xXxxXX, xxXXXx, xxXXxX, xxXxXX, xxxXXX and xxxXXX, wherein "X" denotes an LNA unit and "x" denotes a non-LNA unit. In a preferred embodiment thereof, the substitution pattern for positions 11 to 16, counting from the 3' end, is selected from the group consisting of XxxXxx, xXxXxx, xXxxXx, xxXxXx, xxXxxX, XxXxXx, XxXxxX, XxxXxX, xXxxXx, xXxxXX and xxXxXX, wherein "X" denotes an LNA unit and "x" denotes a non-LNA unit. In a more preferred embodiment thereof, the substitution pattern for positions 11 to 16, counting from the 3' end, is selected from the group consisting of xXxXxx, xXxxXx, xxXxXx, xxXxxX, xXxXxX, xXxxXX and xxXxXX, wherein "X" denotes an LNA unit and "x" denotes a non-LNA unit. In an even more preferred embodiment thereof, the substitution pattern for positions 11 to 16, counting from the 3' end, is selected from the group consisting of xxXxxX, xXxXxX, xXxxXX and xxXxXX, wherein "X" denotes an LNA unit and "x" denotes a non-LNA unit. In a still more preferred embodiment thereof, the substitution pattern for positions 11 to 16, counting from the 3' end, is selected from the group consisting of xxXxxX and xXxXxX, wherein "X" denotes an LNA unit and "x" denotes a non-LNA unit. In a most preferred embodiment thereof, the substitution pattern for positions 11 to 16, counting from the 3' end, is xxXxxX, wherein "X" denotes an LNA unit and "x" denotes a non-LNA unit. Alternatively, no LNA units are present in positions 11 to 16, counting from the 3' end, i.e. the substitution pattern is xxxxxx In a preferred embodiment of the invention, the oligonucleotide according to the present invention contains an LNA unit at the 5' end. In another preferred embodiment, the oligonucleotide according to the present invention contains an LNA unit at the first two positions, counting from the 5' end.

In a particularly preferred embodiment, the oligonucleotide according to the present invention contains 13 nucleotides and the substitution pattern, starting from the 3' end, is XXxXxXxxXXxxX, wherein "X" denotes an LNA unit and "x" denotes a non-LNA unit. The preferred sequence for this embodiment, starting from the 3' end, is CCtCaCacTGttA, wherein a capital letter denotes a nitrogenous base in an LNA-unit and a small letter denotes a nitrogenous base in a non-LNA unit.

In another particularly preferred embodiment, the oligonucleotide according to the present invention contains 15 nucleotides and the substitution pattern, starting from the 3' end, is XXxXxXxxXXxxXxX, wherein "X" denotes an LNA unit and "x" denotes a non-LNA unit. The preferred sequence for this embodiment, starting from the 3' end, is CCtCaCacTGttAcC, wherein a capital letter denotes a nitrogenous base in an LNA-unit and a small letter denotes a nitrogenous base in a non-LNA unit.

Modification of the Internucleoside Linkage Group

Typical internucleoside linkage groups in oligonucleotides are phosphate groups, but these may be replaced by internucleoside linkage groups differing from phosphate. In a further interesting embodiment of the invention, the oligonucleotide of the invention is modified in its internucleoside linkage group structure, i.e. the modified oligonucleotide comprises an internucleoside linkage group which differs from phosphate. Accordingly, in a preferred embodiment, the oligonucleotide according to the present invention comprises at least one Specific examples of internucleoside linkage groups which differ from phosphate ($-O-P(O)_2-O-$) include $-O-P(O,S)-O-$, $-O-P(S)_2-O-$, $-S-P(O)_2-O-$, $-S-P(O,S)-O-$, $-S-P(S)_2-O-$, $-O-P(O)_2-S-$, $-O-P(O,S)-S-$, $-S-P(O)_2-S-$, $-O-PO(R^H)-O-$, $O-PO(OCH_3)-O-$, $-O-PO(NR^H)-O-$, $-O-PO(OCH_2CH_2S-R)-O-$, $-O-PO(BH_3)-O-$, $-O-PO(NHR^H)-O-$, $-O-P(O)_2-NR^H-$, $-NR^H-P(O)_2-O-$, $-NR^H-CO-O-$, $-NR^H-CO-NR^H-$, $-O-CO-O-$, $-O-CO-NR^H-$, $-NR^H-CO-CH_2-$, $-O-CH_2-CO-NR^H-$, $-O-CH_2-CH_2-NR^H-$, $-CO-NR^H-CH_2-$, $-CH_2-NR^H-CO-$, $-O-CH_2-CH_2-S-$, $-S-CH_2-CH_2-O-$, $-S-CH_2-CH_2-S-$, $-CH_2-SO_2-CH_2-$, $-CH_2-CO-NR^H-$, $-O-CH_2-CH_2-NR^H-CO-$, $-CH_2-NCH_3-O-CH_2-$, where $R^H$ is hydrogen or $C_{1-4}$-alkyl.

When the internucleoside linkage group is modified, the internucleoside linkage group is preferably a phosphorothioate group ($-O-P(O,S)-O-$). In a preferred embodiment, all internucleoside linkage groups of the oligonucleotides according to the present invention are phosphorothioate.

Designs for Specific microRNAs

The following table provides examples of oligonucleotide according to the present invention, such as those used in pharmaceutical compositions, as compared to prior art type of molecules.

| | | SEQ ID |
|---|---|---|
| target: hsa-miR-122a MIMAT0000421 uggagugugacaaugguguuugu screened in HUH-7 cell line expressing miR-122 | | SEQ ID NO 1 |
| Oligo #, target microRNA, oligo sequence | Design | |
| 3962:miR-122 5'-ACAAacaccattgtcacacTCCA-3' | Full complement, gap | SEQ ID NO 11 |
| 3965:miR-122 5'-acaaacACCATTGTcacactcca-3' | Full complement, block | SEQ ID NO 12 |
| 3972:miR-122 5'-acAaaCacCatTgtCacActCca-3' | Full complement, LNA_3 | SEQ ID NO 13 |
| 3549 (3649):miR-122 5'-CcAttGTcaCaCtCC-3' | New design | SEQ ID NO 14 |
| 3975:miR-122 5'-CcAtTGTcaCACtCC-3' | Enhanced new design | SEQ ID NO 15 |
| 3975':miR-122 5'-ATTGTcACACtCC-3' | ED-13mer | SEQ ID NO 16 |
| 3975":miR-122 5'-TGTcACACtCC-3' | ED-11mer | SEQ ID NO 17 |
| 3549' (3649):miR-122 5' CC$^M$AT$^M$T$^M$GTC$^M$A$^M$CA$^M$CT$^M$CC-3' | New design-2'MOE | SEQ ID NO 18 |
| 3549" (3649):miR-122 5' CC$^F$AT$^F$T$^F$GTC$^F$A$^F$CA$^F$CT$^F$CC-3' | New design-2'Fluoro | SEQ ID NO 19 |
| target: hsa-miR-19b MIMAT0000074 ugugcaaauccaugcaaaacuga screened HeLa cell line expressing miR-19b | | SEQ ID NO 2 |
| Oligo #, target microRNA, oligo sequence | Design | |
| 3963:miR-19b 5'-TCAGttttgcatggatttgCACA-3' | Full complement, gap | SEQ ID NO 20 |
| 3967:miR-19b 5'-tcagttTTGCATGGatttgcaca-3' | Full complement, block | SEQ ID NO 21 |
| 3973:miR-19b 5'-tcAgtTttGcaTggAttTgcAca-3' | Full complement, LNA_3 | SEQ ID NO 22 |
| 3560:miR-19b 5'-TgCatGGatTtGcAC-3' | New design | SEQ ID NO 23 |
| 3976:miR-19b 5'-TgCaTGGatTTGcAC-3' | Enhanced new design | SEQ ID NO 24 |
| 3976':miR-19b 5'-CaTGGaTTTGcAC-3' | ED-13mer | SEQ ID NO 25 |

|  |  | SEQ ID |
|---|---|---|
| 3976":miR-19b 5'-TGGaTTTGcAC-3' | ED-11mer | SEQ ID NO 26 |
| 3560':miR-19b 5' TG$^M$CA$^M$T$^M$GGA$^M$T$^M$T$^M$TT$^M$GC$^M$AC-3' | New design-2'MOE | SEQ ID NO 27 |
| 3560":miR-19b 5'-TG$^F$CA$^F$T$^F$GGA$^F$T$^F$TT$^F$GC$^F$AC-3' | New design-2'MOE | SEQ ID NO 28 |
| target: hsa-miR-155 MIMAT0000646<br>uuaaugcuaaucgugauagggg<br>screen in 518A2 cell line expressing miR-155 |  | SEQ ID NO 3 |
| Oligo #, target microRNA, oligo sequence | Design |  |
| 3964:miR-155 5'-CCCCtatcacgattagcaTTAA-3' | Full complement, gap | SEQ ID NO 29 |
| 3968:miR-155 5'-ccccctaTCACGATTagcattaa-3' | Full complement, block | SEQ ID NO 30 |
| 3974:miR-155 5'-cCccTatCacGatTagCatTaa-3' | Full complement, LNA_3 | SEQ ID NO 31 |
| 3758:miR-155 5'-TcAcgATtaGcAtTA-3' | New design | SEQ ID NO 32 |
| 3818:miR-155 5'-TcAcGATtaGCAtTA-3' | Enhanced new design | SEQ ID NO 33 |
| 3818':miR-155 5'-ACGATtAGCAtTA-3' | ED-13mer | SEQ ID NO 34 |
| 3818":miR-155 5'-GATtAGCaTTA-3' | ED-11mer | SEQ ID NO 35 |
| 3758':miR-155 5'-TC$^M$AC$^M$G$^M$ATTA$^M$GC$^M$AT$^M$TA-3' | New design-2'MOE | SEQ ID NO 36 |
| 3758":miR-155 5'-TC$^F$AC$^F$G$^F$ATT$^F$A$^F$GC$^F$AT$^F$TA-3' | New design-2'Fluoro | SEQ ID NO 37 |
| target: hsa-miR-21 MIMAT0000076<br>uagcuuaucagacugauguuga |  | SEQ ID NO 4 |
| miR-21 5'-TCAAcatcagtctgataaGCTA-3' | Full complement, gap | SEQ ID NO 38 |
| miR-21 5'-tcaacaTCAGTCTGataagcta-3' | Full complement, block | SEQ ID NO 39 |
| miR-21 5'-tcAtcAtcAgtCtgAtaAGcTt-3' | Full complement, LNA_3 | SEQ ID NO 40 |
| miR-21 5'-TcAgtCTgaTaAgCT-3' | New design | SEQ ID NO 41 |
| miR-21 5'-TcAgTCTgaTAAgCT-3'- | Enhanced new design | SEQ ID NO 42 |
| miR-21 5'-AGTCTgATAAgCT-3'- | ED-13mer | SEQ ID NO 43 |
| miR-21 5'-TCTg<u>At</u>AAGCT-3'- | ED-11mer | SEQ ID NO 44 |
| miR-21 5'-TC$^M$AG$^M$T$^M$CTG$^M$A$^M$TA$^M$AG$^M$CT-3' | New design-2'MOE | SEQ ID NO 45 |
| miR-21 5'-TC$^F$AG$^F$T$^F$CTG$^F$A$^F$TA$^F$AG$^F$CT-3' | New design-2'Fluoro | SEQ ID NO 46 |
| target: hsa-miR-375 MIMAT0000728<br>uuuguucguucggcucgcguga |  | SEQ ID NO 5 |
| miR-375 5'-TCTCgcgtgccgttcgttCTTT-3' | Full complement, gap | SEQ ID NO 47 |
| miR-375 5'-tctcgcGTGCCGTTcgttcttt-3' | Full complement, block | SEQ ID NO 48 |
| miR-375 5'-tcTcgCgtGccGttCgtTctTt-3' | Full complement, LNA_3 | SEQ ID NO 49 |
| miR-375 5'-GtGccGTtcGtTcTT 3' | New design | SEQ ID NO 50 |
| miR-375 5'-GtGcCGTtcGTTcTT 3' | Enhanced new design | SEQ ID NO 51 |
| miR-375 5'-GCCGTtCgTTCTT 3' | ED-13mer | SEQ ID NO 52 |
| miR-375 5'-CGTTcGTTCTT 3' | ED-11mer | SEQ ID NO 53 |
| miR-375 5'-GT$^M$GC$^M$C$^M$G$^M$TT$^M$C$^M$GT$^M$TC$^M$TT 3' | New design-2'MOE | SEQ ID NO 54 |
| miR-375 5'-GT$^F$GC$^F$C$^F$G$^F$TT$^F$C$^F$GT$^F$TC$^F$TT 3' | New design-2'Fluoro | SEQ ID NO 55 |

Capital Letters without a superscript M or F, refer to LNA units. Lower case=DNA, except for lower case in bold=RNA. The LNA cytosines may optionally be methylated). Capital letters followed by a superscript M refer to 2'OME RNA units, Capital letters followed by a superscript F refer to 2'fluoro DNA units, lowercase letter refer to DNA. The above oligos may in one embodiment be entirely phosphorothioate, but other nucleobase linkages as herein described bay be used. In one embodiment the nucleobase linkages are all phosphodiester. It is considered that for use within the brain/spinal cord it is preferable to use phosphodiester linkages, for example for the use of antimiRs targeting miR21.

The oligonucleotides according to the invention may, in one embodiment, have a sequence of nucleobases 5'-3' selected form the group consisting of:

```
LdLddLLddLdLdLL   (New design)

LdLdLLLddLLLdLL   (Enhanced new design)

LMLMMLLMMLMLMLL   (New design-2'MOE)

LMLMLLLMMLLLMLL   (Enhanced new design-2'MOE)

LFLFFLLFFLFLFLL   (New design-2' Fluoro)

LFLFLLLFFLLLFLL   (Enhanced new design-2' Fluoro)

LddLddLddL(d)(d)(L)(d)(d)(L)(d)   'Every third' dLddLddLdd(L)(d)(d)(L)(d)(d)(L)   'Every third' ddLddLddLd(d)(L)(d)(d)(L)(d)(d)   'Every third'

LMMLMMLMML(M)(M)(L)(M)(M)(L)(M)   'Every third'

MLMMLMMLMM(L)(M)(M)(L)(M)(M)(L)   'Every third'

MMLMMLMMLM(M)(L)(M)(M)(L)(M)(M)   'Every third'

LFFLFFLFFL(F)(F)(L)(F)(F)(L)(F)   'Every third'

FLFFLFFLFF(L)(F)(F)(L)(F)(F)(L)   'Every third'

FFLFFLFFLF(F)(L)(F)(F)(L)(F)(F)   'Every third' dLdLdLdLdL(d)(L)(d)(L)(d)(L)(d)   'Every second'

LdLdLdLdLdL(d)(L)(d)(L)(d)(L)(d)(L)   'Every second'

MLMLMLMLML(M)(L)(M)(L)(M)(L)(M)   'Every second'

LMLMLMLMLML(M)(L)(M)(L)(M)(L)(M)(L)   'Every second'

FLFLFLFLFL(F)(L)(F)(L)(F)(L)(F)   'Every second'

LFLFLFLFLFL(F)(L)(F)(L)(F)(L)(F)(L)   'Every second'
```

Wherein L=LNA unit, d=DNA units, M=2'MOE RNA, F=2'Fluoro and residues in brackets are optional Specific examples of the oligonucleotides according to the present invention may be selected from the group consisting of tgCatGgaTttGcaCa (SEQ ID NO 82), tgCatGgaTttGcaC (SEQ ID NO 83), CatGgaTttGcaC (SEQ ID NO 84), tGcAtGgAtTtGcAc (SEQ ID NO 85), cAtGgAtTtGcAc (SEQ ID NO 86), CatGGatTtGcAC (SEQ ID NO 87), TgCatGGatTtGcAC (SEQ ID NO 88), TgCaTgGaTTtGcACa (SEQ ID NO 89), cCatTgtCacActCca (SEQ ID NO 90), cCatTgtAacTctCca (SEQ ID NO 91), ccAttGtcAcaCtcCa (SEQ ID NO 92), cCatTgtCacActCc (SEQ ID NO 93), atTgtCacActCc (SEQ ID NO 94), ccAttGtcAcaCtcC (SEQ ID NO 95), AttGtcAcaCtcC (SEQ ID NO 96), aTtGtCaCaCtCc (SEQ ID NO 97), AttGTcaCaCtCC (SEQ ID NO 98), CcAttGTcaCaCtCC (SEQ ID NO 99), CcaTtgTcacActcCa (SEQ ID NO 100), CCAttgtcacTCCa (SEQ ID NO 101), tCacGatTagCatTaa (SEQ ID NO 102), aTcaCgaTtaGcaTta (SEQ ID NO 103), TcAcGaTtAgCaTtAa (SEQ ID NO 104), AtcAcGaTtAgCaTta (SEQ ID NO 105), gAgcCgaAcgAacAa (SEQ ID NO 106), gcCgaAcgAacAa (SEQ ID NO 107), GaGcCgAaCgAaCaA (SEQ ID NO 108), and GcCgAaCgAaCaA (SEQ ID NO 109); wherein a lowercase letter identifies the nitrogenous base of a DNA unit and an uppercase letter identifies the nitrogenous base of an LNA unit, with uppercase C referring to $^{Me}C$.

It will be recognised that the design of LNA/DNA nucleobases in the above specific examples may be applied to other oligonucleotides according to the invention.

Conjugates

The invention also provides for conjugates comprising the oligonucleotide according to the invention.

In one embodiment of the invention the oligomeric compound is linked to ligands/conjugates, which may be used, e.g. to increase the cellular uptake of antisense oligonucleotides. This conjugation can take place at the terminal positions 5'/3'-OH but the ligands may also take place at the sugars and/or the bases. In particular, the growth factor to which the antisense oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like. The invention also provides for a conjugate comprising the compound according to the invention as herein described, and at least one non-nucleotide or non-polynucleotide moiety covalently attached to said compound. Therefore, in one embodiment where the compound of the invention consists of s specified nucleic acid, as herein disclosed, the compound may also comprise at least one non-nucleotide or non-polynucleotide moiety (e.g. not comprising one or more nucleotides or nucleotide analogues) covalently attached to said compound. The non-nucleobase moiety may for instance be or comprise a sterol such as cholesterol.

Therefore, it will be recognised that the oligonucleotide of the invention, such as the oligonucleotide used in pharmaceutical (therapeutic) formulations may comprise further non-nucleobase components, such as the conjugates herein defined.

The LNA unit

In a preferred embodiment, the LNA unit has the general chemical structure shown in Scheme 1 below:

Scheme 1

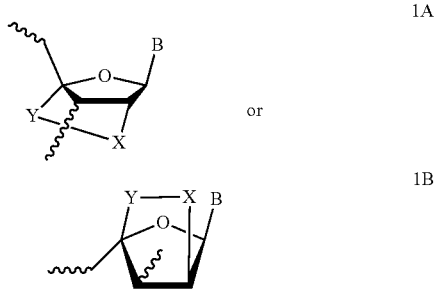

wherein

X is selected from the group consisting of O, S and $NR^H$, where $R^H$ is H or $C_{1-4}$-alkyl;

Y is $(-CH_2)_r$, where r is an integer of 1-4; and

B is a nitrogenous base.

In a preferred embodiment of the invention, r is 1 or 2, in particular 1, i.e. a preferred LNA unit has the chemical structure shown in Scheme 2 below:

Scheme 2

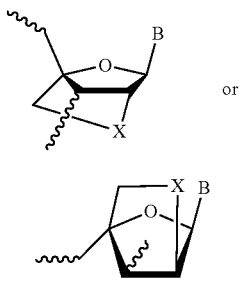

wherein X and B are as defined above.

In an interesting embodiment, the LNA units incorporated in the oligonucleotides of the invention are independently selected from the group consisting of thio-LNA units, amino-LNA units and oxy-LNA units.

Thus, the thio-LNA unit may have the chemical structure shown in Scheme 3 below:

Scheme 3

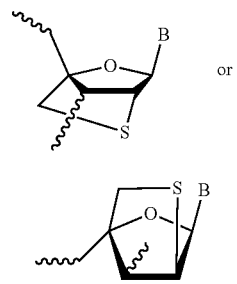

wherein B is as defined above.

Preferably, the thio-LNA unit is in its beta-D-form, i.e. having the structure shown in 3A above.

likewise, the amino-LNA unit may have the chemical structure shown in Scheme 4 below:

Scheme 4

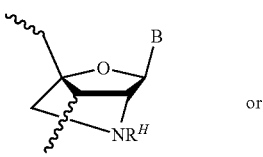

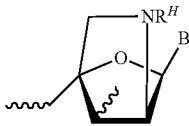

wherein B and $R^H$ are as defined above.

Preferably, the amino-LNA unit is in its beta-D-form, i.e. having the structure shown in 4A above.

The oxy-LNA unit may have the chemical structure shown in Scheme 5 below:

Scheme 5

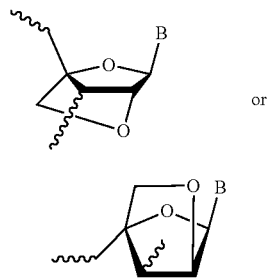

wherein B is as defined above.

Preferably, the oxy-LNA unit is in its beta-D-form, i.e. having the structure shown in 5A above.

As indicated above, B is a nitrogenous base which may be of natural or non-natural origin. Specific examples of nitrogenous bases include adenine (A), cytosine (C), 5-methylcytosine ($^{Me}C$), isocytosine, pseudoisocytosine, guanine (G), thymine (T), uracil (U), 5-bromouracil, 5-propynyluracil, 5-propyny-6,5-methyithiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

Terminal Groups

Specific examples of terminal groups include terminal groups selected from the group consisting of hydrogen, azido, halogen, cyano, nitro, hydroxy, Prot-O—, Act-O—, mercapto, Prot-S—, Act-S—, $C_{1-6}$-alkylthio, amino, Prot-N($R^H$)—, Act-N($R^H$)—, mono- or di($C_{1-6}$-alkyl)amino, optionally substituted $C_{1-6}$-alkoxy, optionally substituted $C_{1-6}$-alkyl, optionally substituted $C_{2-6}$-alkenyl, optionally substituted $C_{2-6}$-alkenyloxy, optionally substituted $C_{2-6}$-alkynyl, optionally substituted $C_{2-6}$-alkynyloxy, monophosphate including protected monophosphate, monothiophosphate including protected monothiophosphate, diphosphate including protected diphosphate, dithiophosphate including protected dithiophosphate, triphosphate including protected triphosphate, trithiophosphate including protected trithiophosphate, where Prot is a protection group for —OH, —SH and —NH($R^H$), and Act is an activation group for —OH, —SH, and —NH($R^H$), and $R^H$ is hydrogen or $C_{1-6}$-alkyl.

Examples of phosphate protection groups include S-acetylthioethyl (SATE) and S-pivaloylthioethyl (t-butyl-SATE).

Still further examples of terminal groups include DNA intercalators, photochemically active groups, thermochemically active groups, chelating groups, reporter groups, ligands, carboxy, sulphono, hydroxymethyl, Prot-O—

CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH and —NH(R$^H$), and Act is an activation group for —OH, —SH, and —NH(R$^H$), and R$^H$ is hydrogen or C$_{1-6}$-alkyl.

Examples of protection groups for —OH and —SH groups include substituted trityl, such as 4,4'-dimethoxytrityloxy (DMT), 4-monomethoxytrityloxy (MMT); trityloxy, optionally substituted 9-(9-phenyl)xanthenyloxy (pixyl), optionally substituted methoxytetrahydropyranyloxy (mthp); silyloxy, such as trimethylsilyloxy (TMS), trilsopropylsilyloxy (TIPS), tert-butyl-dimethylsilyloxy (TBDMS), triethylsilyloxy, phenyldimethylsilyloxy; tert-butylethers; acetals (including two hydroxy groups); acyloxy, such as acetyl or halogen-substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-Cl$_2$Bzl). Moreover, when Z or Z* is hydroxyl they may be protected by attachment to a solid support, optionally through a linker.

Examples of amine protection groups include fluorenylmethoxycarbonylamino (Fmoc), tert-butyloxycarbonylamino (BOC), trifluoroacetylamino, allyloxycarbonylamino (alloc, AOC), Z-benzyloxycarbonylamino (Cbz), substituted benzyloxycarbonylamino, such as 2-chloro benzyloxycarbonylamino (2-ClZ), monomethoxytritylamino (MMT), dimethoxytritylamino (DMT), phthaloylamino, and 9-(9-phenyl)xanthenylamino (pixyl).

The activation group preferably mediates couplings to other residues and/or nucleotide monomers and after the coupling has been completed the activation group is typically converted to an internucleoside linkage. Examples of such activation groups include optionally substituted O-phosphoramidite, optionally substituted O-phosphotriester, optionally substituted O-phosphodiester, optionally substituted H-phosphonate, and optionally substituted O-phosphonate. In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designates optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designates isopropyl. Accordingly, a particularly preferred phosphoramidite is N,N-diisopropyl-O-(2-cyanoethyl)phosphoramidite.

The most preferred terminal groups are hydroxy, mercapto and amino, in particular hydroxy.

Therapy and Pharmaceutical Compositions

As explained initially, the oligonucleotides of the invention will constitute suitable drugs with improved properties. The design of a potent and safe drug requires the fine-tuning of various parameters such as affinity/specificity, stability in biological fluids, cellular uptake, mode of action, pharmacokinetic properties and toxicity.

Accordingly, in a further aspect the present invention relates to a pharmaceutical composition comprising an oligonucleotide according to the invention and a pharmaceutically acceptable diluent, carrier or adjuvant. Preferably said carrier is saline of buffered saline.

In a still further aspect the present invention relates to an oligonucleotide according to the present invention for use as a medicament.

As will be understood, dosing is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides. Generally it can be estimated based on EC50s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

Pharmaceutical Compositions

As indicated above, the invention also relates to a pharmaceutical composition, which comprises at least one oligonucleotide of the invention as an active ingredient. It should be understood that the pharmaceutical composition according to the invention optionally comprises a pharmaceutical carrier, and that the pharmaceutical composition optionally comprises further compounds, such as chemotherapeutic compounds, anti-inflammatory compounds, antiviral compounds and/or immuno-modulating compounds.

The oligonucleotides of the invention can be used "as is" or in form of a variety of pharmaceutically acceptable salts. As used herein, the term "pharmaceutically acceptable salts" refers to salts that retain the desired biological activity of the herein-identified oligonucleotides and exhibit minimal undesired toxicological effects. Non-limiting examples of such salts can be formed with organic amino acid and base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine.

In one embodiment of the invention, the oligonucleotide may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) in Crooke, S. T. *Antisense research and Application*. Springer-Verlag, Berlin, Germany, vol. 131, pp. 103-140).

Pharmaceutically acceptable binding agents and adjuvants may comprise part of the formulated drug.

Examples of delivery methods for delivery of the therapeutic agents described herein, as well as details of pharmaceutical formulations, salts, may are well described elsewhere for example in U.S. provisional application 60/838,710 and 60/788,995, which are hereby incorporated by reference, and Danish applications, PA 2006 00615 which is also hereby incorporated by reference.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The compounds of the invention may also be conjugated to active drug substances, for example, aspirin, ibuprofen, a sulfa drug, an antidiabetic, an antibacterial or an antibiotic.

In another embodiment, compositions of the invention may contain one or more oligonucleotide compounds, targeted to a first microRNA and one or more additional oligonucleotide compounds targeted to a second microRNA target. Two or more combined compounds may be used together or sequentially.

The compounds disclosed herein are useful for a number of therapeutic applications as indicated above. In general, therapeutic methods of the invention include administration of a therapeutically effective amount of an oligonucleotide to a mammal, particularly a human. In a certain embodiment, the present invention provides pharmaceutical compositions containing (a) one or more compounds of the invention, and (b) one or more chemotherapeutic agents. When used with the compounds of the invention, such chemotherapeutic agents may be used individually, sequentially, or in combination with one or more other such chemotherapeutic agents or in combination with radiotherapy. All chemotherapeutic agents known to a person skilled in the art are here incorporated as combination treatments with compound according to the invention. Other active agents, such as anti-inflammatory drugs, including but not limited to nonsteroidal anti-inflammatory drugs and corticosteroids, antiviral drugs, and immuno-modulating drugs may also be combined in compositions of the invention. Two or more combined compounds may be used together or sequentially.

Examples of therapeutic indications which may be treated by the pharmaceutical compositions of the invention:

| microRNA | Possible medical indications |
| --- | --- |
| miR-21 | Glioblastoma, breast cancer |
| miR-122 | hypercholesterolemia, hepatitis C, hemochromatosis |
| miR-19b | lymphoma and other tumour types |
| miR-155 | lymphoma, breast and lung cancer |
| miR-375 | diabetes, metabolic disorders |
| miR-181 | myoblast differentiation, auto immune disorders |

Tumor suppressor gene tropomyosin 1 (TPM1) mRNA has been indicated as a target of miR-21. Myotrophin (mtpn) mRNA has been indicated as a target of miR 375.

In an even further aspect, the present invention relates to the use of an oligonucleotide according to the invention for the manufacture of a medicament for the treatment of a disease selected from the group consisting of: atherosclerosis, hypercholesterolemia and hyperlipidemia; cancer, glioblastoma, breast cancer, lymphoma, lung cancer; diabetes, metabolic disorders; myoblast differentiation; immune disorders.

The invention further refers to an oligonucleotides according to the invention for the use in the treatment of from a disease selected from the group consisting of: atherosclerosis, hypercholesterolemia and hyperlipidemia; cancer, glioblastoma, breast cancer, lymphoma, lung cancer; diabetes, metabolic disorders; myoblast differentiation; immune disorders.

The invention provides for a method of treating a subject suffering from a disease or condition selected from the group consisting of: atherosclerosis, hypercholesterolemia and hyperlipidemia; cancer, glioblastoma, breast cancer, lymphoma, lung cancer; diabetes, metabolic disorders; myoblast differentiation; immune disorders, the method comprising the step of administering an oligonucleotide or pharmaceutical composition of the invention to the subject in need thereof.
Cancer In an even further aspect, the present invention relates to the use of an oligonucleotide according to the invention or a conjugate thereof for the manufacture of a medicament for the treatment of cancer. In another aspect, the present invention concerns a method for treatment of, or prophylaxis against, cancer, said method comprising administering an oligonucleotide of the invention or a conjugate thereof, or a pharmaceutical composition of the invention to a patient in need thereof.

Such cancers may include lymphoreticular neoplasia, lymphoblastic leukemia, brain tumors, gastric tumors, plasmacytomas, multiple myeloma, leukemia, connective tissue tumors, lymphomas, and solid tumors.

In the use of a compound of the invention or a conjugate thereof for the manufacture of a medicament for the treatment of cancer, said cancer may suitably be in the form of a solid tumor. Analogously, in the method for treating cancer disclosed herein said cancer may suitably be in the form of a solid tumor.

Furthermore, said cancer is also suitably a carcinoma. The carcinoma is typically selected from the group consisting of malignant melanoma, basal cell carcinoma, ovarian carcinoma, breast carcinoma, non-small cell lung cancer, renal cell carcinoma, bladder carcinoma, recurrent superficial bladder cancer, stomach carcinoma, prostatic carcinoma, pancreatic carcinoma, lung carcinoma, cervical carcinoma, cervical dysplasia, laryngeal papillomatosis, colon carcinoma, colorectal carcinoma and carcinoid tumors. More typically, said carcinoma is selected from the group consisting of malignant melanoma, non-small cell lung cancer, breast carcinoma, colon carcinoma and renal cell carcinoma. The malignant melanoma is typically selected from the group consisting of superficial spreading melanoma, nodular melanoma, lentigo maligna melanoma, acral melagnoma, amelanotic melanoma and desmoplastic melanoma.

Alternatively, the cancer may suitably be a sarcoma. The sarcoma is typically in the form selected from the group consisting of osteosarcoma, Ewing's sarcoma, chondrosarcoma, malignant fibrous histiocytoma, fibrosarcoma and Kaposi's sarcoma.

Alternatively, the cancer may suitably be a glioma.

A further embodiment is directed to the use of an oligonucleotide according to the invention or a conjugate thereof for the manufacture of a medicament for the treatment of cancer, wherein said medicament further comprises a chemotherapeutic agent selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C(mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, the further chemotherapeutic agent is selected from taxanes such as Taxol, Paclitaxel or Docetaxel.

Similarly, the invention is further directed to the use of an oligonucleotide according to the invention or a conjugate thereof for the manufacture of a medicament for the treatment of cancer, wherein said treatment further comprises the administration of a further chemotherapeutic agent selected from the group consisting of adrenocorticosteroids, such as prednisone, dexamethasone or decadron; altretamine (hexalen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (paraplatin); carmustine (BCNU, BiCNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); idarubicin (idamycin); ifosfamide; IL-2 (proleukin, aldesleukin); interferon alpha (intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C(mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine). Suitably, said treatment further comprises the administration of a further chemotherapeutic agent selected from taxanes, such as Taxol, Paclitaxel or Docetaxel.

Alternatively stated, the invention is furthermore directed to a method for treating cancer, said method comprising administering an oligonucleotide of the invention or a conjugate thereof, or a pharmaceutical composition according to the invention to a patient in need thereof and further comprising the administration of a further chemotherapeutic agent. Said further administration may be such that the further chemotherapeutic agent is conjugated to the compound of the invention, is present in the pharmaceutical composition, or is administered in a separate formulation.

Infectious Diseases

It is contemplated that the compounds of the invention may be broadly applicable to a broad range of infectious diseases, such as diphtheria, tetanus, pertussis, polio, hepatitis B, hepatitis C, hemophilus influenza, measles, mumps, and *rubella*.

Hsa-miR122 is indicated in hepatitis C infection and as such oligonucleotides according to the invention which target miR-122 may be used to treat Hepatitis C infection.

Accordingly, in yet another aspect the present invention relates the use of an oligonucleotide according to the invention or a conjugate thereof for the manufacture of a medicament for the treatment of an infectious disease, as well as to a method for treating an infectious disease, said method comprising administering an oligonucleotide according to the invention or a conjugate thereof, or a pharmaceutical composition according to the invention to a patient in need thereof.

Inflammatory Diseases

The inflammatory response is an essential mechanism of defense of the organism against the attack of infectious agents, and it is also implicated in the pathogenesis of many acute and chronic diseases, including autoimmune disorders. In spite of being needed to fight pathogens, the effects of an inflammatory burst can be devastating. It is therefore often necessary to restrict the symptomotology of inflammation with the use of anti-inflammatory drugs. Inflammation is a complex process normally triggered by tissue injury that includes activation of a large array of enzymes, the increase in vascular permeability and extravasation of blood fluids, cell migration and release of chemical mediators, all aimed to both destroy and repair the injured tissue.

In yet another aspect, the present invention relates to the use of an oligonucleotide according to the invention or a conjugate thereof for the manufacture of a medicament for the treatment of an inflammatory disease, as well as to a method for treating an inflammatory disease, said method comprising administering an oligonucleotide according to the invention or a conjugate thereof, or a pharmaceutical composition according to the invention to a patient in need thereof.

In one preferred embodiment of the invention, the inflammatory disease is a rheumatic disease and/or a connective tissue diseases, such as rheumatoid arthritis, systemic lupus erythematosus (SLE) or Lupus, scleroderma, polymyositis, inflammatory bowel disease, dermatomyositis, ulcerative colitis, Crohn's disease, vasculitis, psoriatic arthritis, exfoliative psoriatic dermatitis, *pemphigus vulgaris* and Sjorgren's syndrome, in particular inflammatory bowel disease and Crohn's disease.

Alternatively, the inflammatory disease may be a non-rheumatic inflammation, like bursitis, synovitis, capsulitis, tendinitis and/or other inflammatory lesions of traumatic and/or sportive origin.

Metabolic Diseases

A metabolic disease is a disorder caused by the accumulation of chemicals produced naturally in the body. These diseases are usually serious, some even life threatening. Others may slow physical development or cause mental retardation. Most infants with these disorders, at first, show no obvious signs of disease. Proper screening at birth can often discover these problems. With early diagnosis and treatment, metabolic diseases can often be managed effectively.

In yet another aspect, the present invention relates to the use of an oligonucleotide according to the invention or a conjugate thereof for the manufacture of a medicament for the treatment of a metabolic disease, as well as to a method for treating a metabolic disease, said method comprising administering an oligonucleotide according to the invention or a conjugate thereof, or a pharmaceutical composition according to the invention to a patient in need thereof.

In one preferred embodiment of the invention, the metabolic disease is selected from the group consisting of Amyloidosis, Biotinidase, OMIM (Online Mendelian Inheritance in Man), Crigler Najjar Syndrome, Diabetes, Fabry Support & Information Group, Fatty acid Oxidation Disorders, Galactosemia, Glucose-6-Phosphate Dehydrogenase (G6PD) deficiency, Glutaric aciduria, International Organization of Glutaric Acidemia, Glutaric Acidemia Type I, Glutaric Acidemia, Type II, Glutaric Acidemia Type I, Glutaric Acidemia Type-II, F-HYPDRR-Familial Hypophosphatemia, Vitamin D Resistant Rickets, Krabbe Disease, Long chain 3 hydroxyacyl CoA dehydrogenase deficiency (LCHAD), Mannosidosis Group, Maple Syrup Urine Disease, Mitochondrial disorders, Mucopolysaccharidosis Syndromes: Niemann Pick, Organic acidemias, PKU, Pompe disease, Porphyria, Metabolic Syndrome, Hyperlipidemia and inherited lipid disorders, Trimethylaminuria: the fish malodor syndrome, and Urea cycle disorders.

Liver Disorders

In yet another aspect, the present invention relates to the use of an oligonucleotide according to the invention or a conjugate thereof for the manufacture of a medicament for the treatment of a liver disorder, as well as to a method for treating a liver disorder, said method comprising administering an oligonucleotide according to the invention or a conjugate thereof, or a pharmaceutical composition according to the invention to a patient in need thereof.

In one preferred embodiment of the invention, the liver disorder is selected from the group consisting of Biliary Atresia, Alegille Syndrome, Alpha-1 Antitrypsin, Tyrosinemia, Neonatal Hepatitis, and Wilson Disease.

Other Uses

The oligonucleotides of the present invention can be utilized for as research reagents for diagnostics, therapeutics and prophylaxis. In research, the oligonucleotide may be used to specifically inhibit the synthesis of target genes in cells and experimental animals thereby facilitating functional analysis of the target or an appraisal of its usefulness as a target for therapeutic intervention. In diagnostics the oligonucleotides may be used to detect and quantitate target expression in cell and tissues by Northern blotting, in-situ hybridisation or similar techniques. For therapeutics, an animal or a human, suspected of having a disease or disorder, which can be treated by modulating the expression of target is treated by administering the oligonucleotide compounds in accordance with this invention. Further provided are methods of treating an animal particular mouse and rat and treating a human, suspected of having or being prone to a disease or condition, associated with expression of target by administering a therapeutically or prophylactically effective amount of one or more of the oligonucleotide compounds or compositions of the invention.

Therapeutic Use of Oligonucleotides Targeting miR-122a

In the examples section, it is demonstrated that a LNA-antimiR™, such as SPC3372, targeting miR-122a reduces plasma cholesterol levels. Therefore, another aspect of the invention is use of the above described oligonucleotides targeting miR-122a as medicine.

Still another aspect of the invention is use of the above described oligonucleotides targeting miR-122a for the preparation of a medicament for treatment of increased plasma cholesterol levels. The skilled man will appreciate that increased plasma cholesterol levels is undesirable as it increases the risk of various conditions, e.g. atherosclerosis.

Still another aspect of the invention is use of the above described oligonucleotides targeting miR-122a for upregulating the mRNA levels of Nrdg3, Aldo A, Bckdk or CD320.

Further Embodiments

The Following Embodiments May be Combined with the Other Embodiments of the Invention as Described Herein 1. An oligonucleotide having a length of from 12 to 26 nucleotides having a core DNA sequence from positions two to seven or from positions three to eight, counting from the 3' end: acgttt, wherein at least one, such as one, preferably at least two, such as two or three, DNA units in said sequence have been substituted by their corresponding LNA unit; or a conjugate thereof.

2. An oligonucleotide having a length of from 12 to 26 nucleotides having a core DNA sequence from positions two to seven or from positions three to eight, counting from the 3' end: ctcaca, wherein at least one, such as one, preferably at least two, such as two or three, DNA units in said sequence have been substituted by their corresponding LNA unit; or a conjugate thereof.

3. An oligonucleotide having a length of from 12 to 26 nucleotides having a core DNA sequence from positions two to seven or from positions three to eight, counting from the 3' end: ttacga, wherein at least one, such as one, preferably at least two, such as two or three, DNA units in said sequence have been substituted by their corresponding LNA unit; or a conjugate thereof.

4. An oligonucleotide having a length of from 12 to 26 nucleotides having a core DNA sequence from positions two to seven or from positions three to eight, counting from the 3' end: acaagc; wherein at least one, such as one, preferably at least two, such as two or three, DNA units in said sequence have been substituted by their corresponding LNA unit; or a conjugate thereof.

5. The oligonucleotide according to any one of embodiments 1 to 4 or a conjugate thereof, wherein at least two, such as two or three, DNA units from positions one to six, two to seven or three to eight, counting from the 3' end, have been substituted by their corresponding LNA unit and wherein the LNA units are separated by at least one DNA unit.

6. The oligonucleotide according to embodiment 5 or a conjugate thereof, wherein the number of consecutive DNA units from positions one to six, two to seven or three to eight, counting from the 3' end, is at most two.

7. The oligonucleotide according to embodiment 6 or a conjugate thereof, wherein every second nucleotide from positions one to six, two to seven or three to eight, counting from the 3' end, is an LNA unit.

8. The oligonucleotide according to embodiment 6 or a conjugate thereof, wherein every third nucleotide from positions one to six, two to seven or three to eight, counting from the 3' end, is an LNA unit.

9. The oligonucleotide according to embodiment 6 or a conjugate thereof, wherein the substitution pattern for the nucleotides in positions one to six, two to seven or three to eight, counting from the 3' end, is selected from the group consisting of: xxXxxX, xxXxXx, xXxxXx, xXxXxx, XxxXxx, xXxXxX, XxXxXx, XxxXxX, and XxXxxX; wherein "X" denotes an LNA unit and "x" denotes a DNA unit.

10. The oligonucleotide according to embodiment 9 or a conjugate thereof, wherein the substitution pattern for the nucleotides in positions one to six, two to seven or three to eight, counting from the 3' end, is selected from the group consisting of xxXxxX, xXxxXx, XxxXxx, xXxXxX, and XxXxXx; wherein "X" denotes an LNA unit and "x" denotes a DNA unit.

11. The oligonucleotide according to embodiment 1 or a conjugate thereof having a DNA sequence from positions one to seven, two to eight or three to nine, counting from the 3' end: acgttta, wherein at least one, such as one, preferably at least two, such as two, more preferably at least three, such as three or four, DNA units in said sequence have been substituted by their corresponding LNA unit.

12. The oligonucleotide according to embodiment 2 or a conjugate thereof having a DNA sequence from positions one to seven, two to eight or three to nine, counting from the 3' end: ctcacac, wherein at least one, such as one, preferably at least two, such as two, more preferably at least three, such as three or four, DNA units in said sequence have been substituted by their corresponding LNA unit.

13. The oligonucleotide according to embodiment 3 or a conjugate thereof having a DNA sequence from positions one to seven, two to eight or three to nine, counting from the 3' end: ttacgat, wherein at least one, such as one, preferably at least two, such as two, more preferably at least three, such as three or four, DNA units in said sequence have been substituted by their corresponding LNA unit.

14. The oligonucleotide according to embodiment 4 or a conjugate thereof having a DNA sequence from positions one to seven, two to eight or three to nine, counting from the 3' end: acaagca, wherein at least one, such as one, preferably at least two, such as two, more preferably at least three, such as three or four, DNA units in said sequence have been substituted by their corresponding LNA unit.

15. The oligonucleotide according to any one of embodiments 11 to 14 or a conjugate thereof, wherein at least two, such as two, three or four, DNA units from positions one to seven, two to eight or three to nine, counting from the 3' end, have been substituted by their corresponding LNA unit and wherein the LNA units are separated by at least one DNA unit.

16. The oligonucleotide according to embodiment 15 or a conjugate thereof, wherein the number of consecutive DNA units from positions one to seven, two to eight or three to nine, counting from the 3' end, is at most two.

17. The oligonucleotide according to embodiment 16 or a conjugate thereof, wherein every second nucleotide from positions one to seven, two to eight or three to nine, counting from the 3' end, is an LNA unit.

18. The oligonucleotide according to embodiment 16 or a conjugate thereof, wherein every third nucleotide from positions one to seven, two to eight or three to nine, counting from the 3' end, is an LNA unit.

19. The oligonucleotide according to embodiment 16 or a conjugate thereof, wherein the substitution pattern for the nucleotides in positions one to seven, two to eight or three to nine, counting from the 3' end, is selected from the group consisting of xxXxxXx, xxXxXxx, xXxxXxx, xxXxXxX, xXxxXxX, xXxXxxX, xXxXxXx, XxxXxxX, XxxXxXx, XxXxxXx, XxXxXxx, and XxXxXxX; wherein "X" denotes an LNA unit and "x" denotes a DNA unit.

20. The oligonucleotide according to embodiment 19 or a conjugate thereof, wherein the substitution pattern for the nucleotides in positions one to seven, two to eight or three to nine, counting from the 3' end, is selected from the group consisting of xxXxxXx, xXxxXxx, XxxXxxX, xXxXxXx, XxXxXxX, and XxXxXxx; wherein "X" denotes an LNA unit and "x" denotes a DNA unit.

21. The oligonucleotide according to embodiment 11 or a conjugate thereof having a DNA sequence from positions one to eight, two to nine or three to ten, counting from the 3' end: acgtttag, wherein at least one, such as one, preferably at least two, such as two, more preferably at least three, such as three or four, DNA units in said sequence have been substituted by their corresponding LNA unit.

22. The oligonucleotide according to embodiment 12 or a conjugate thereof having a DNA sequence from positions one to eight, two to nine or three to ten, counting from the 3' end: ctcacact, wherein at least one, such as one, preferably at least two, such as two, more preferably at least three, such as three or four, DNA units in said sequence have been substituted by their corresponding LNA unit.

23. The oligonucleotide according to embodiment 13 or a conjugate thereof having a DNA sequence from positions one to eight, two to nine or three to ten, counting from the 3' end: ttacgatt, wherein at least one, such as one, preferably at least two, such as two, more preferably at least three, such as three or four, DNA units in said sequence have been substituted by their corresponding LNA unit.

24. The oligonucleotide according to embodiment 14 or a conjugate thereof having a DNA sequence from positions one to eight, two to nine or three to ten, counting from the 3' end: acaagcaa, wherein at least one, such as one, preferably at least two, such as two, more preferably at least three, such as three or four, DNA units in said sequence have been substituted by their corresponding LNA unit.

25. The oligonucleotide according to any one of embodiments 21 to 24 or a conjugate thereof, wherein at least two, such as two, three or four, DNA units from positions one to eight, two to nine or three to ten, counting from the 3' end, have been substituted by their corresponding LNA unit and wherein the LNA units are separated by at least one DNA unit.

26. The oligonucleotide according to embodiment 25 or a conjugate thereof, wherein the number of consecutive DNA units from positions one to eight, two to nine or three to ten, counting from the 3' end, is at most two.

27. The oligonucleotide according to embodiment 26 or a conjugate thereof, wherein every second nucleotide from positions one to eight, two to nine or three to ten, counting from the 3' end, is an LNA unit.

28. The oligonucleotide according to embodiment 26 or a conjugate thereof, wherein every third nucleotide from positions one to eight, two to nine or three to ten, counting from the 3' end, is an LNA unit.

29. The oligonucleotide according to embodiment 26 or a conjugate thereof, wherein the substitution pattern for the nucleotides in positions one to eight, two to nine or three to ten, counting from the 3' end, is selected from the group consisting of xxXxxXxx, xxXxxXxX, xxXxXxxX, xxXxXxXx, xXxxXxxX, xXxxXxXx, xXxXxxXx, xXxXxXxx, XxxXxxXx, XxxXxXxx, XxXxxXxx, xXxXxXxX, XxXxXxxX, XxXxXxxX, XxxXxXxX, and XxXxXxXx; wherein "X" denotes an LNA unit and "x" denotes a DNA unit.

30. The oligonucleotide according to embodiment 29 or a conjugate thereof, wherein the substitution pattern for the nucleotides in positions one to eight, two to nine or three to ten, counting from the 3' end, is selected from the group consisting of xXxXxxXx, xXxxXxxX, XxxXxxXx, xXxXxXxX, XxXxXxXx, and XxXxXxxX; wherein "X" denotes an LNA unit and "x" denotes a DNA unit.

31. The oligonucleotide according to embodiment 21 or a conjugate thereof having a DNA sequence from positions one to nine, two to ten or three to eleven, counting from the 3' end: acgtttagg, wherein at least one, such as one, preferably at least two, such as two, more preferably at least three, such as three, even more preferably at least four, such as four or five, DNA units in said sequence have been substituted by their corresponding LNA unit.

32. The oligonucleotide according to embodiment 22 or a conjugate thereof having a DNA sequence from positions one to nine, two to ten or three to eleven, counting from the 3' end: ctcacactg, wherein at least one, such as one, preferably at least two, such as two, more preferably at least three, such as three, even more preferably at least four, such as four or five, DNA units in said sequence have been substituted by their corresponding LNA unit.

33. The oligonucleotide according to embodiment 23 or a conjugate thereof having a DNA sequence from positions one to nine, two to ten or three to eleven, counting from the 3' end: ttacgatta, wherein at least one, such as one, preferably at least two, such as two, more preferably at least three, such as three, even more preferably at least four, such as four or five, DNA units in said sequence have been substituted by their corresponding LNA unit.

34. The oligonucleotide according to embodiment 24 or a conjugate thereof having a DNA sequence from positions one to nine, two to ten or three to eleven, counting from the 3' end: acaagcaag, wherein at least one, such as one, preferably at least two, such as two, more preferably at least three, such as three, even more preferably at least four, such as four or five, DNA units in said sequence have been substituted by their corresponding LNA unit.

35. The oligonucleotide according to any one of embodiments 21 to 24 or a conjugate thereof, wherein at least two, such as two, three, four or five, DNA units from positions one to nine, two to ten or three to eleven, counting from the 3' end, have been substituted by their corresponding LNA unit and wherein the LNA units are separated by at least one DNA unit.

36. The oligonucleotide according to embodiment 35 or a conjugate thereof, wherein the number of consecutive DNA units from positions one to nine, two to ten or three to eleven, counting from the 3' end, is at most two.

37. The oligonucleotide according to embodiment 36 or a conjugate thereof, wherein every second nucleotide from positions one to nine, two to ten or three to eleven, counting from the 3' end, is an LNA unit.

38. The oligonucleotide according to embodiment 36 or a conjugate thereof, wherein every third nucleotide from positions one to nine, two to ten or three to eleven, counting from the 3' end, is an LNA unit.

39. The oligonucleotide according to embodiment 36 or a conjugate thereof, wherein the substitution pattern for the nucleotides in positions one to nine, two to ten or three to eleven, counting from the 3' end, is selected from the group consisting of xxXxxXxxX, xxXxxXxXx, xxXxXxxXx, xxXxXxXxx, xXxxXxXxx, xXxxXxxXx, xXxxXxxXx, xXxXxxXxx, XxxXxxXxx, xxXxXxXxX, xXxxXxxXX, XxxXxxXxX,
xXxXxXxxX, XxxXxxXxX, XxxXxXxxX, XxXxxXxxX, XxxXxXxXx, XxXxxXxXx, XxXxXxxXx, XxXxXxXxx, and XxXxXxXxX; wherein "X" denotes an LNA unit and "x" denotes a DNA unit.

40. The oligonucleotide according to any of the preceding embodiments or a conjugate thereof, wherein said nucleotide has a length of from 12 to 24 nucleotides, such as a length of from 12 to 22 nucleotides, preferably a length of from 12 to 20 nucleotides, such as a length of from 12 to 19 nucleotides, more preferably a length of from 12 to 18 nucleotides, such as a length of from 12 to 17 nucleotides, even more preferably a length of from 12 to 16 nucleotides.

41. The oligonucleotide according to embodiment 1 having a sequence selected from the group consisting of tg$^{Me}$CatGgaTttGca$^{Me}$Ca, tg$^{Me}$CatGgaTttGca $^{Me}$C, $^{Me}$CatGgaTttGca$^{Me}$C, tGcAtGgAtTtGcAc, cAtGgAtTtGcAc, $^{Me}$CatGGatTtGcA$^{Me}$C, Tg$^{Me}$CatGGatTtGcA$^{Me}$C, and Tg$^{Me}$CaTgGaTttGcACa; wherein a lowercase letter identifies the nitrogenous base of a DNA unit and an uppercase letter identifies the nitrogenous base of an LNA unit; or a conjugate thereof. (SEQ IDs NO 82-89)

42. The oligonucleotide according to embodiment 2 having a sequence selected from the group consisting of c$^{Me}$CatTgtCacAct$^{Me}$Cca, c$^{Me}$CatTgtAacTct$^{Me}$Cca, ccAttGtcAca$^{Me}$Ctc$^{Me}$Ca, c$^{Me}$CatTgt$^{Me}$CacAct$^{Me}$Cc, atTgt$^{Me}$CacAct$^{Me}$Cc, ccAttGtcAca$^{Me}$Ctc$^{Me}$C, AttGtcAca$^{Me}$Ctc$^{Me}$C, aTtGt$^{Me}$CaCa$^{Me}$Ct$^{Me}$Cc, AttGTca$^{Me}$Ca$^{Me}$Ct$^{Me}$C$^{Me}$C, $^{Me}$CcAttGTca$^{Me}$Ca$^{Me}$Ct$^{Me}$C$^{Me}$C, $^{Me}$CcaTtgTcacActc$^{Me}$Ca, and $^{Me}$C$^{Me}$CAttgtcacacT$^{Me}$C$^{Me}$Ca; wherein a lowercase letter identifies the nitrogenous base of a DNA unit and an uppercase letter identifies the nitrogenous base of an LNA unit; or a conjugate thereof. (SEQ IDs NO 90-101)

43. The oligonucleotide according to embodiment 3 having a sequence selected from the group consisting of t$^{Me}$CacGatTag$^{Me}$CatTaa, aTca$^{Me}$CgaTtaGcaTta, TcAcGaTtAg$^{Me}$CaTtAa, AtcAcGaTtAg$^{Me}$CaTta; wherein a lowercase letter identifies the nitrogenous base of a DNA unit and an uppercase letter identifies the nitrogenous base of an LNA unit; or a conjugate thereof. (SEQ IDs NO 102-105).

44. The oligonucleotide according to embodiment 4 having a sequence selected from the group consisting of gAgc$^{Me}$CgaAcgAacAa, gc$^{Me}$CgaAcgAacAa, GaGc$^{Me}$CgAa$^{Me}$CgAa$^{Me}$CaA, and Gc$^{Me}$CgAa$^{Me}$CgAa$^{Me}$CaA; wherein a lowercase letter identifies the nitrogenous base of a DNA unit and an uppercase letter identifies the nitrogenous base of an LNA unit; or a conjugate thereof. (SEQ IDs NO 106-109).

45. The oligonucleotide according to any of the preceding embodiments or a conjugate thereof, wherein the oligonucleotide comprises at least one internucleoside linkage group which differs from phosphodiester.

46. The oligonucleotide according to embodiment 45 or a conjugate thereof, wherein said internucleoside linkage group, which differs from phosphodiester, is phosphorothioate.

47. The oligonucleotide according to embodiment 46 or a conjugate thereof, wherein all internucleoside linkage groups are phosphorothioate.

48. The oligonucleotide according to any of the preceding embodiments or a conjugate thereof, wherein said LNA units are independently selected from the group consisting of thio-LNA units, amino-LNA units and oxy-LNA units.

49. The oligonucleotide according to embodiment 48 or a conjugate thereof, wherein said LNA units are in the beta-D-form.

50. The oligonucleotide according to embodiment 48 or a conjugate thereof, wherein said LNA units are oxy-LNA units in the beta-D-form.

51. The oligonucleotide according to any of the preceding embodiments or a conjugate thereof for use as a medicament.

52. A pharmaceutical composition comprising an oligonucleotide according to any of embodiments 1-50 or a conjugate thereof and a pharmaceutically acceptable carrier.
53. The composition according to embodiment 52, wherein said carrier is saline or buffered saline.
54. Use of an oligonucleotide according to any of embodiments 1-50 or a conjugate thereof, or a composition according to embodiment 52 for the manufacture of a medicament for the treatment of cancer.
55. A method for the treatment of cancer, comprising the step of administering an oligonucleotide according to any of embodiment 1-50 or a conjugate thereof, or a composition according to embodiment 52.
56. Use of an oligonucleotide according to any of embodiments 1-50 or a conjugate thereof, or a composition according to embodiment 52 for the preparation of a medicament for treatment of increased plasma cholesterol levels.
57. Use of an oligonucleotide according to any of embodiments 1-50 or a conjugate thereof, or a composition according to embodiment 52 for upregulating the mRNA levels of Nrdg3, Aldo A, Bckdk or CD320.

EXPERIMENTAL

Example 1

Monomer Synthesis

The LNA monomer building blocks and derivatives thereof were prepared following published procedures and references cited therein, see, e.g. WO 03/095467 A1 and D. S. Pedersen, C. Rosenbohm, T. Koch (2002) Preparation of LNA Phosphoramidites, Synthesis 6, 802-808.

Example 2

Oligonucleotide Synthesis

Oligonucleotides were synthesized using the phosphoramidite approach on an Expedite 8900/MOSS synthesizer (Multiple Oligonucleotide synthesis System) at 1 μmol or 15 μmol scale. For larger scale synthesis an Äkta Oligo Pilot (GE Healthcare) was used. At the end of the synthesis (DMT-on), the oligonucleotides were cleaved from the solid support using aqueous ammonia for 1-2 hours at room temperature, and further deprotected for 4 hours at 65° C. The oligonucleotides were purified by reverse phase HPLC (RP-HPLC). After the removal of the DMT-group, the oligonucleotides were characterized by AE-HPLC, RP-HPLC, and CGE and the molecular mass was further confirmed by ESI-MS. See below for more details.
Preparation of the LNA-Solid Support:
Preparation of the LNA Succinyl Hemiester
5'-O-Dmt-3'-hydroxy-LNA monomer (500 mg), succinic anhydride (1.2 eq.) and DMAP (1.2 eq.) were dissolved in DCM (35 mL). The reaction was stirred at room temperature overnight. After extractions with $NaH_2PO_4$ 0.1 M pH 5.5 (2×) and brine (1×), the organic layer was further dried with anhydrous $Na_2SO_4$ filtered and evaporated. The hemiester derivative was obtained in 95% yield and was used without any further purification.
Preparation of the LNA-Support
The above prepared hemiester derivative (90 μmol) was dissolved in a minimum amount of DMF, DIEA and pyBOP (90 μmol) were added and mixed together for 1 min. This pre-activated mixture was combined with LCAA-CPG (500 Å, 80-120 mesh size, 300 mg) in a manual synthesizer and stirred. After 1.5 hours at room temperature, the support was filtered off and washed with DMF, DCM and MeOH. After drying, the loading was determined to be 57 μmol/g (see Tom Brown, Dorcas J. S. Brown. Modern machine-aided methods of oligodeoxyribonucleotide synthesis. In: F. Eckstein, editor. Oligonucleotides and Analogues A Practical Approach. Oxford: IRL Press, 1991: 13-14).
Elongation of the Oligonucleotide
The coupling of phosphoramidites (A(bz), G(ibu), 5-methyl-C(bz)) or T-β-cyanoethyl-phosphoramidite) is performed by using a solution of 0.1 M of the 5'-O-DMT-protected amidite in acetonitrile and DCI (4,5-dicyanoimidazole) in acetonitrile (0.25 M) as activator. The thiolation is carried out by using xanthane chloride (0.01 M in acetonitrile:pyridine 10%). The rest of the reagents are the ones typically used for oligonucleotide synthesis.
Purification by RP-HPLC:
Column: Xterra $RP_{18}$
Flow rate: 3 mL/min
Buffers: 0.1 M ammonium acetate pH 8 and acetonitrile
Abbreviations:
DMT: Dimethoxytrityl
DCI: 4,5-Dicyanoimidazole
DMAP: 4-Dimethylaminopyridine
DCM: Dichloromethane
DMF: Dimethylformamide
THF: Tetrahydrofurane
DIEA: N,N-diisopropylethylamine
PyBOP: Benzotriazole-1-yl-oxy-tris-pyrrolidino-phosphonium hexafluorophosphate
Bz: Benzoyl
Ibu: Isobutyryl Example 3

Design of the LNA Anti-miR Oligonucleotides and Melting Temperatures Target microRNA miR-122a:
    SEQ ID NO: 1
5'-uggagugugacaaugguguuugu-3' miR-122a 3' to 5':
    (SEQ ID NO: 1 reverse orientation)
3'-uguuugugguaacagugugaggu-5'

TABLE 1

| | | | | | | Tm |
|---|---|---|---|---|---|---|
| SEQ ID NO: | Oligo ID | SED ID | | Sequence: | | (° C.) |
| 2 | SPC3370 | XxxX design | SEQ ID 56 | 5'-cCatTgtCacActCca-3' | PS backbone | 75 |
| 3 | SPC3372 | XxxX design | SEQ ID 57 | 5'-ccAttGtcAcaCtcCa-3' | PS backbone | 69 |

TABLE 1 -continued

LNA anti-miR oligonucleotide sequences and $T_m$:

| SEQ ID NO: | Oligo ID | | SED ID | Sequence: | | Tm (° C.) |
|---|---|---|---|---|---|---|
| 4 | SPC3375 | Gapmer | SEQ ID 58 | 5'-CCAttgtcacacTCCa-3' | PS backbone | 69 |
| 5 | SPC3549 | 15-mer | SEQ ID 59 | 5'-CcAttGTcaCaCtCC-3' | PS backbone | 78 |
| 6 | SPC3550 | mismatch control | SEQ ID 60 | 5'-CcAtt<u>C</u>T<u>g</u>aC<u>c</u>Ct<u>A</u>C-3' | PS backbone | 32 |
| 7 | SPC3373 | mismatch control | SEQ ID 61 | 5'-ccAttGtc<u>T</u>ca<u>A</u>tcCa-3' | PS backbone | 46 |
| 8 | SPC3548 | 13-mer | SEQ ID 62 | 5'-AttGTcaCaCtCC-3' | PS backbone | | lower case: DNA,
uppercase: LNA (all LNA C were methylated),
underlined: mismatch The melting temperatures were assessed towards the mature miR-122a sequence, using a synthetic miR-122a RNA oligonucleotide with phosphorothioate linkaged.

The LNA anti-miR/miR-122a oligo duplex was diluted to 3 μM in 500 μl RNase free H$_2$O, which was then mixed with 500 μl 2× dimerization buffer (final oligo/duplex conc. 1.5 μM, 2× Tm buffer: 200 mM NaCl, 0.2 mM EDTA, 20 mM NaP, pH 7.0, DEPC treated to remove RNases). The mix was first heated to 95 degrees for 3 minutes, then allowed to cool at room temperature (RT) for 30 minutes.

Following RT incubation $T_m$ was measured on Lambda 40 UV/VIS Spectrophotometer with pettier temperature programmer PTP6 using PE Templab software (Perkin Elmer). The temperature was ramped up from 20° C. to 95° C. and then down again to 20° C., continuously recording absorption at 260 nm. First derivative and local maximums of both the melting and annealing was used to assess melting/annealing point ($T_m$), both should give similar/same $T_m$ values. For the first derivative 91 points was used to calculate the slope.

By substituting the antimir oligonucleotide and the complementary RNA molecule, the above assay can be used to determine the $T_m$ of other oligonucleotides such as the oligonucleotides according to the invention.

However, in one embodiment the $T_m$ may be made with a complementary DNA (phosphorothioate linkages) molecule. Typically the $T_m$ measured against a DNA complementary molecule is about 10° C. lower than the $T_m$ with an equivalent RNA complement. The $T_m$ measured using the DNA complement may therefore be used in cases where the duplex has a very high $T_m$.

Melting temperature ($T_m$) measurements:

| | $T_m$ |
|---|---|
| oligo to miR-122 RNA complement | |
| SPC3372 + miR-122a, RNA | 69° C. |
| SPC3648 + miR-122a, RNA | 74° C. |
| SPC3649 + miR-122a, RNA | 79° C. |
| oligo to DNA complement | |
| SPC3372 + 122R, DNA | 57° C. |
| SPC3649 + 122R, DNA | 66° C. |

It is recognised that for oligonucleotides with very high $T_m$, the above $T_m$ assays may be insufficient to determine the $T_m$. In such an instance the use of a phosphorothioated DNA complementary molecule may further lower the $T_m$.

The use of formamide is routine in the analysis of oligonucleotide hybridisation (see Hutton 1977, NAR 4 (10) 3537-3555). In the above assay the inclusion of 15% formamide typically lowers the $T_m$ by about 9° C., and the inclusion of 50% formamide typically lowers the $T_m$ by about 30° C. Using these ratios, it is therefore possible to determine the comparative $T_m$ of an oligonucleotide against its complementary RNA (phosphodiester) molecule, even when the $T_m$ of the duplex is, for example higher than 95° C. (in the absence of formamide).

For oligonucleotides with a very high $T_m$, an alternative method of determining the $T_m$, is to make titrations and run it out on a gel to see single strand versus duplex and by those concentrations and ratios determine Kd (the dissociation constant) which is related to deltaG and also $T_m$.

Example 4

Stability of LNA Oligonuclotides in Human or Rat Plasma

LNA oligonucleotide stability was tested in plasma from human or rats (it could also be mouse, monkey or dog plasma). In 45 μl plasma, 5 μl LNA oligonucleotide is added (at a final concentration of 20 μM). The LNA oligonucleotides are incubated in plasma for times ranging from 0 to 96 hours at 37° C. (the plasma is tested for nuclease activity up to 96 hours and shows no difference in nuclease cleavage-pattern).

At the indicated time the sample were snap frozen in liquid nitrogen. 2 μL (equals 40 μmol) LNA oligonucleotide in plasma was diluted by adding 15 μL of water and 3 μL 6× loading dye (Invitrogen). As marker a 10 bp ladder (Invitrogen, USA 10821-015) is used. To 1 μl ladder, 1 μl 6× loading and 4 μl water is added. The samples are mixed, heated to 65° C. for 10 min and loaded to a pre-run gel (16% acrylamide, 7 M UREA, 1×TBE, pre-run at 50 Watt for 1 h) and run at 50-60 Watt for 2½ hours. Subsequently, the gel is stained with 1×SyBR gold (molecular probes) in 1×TBE for 15 min. The bands were visualised using a phosphorimager from BioRad.

Example 5

In Vitro Model: Cell Culture

The effect of LNA oligonucleotides on target nucleic acid expression (amount) can be tested in any of a variety of cell types provided that the target nucleic acid is present at measurable levels. Target can be expressed endogenously or by transient or stable transfection of a nucleic acid encoding said nucleic acid.

The expression level of target nucleic acid can be routinely determined using, for example, Northern blot analysis (including microRNA northern), Quantitative PCR (including microRNA qPCR), Ribonuclease protection assays. The following cell types are provided for illustrative purposes, but other cell types can be routinely used, provided that the target is expressed in the cell type chosen.

Cells were cultured in the appropriate medium as described below and maintained at 37° C. at 95-98% humidity and 5% $CO_2$. Cells were routinely passaged 2-3 times weekly.

15PC3: The human prostate cancer cell line 15PC3 was kindly donated by Dr. F. Baas, Neurozintuigen Laboratory, AMC, The Netherlands and was cultured in DMEM (Sigma)+10% fetal bovine serum (FBS)+Glutamax I+gentamicin.

PC3: The human prostate cancer cell line PC3 was purchased from ATCC and was cultured in F12 Coon's with glutamine (Gibco)+10% FBS+gentamicin.

518A2: The human melanoma cancer cell line 518A2 was kindly donated by Dr. B. Jansen, Section of experimental Oncology, Molecular Pharmacology, Department of Clinical Pharmacology, University of Vienna and was cultured in DMEM (Sigma)+10% fetal bovine serum (FBS)+Glutamax I+gentamicin.

HeLa: The cervical carcinoma cell line HeLa was cultured in MEM (Sigma) containing 10% fetal bovine serum gentamicin at 37° C., 95% humidity and 5% $CO_2$.

MPC-11: The murine multiple myeloma cell line MPC-11 was purchased from ATCC and maintained in DMEM with 4 mM Glutamax+10% Horse Serum.

DU-145: The human prostate cancer cell line DU-145 was purchased from ATCC and maintained in RPMI with Glutamax+10% FBS.

RCC-4+/−VHL: The human renal cancer cell line RCC4 stably transfected with plasmid expressing VHL or empty plasmid was purchased from ECACC and maintained according to manufacturers instructions.

786-0: The human renal cell carcinoma cell line 786-0 was purchased from ATCC and maintained according to manufacturers instructions HUVEC: The human umbilical vein endothelial cell line HUVEC was purchased from Camcrex and maintained in EGM-2 medium.

K562: The human chronic myelogenous leukaemia cell line K562 was purchased from ECACC and maintained in RPMI with Glutamax+10% FBS. U87MG: The human glioblastoma cell line U87MG was purchased from ATCC and maintained according to the manufacturers instructions.

B16: The murine melanoma cell line B16 was purchased from ATCC and maintained according to the manufacturers instructions.

LNCap: The human prostate cancer cell line LNCap was purchased from ATCC and maintained in RPMI with Glutamax+10% FBS Huh-7: Human liver, epithelial like cultivated in Eagles MEM with 10% FBS, 2 mM Glutamax I, 1× non-essential amino acids, Gentamicin 25 µg/ml L428: (Deutsche Sammlung für Mikroorganismen (DSM, Braunschwieg, Germany)): Human B cell lymphoma maintained in RPMI 1640 supplemented with 10% FCS, L-glutamine and antibiotics.

L1236: (Deutsche Sammlung für Mikroorganismen (DSM, Braunschwieg, Germany)): Human B cell lymphoma maintained in RPMI 1640 supplemented with 10% FCS, L-glutamine and antibiotics.

Example 6

In Vitro Model: Treatment with LNA Anti-miR Antisense Oligonucleotide

The miR-122a expressing cell line Huh-7 was transfected with LNA anti-miRs at 1 and 100 nM concentrations according to optimized lipofectamine 2000 (LF2000, Invitrogen) protocol (as follows).

Huh-7 cells were cultivated in Eagles MEM with 10% FBS, 2 mM Glutamax I, 1× non-essential amino acids, Gentamicin 25 µg/ml. The cells were seeded in 6-well plates (300000 cells per well), in a total vol. of 2.5 ml the day before transfection. At the day of transfection a solution containing LF2000 diluted in Optimem (Invitrogen) was prepared (1.2 ml optimem+3.75 µl LF2000 per well, final 2.5 µg LF2000/ml, final tot vol 1.5 ml).

LNA Oligonucleotides (LNA anti-miRs) were also diluted in optimem. 285 µl optimem+15 µl LNA oligonucletide (10 µM oligonucleotide stock for final concentration 100 nM and 0.1 µM for final concentration 1 nM) Cells were washed once in optimem then the 1.2 ml optimem/LF2000 mix were added to each well. Cells were incubated 7 min at room temperature in the LF2000 mix where after the 300 µl oligonucleotide optimem solution was added.

Cell were further incubated for four hours with oligonucleotide and lipofectamine2000 (in regular cell incubator at 37° C., 5% CO2). After these four hours the medium/mix was removed and regular complete medium was added. Cells were allowed to grow for another 20 hours. Cells were harvested in Trizol (Invitrogen) 24 hours after transfection. RNA was extracted according to a standard Trizol protocol according to the manufacturer's instructions (Invitrogen), especially to retain the microRNA in the total RNA extraction.

Example 7

In Vitro and In Vivo Model: Analysis of Oligonucleotide Inhibition of miR Expression by microRNA Specific Quantitative PCR miR-122a levels in the RNA samples were assessed on an ABI 7500 Fast real-time PCR instrument (Applied Biosystems, USA) using a miR-122a specific qRT-PCR kit, mirVana (Ambion, USA) and miR-122a primers (Ambion, USA). The procedure was conducted according to the manufacturers protocol.

Results:

The miR-122a-specific new LNA anti-miR oligonucleotide design (ie SPC3349 (also referred to as SPC 3549)), was more efficient in inhibiting miR-122a at 1 nM compared to previous design models, including "every-third" and "gapmer" (SPC3370, SPC3372, SPC3375) motifs were at 100 nM. The mismatch control was not found to inhibit miR-122a (SPC3350). Results are shown in FIG. 1.

Example 8

Assessment of LNA Antago-Mir Knock-Down Specificity Using miRNA Microarray Expression Profiling A) RNA Labeling for miRNA Microarray Profiling Total RNA was extracted using Trizol reagent (Invitrogen) and 3' end labeled using T4 RNA ligase and Cy3- or Cy5-labeled RNA linker (5'-PO4-rUrUrU-Cy3/dT-3' or 5'-PO4-rUrUrU-Cy5/dT-3'). The labeling reactions contained 2-5 µg total RNA, 15 µM RNA linker, 50 mM Tris-HCl (pH 7.8), 10 mM MgCl2, 10 mM DTT, 1 mM ATP, 16% polyethylene glycol and 5 unit T4 RNA ligase (Ambion, USA) and were incubated at 30° C. for 2 hours followed by heat inactivation of the T4 RNA ligase at 80° C. for 5 minutes.

B) Microarray Hybridization and Post-Hybridization Washes

LNA-modified oligonucleotide capture probes comprising probes for all annotated miRNAs annotated from mouse (*Mus musculus*) and human (*Homo sapiens*) in the miRBase MicroRNA database Release 7.1 including a set of positive and negative control probes were purchased from Exiqon (Exiqon, Denmark) and used to print the microarrays for miRNA profiling. The capture probes contain a 5'-terminal C6-amino modified linker and were designed to have a Tm of 72° C. against complementary target miRNAs by adjustment of the LNA content and length of the capture probes. The capture probes were diluted to a final concentration of 10 µM in 150 mM sodium phosphate buffer (pH 8.5) and spotted in quadruplicate onto Codelink slides (Amersham Biosciences) using the MicroGrid II arrayer from BioRobotics at 45% humidity and at room temperature. Spotted slides were post-processed as recommended by the manufacturer.

Labeled RNA was hybridized to the LNA microarrays overnight at 65° C. in a hybridization mixture containing 4×SSC, 0.1% SDS, 1 µg/µl Herring Sperm DNA and 38% formamide. The hybridized slides were washed three times in 2×SSC, 0.025% SDS at 65° C., followed by three times in 0.08×SSC and finally three times in 0.4×SSC at room temperature.

C) Array Scanning, Image Analysis and Data Processing

The microarrays were scanned using the ArrayWorx scanner (Applied Precision, USA) according to the manufacturer's recommendations. The scanned images were imported into TIGR Spotfinder version 3.1 (Saeed et al., 2003) for the extraction of mean spot intensities and median local background intensities, excluding spots with intensities below median local background+4× standard deviations. Background-correlated intensities were normalized using variance stabilizing normalization package version 1.8.0 (Huber et al., 2002) for R (www.r-project.org). Intensities of replicate spots were averaged using Microsoft Excel. Probes displaying a coefficient of variance >100% were excluded from further data analysis.

Example 9

Detection of microRNAs by In Situ Hybridization
Detection of microRNAs in Formalin-Fixed Paraffin-Embedded Tissue Sections by In Situ Hybridization A) Preparation of the Formalin-Fixed, Paraffin-Embedded Sections for In Situ Hybridization Archival paraffin-embedded samples are retrieved and sectioned at 5 to 10 mm sections and mounted in positively-charged slides using floatation technique. Slides are stored at 4° C. until the in situ experiments are conducted.

B) In Situ Hybridization

Sections on slides are deparaffinized in xylene and then rehydrated through an ethanol dilution series (from 100% to 25%). Slides are submerged in DEPC-treated water and subject to HCl and 0.2% Glycine treatment, re-fixed in 4% paraformaldehyde and treated with acetic anhydride/triethanolamine; slides are rinsed in several washes of 1×PBS in-between treatments. Slides are pre-hybridized in hyb solution (50% formamide, 5×SSC, 500 mg/mL yeast tRNA, 1×Denhardt) at 50° C. for 30 min. Then, 3 µmol of a FITC-labeled LNA probe (Exiqon, Denmark) complementary to each selected miRNA is added to the hyb. solution and hybridized for one hour at a temperature 20-25° C. below the predicted Tm of the probe (typically between 45-55° C. depending on the miRNA sequence). After washes in 0.1× and 0.5×SCC at 65° C., a tyramide signal amplification reaction was carried out using the Genpoint Fluorescein (FITC) kit (DakoCytomation, Denmark) following the vendor's recommendations. Finally, slides are mounted with Prolong Gold solution. Fluorescence reaction is allowed to develop for 16-24 hr before documenting expression of the selected miRNA using an epifluorescence microscope.

Detection of microRNAs by Whole-Mount In Situ Hybridization of Zebrafish, *Xenopus* and Mouse Embryos.

All washing and incubation steps are performed in 2 ml eppendorf tubes. Embryos are fixed overnight at 4° C. in 4% paraformaldehyde in PBS and subsequently transferred through a graded series (25% MeOH in PBST (PBS containing 0.1% Tween-20), 50% MeOH in PBST, 75% MeOH in PBST) to 100% methanol and stored at −20° C. up to several months. At the first day of the in situ hybridization embryos are rehydrated by successive incubations for 5 min in 75% MeOH in PBST, 50% MeOH in PBST, 25% MeOH in PBST and 100% PBST (4×5 min).

Fish, mouse and *Xenopus* embryos are treated with proteinase K (10 µg/ml in PBST) for 45 min at 37° C., refixed for 20 min in 4% paraformaldehyde in PBS and washed 3×5 min with PBST. After a short wash in water, endogenous alkaline phosphatase activity is blocked by incubation of the embryos in 0.1 M tri-ethanolamine and 2.5% acetic anhydride for 10 min, followed by a short wash in water and 5×5 min washing in PBST. The embryos are then transferred to hybridization buffer (50% Formamide, 5×SSC, 0.1% Tween, 9.2 mM citric acid, 50 ug/ml heparin, 500 ug/ml yeast RNA) for 2-3 hour at the hybridization temperature. Hybridization is performed in fresh pre-heated hybridization buffer containing 10 nM of 3' DIG-labeled LNA probe (Roche Diagnostics) complementary to each selected miRNA. Post-hybridization washes are done at the hybridization temperature by successive incubations for 15 min in HM-(hybridization buffer without heparin and yeast RNA), 75% HM-/25% 2×SSCT (SSC containing 0.1% Tween-20), 50% HM-/50% 2×SSCT, 25% HM-/75% 2×SSCT, 100% 2×SSCT and 2×30 min in 0.2×SSCT.

Subsequently, embryos are transferred to PBST through successive incubations for 10 min in 75% 0.2×SSCT/25% PBST, 50° k 0.2×SSCT/50% PBST, 25% 0.2×SSCT/75% PBST and 100% PBST. After blocking for 1 hour in blocking buffer (2% sheep serum/2 mg:ml BSA in PBST), the embryos are incubated overnight at 4° C. in blocking buffer containing anti-DIG-AP FAB fragments (Roche, 1/2000). The next day, zebrafish embryos are washed 6×15 min in PBST, mouse and *X. tropicalis* embryos are washed 6×1 hour in TBST containing 2 mM levamisole and then for 2 days at 4° C. with regular refreshment of the wash buffer.

After the post-antibody washes, the embryos are washed 3×5 min in staining buffer (100 mM tris HCl pH9.5, 50 mM MgCl2, 100 mM NaCl, 0.1% tween 20). Staining was done in buffer supplied with 4.5 µl/ml NBT (Roche, 50 mg/ml stock) and 3.5 µl/ml BCIP (Roche, 50 mg/ml stock). The reaction is stopped with 1 mM EDTA in PBST and the embryos are stored at 4° C. The embryos are mounted in Murray's solution (2:1 benzylbenzoate:benzylalcohol) via an increasing methanol series (25% MeOH in PBST, 50% MeOH in PBST, 75% MeOH in PBST, 100% MeOH) prior to imaging.

Example 10

In Vitro Model: Isolation and Analysis of mRNA Expression (Total RNA Isolation and cDNA Synthesis for mRNA Analysis)

Total RNA was isolated either using RNeasy mini kit (Qiagen) or using the Trizol reagent (Invitrogen). For total RNA isolation using RNeasy mini kit (Qiagen), cells were washed with PBS, and Cell Lysis Buffer (RTL, Qiagen) supplemented with 1% mercaptoethanol was added directly to the wells. After a few minutes, the samples were processed according to manufacturer's instructions.

For in vivo analysis of mRNA expression tissue samples were first homogenised using a Retsch 300MM homogeniser and total RNA was isolated using the Trizol reagent or the RNeasy mini kit as described by the manufacturer.

First strand synthesis (cDNA from mRNA) was performed using either OmniScript Reverse Transcriptase kit or M-MLV Reverse transcriptase (essentially described by manufacturer (Ambion)) according to the manufacturer's instructions (Qiagen). When using OmniScript Reverse Transcriptase 0.5 µg total RNA each sample, was adjusted to 12 µl and mixed with 0.2 µl poly (dT)$_{12-18}$ (0.5 µg/µl) (Life Technologies), 2 µl dNTP mix (5 mM each), 2 µl 10×RT buffer, 0.5 µl RNAguard™ RNase Inhibitor (33 units/ml, Amersham) and 1 µl OmniScript Reverse Transcriptase followed by incubation at 37° C. for 60 min. and heat inactivation at 93° C. for 5 min.

When first strand synthesis was performed using random decamers and M-MLV-Reverse Transcriptase (essentially as described by manufacturer (Ambion)) 0.25 µg total RNA of each sample was adjusted to 10.8 µl in H$_2$O. 2 µl decamers and 2 µl dNTP mix (2.5 mM each) was added. Samples were heated to 70° C. for 3 min. and cooled immediately in ice water and added 3.25 µl of a mix containing (2 µl 10×RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C. The cDNA can further be used for mRNA quantification by for example Real-time quantitative PCR.

mRNA expression can be assayed in a variety of ways known in the art. For example, mRNA levels can be quantitated by, e.g., Northern blot analysis, competitive polymerase chain reaction (PCR), Ribonuclease protection assay (RPA) or real-time PCR. Real-time quantitative PCR is presently preferred. RNA analysis can be performed on total cellular RNA or mRNA.

Methods of RNA isolation and RNA analysis such as Northern blot analysis are routine in the art and is taught in, for example, Current Protocols in Molecular Biology, John Wiley and Sons.

Real-time quantitative (PCR) can be conveniently accomplished using the commercially available iQ Multi-Color Real Time PCR Detection System available from BioRAD. Real-time Quantitative PCR is a technique well-known in the art and is taught in for example Heid et al. Real time quantitative PCR, Genome Research (1996), 6: 986-994.

Example 11

LNA Oligonucleotide Uptake and Efficacy In Vivo

In vivo study: Six groups of animals (5 mice per group) were treated in the following manner. Group 1 animals were injected with 0.2 ml saline by i.v. on 3 successive days, Group 2 received 2.5 mg/kg SPC3372, Group 3 received 6.25 mg/kg, Group 4 received 12.5 mg/kg and Group 5 received 25 mg/kg, while Group 6 received 25 mg/kg SPC 3373 (mismatch LNA-antimiR™ oligonucleotide), all in the same manner. All doses were calculated from the Day 0 body weights of each animal.

Before dosing (Day 0) and 24 hour after last dose (Day 3), retro-orbital blood was collected in tubes containing EDTA and the plasma fraction harvested and stored frozen −80° C. for cholesterol analysis. At sacrifice livers were dissected and one portion was cut into 5 mm cubes and immersed in 5 volumes of ice-cold RNAlater. A second portion was snap frozen in liquid nitrogen and stored for cryo-sectioning.

Figure 5:
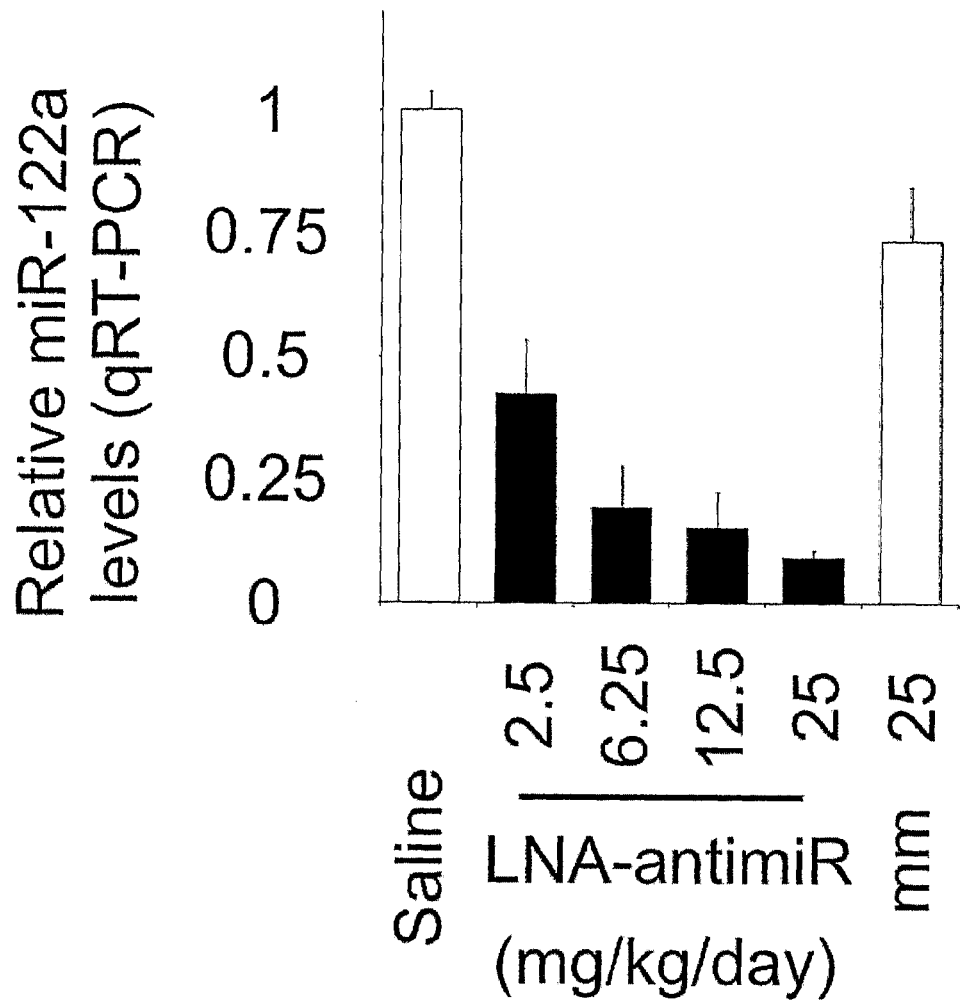
FIG. 5. Assessment of LNA-antimiR™-122a knock-down dose-response in vivo in mice livers using miR-122a real-time RT-PCR. Six groups of animals (5 mice per group) were treated in the following manner. Group 1 animals were injected with 0.2 ml saline by i.v. on 3 successive days, Group 2 received 2.5 mg/kg SPC3372, Group 3 received 6.25 mg/kg, Group 4 received 12.5 mg/kg and Group 5 received 25 mg/kg, while Group 6 received 25 mg/kg SPC 3373 (mismatch LNA-antimiR™ oligonucleotide), all in the same manner. The experiment was repeated (therefore n=10) and the combined results are shown.

Total RNA was extracted from liver samples as described above and analysed for miR-122a levels by microRNA specific QPCR. FIG. 5 demonstrates a clear dose-response obtained with SPC3372 with an IC50 at ca 3-5 mg/kg, whereas no miR-122a inhibition was detected using the mismatch LNA antago-mir SPC 3373 for miR-122a.

Example 12

LNA-antimiR-122a Dose-Response In Vivo in C57/BL/J Female Mice

In vivo study: Ten groups of animals (female C57/BL6; 3 mice per group) were treated in the following manner. Group 1 animals were injected with 0.2 ml saline by i.p. on day 0, day 2 and day 4. Groups 2-10 were dosed by i.p. with three different conc. (25 mg/kg, 5 mg/kg and 1 mg/kg) of either LNA antimiR-122a/SPC3372 (group 2-4), LNA antimir-122a/SPC3548 (group 5-7) or LNA antimir-122a/SPC3549 (group 8-10); the LNA antimir-122a sequences are given in the Table 1. All three LNA antimiR-122a oligonucleotides target the liver-specific miR-122a. The doses were calculated from the Day 0 body weights of each animal.

The animals were sacrificed 48 hours after last dose (Day 6), retro-orbital blood was collected in tubes containing EDTA and the plasma fraction harvested and stored frozen −80° C. for cholesterol analysis. At sacrifice livers were dissected and one portion was cut into 5 mm cubes and immersed in 5 volumes of ice-cold RNAlater. A second portion was snap frozen in liquid nitrogen and stored for cryo-sectioning.

Figure 2:
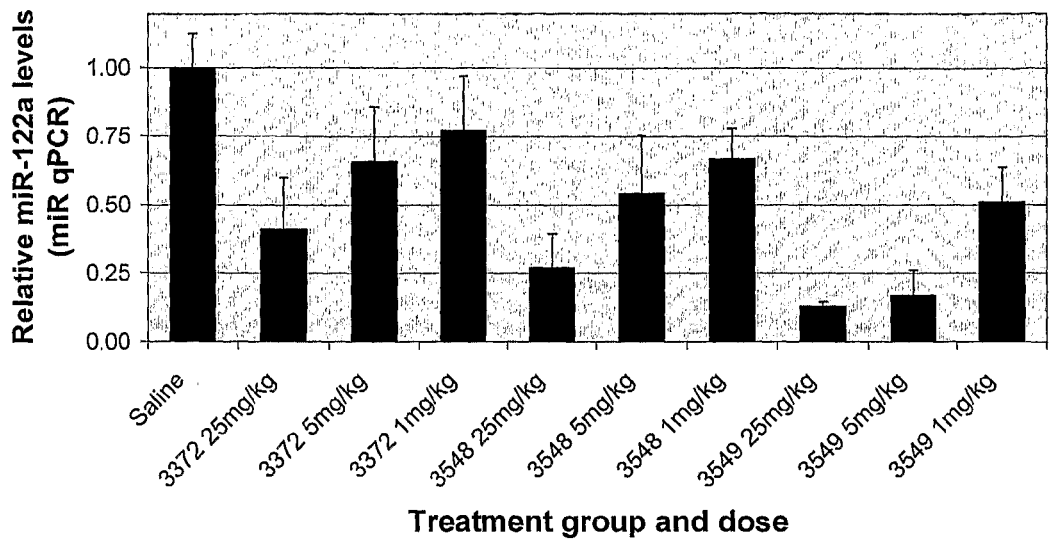
FIG. 2. Assessment of LNA anti-miR-122a knock-down dose-response for SPC3548 and SPC3549 in comparison with SPC3372 in vivo in mice livers using miR-122a real-time RT-PCR.

Total RNA was extracted from liver samples using Trizol reagent according to the manufacturer's recommendations (Invitrogen, USA) and analysed for miR-122a levels by microRNA-specific QPCR according to the manufacturer's recommendations (Ambion, USA). FIG. 2 demonstrates a clear dose-response obtained with all three LNA antimir-122a molecules (SPC3372, SPC3548, SPC3549). Both SPC3548 and SPC3549 show significantly improved efficacy in vivo in miR-122a silencing (as seen from the reduced miR-122a levels) compared to SPC3372, with SPC3549 being most potent ($IC_{50}$ ca 1 mg/kg).

Figure 2B:
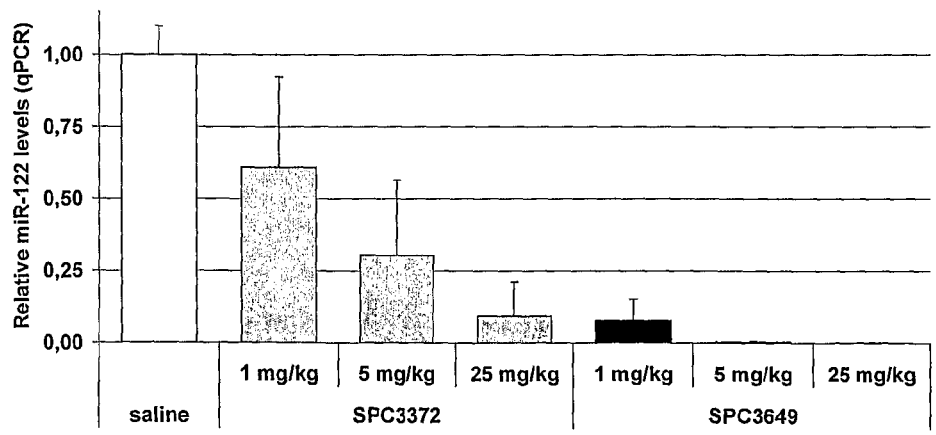
FIG. 2b miR-122 levels in the mouse liver after treatment with different LNA-antimiRs. The LNA-antimiR molecules SPC3372 and SPC3649 were administered into normal mice by three i.p. injections on every second day over a six-day-period at indicated doses and sacrificed 48 hours after last dose. Total RNA was extracted from the mice livers and miR-122 was measured by miR-122 specific qPCR.

The above example was repeated using SPC3372 and SPC 3649 using 5 mice per group and the data combined (total of eight mice per group) is shown in FIG. 2b.

Example 12a

Northern Blot

MicroRNA specific northern blot showing enhanced miR-122 blocking by SPC3649 compared to SPC3372 in LNA-antimiR treated mouse livers.

Oligos used in this example:

```
SPC3649: 5'-CcAttGTcaCaCtCC-3'     New design
(SEQ ID 59)

SPC3372: 5'-CcAttGtcAcaCtcCa-3'    Old design
(SEQ ID 57)
```

Figure 6:
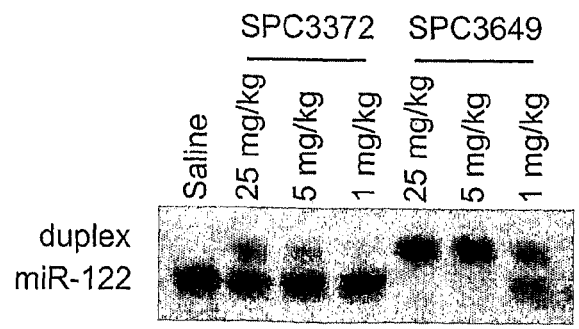
FIG. 6. Northern blot comparing SPC3649 with SPC3372. Total RNA from one mouse in each group were subjected to miR-122 specific northern blot. Mature miR-122 and the duplex (blocked microRNA) formed between the LNA-anti-miR and miR-122 is indicated.

We decided to assess the effect of SPC3649 on miR-122 miRNA levels in the livers of SPC3649-treated mice. The LNA-antimiRs SPC3649 and SPC3372 were administered into mice by three i.p. injections on every second day over a six-day-period at indicated doses followed by sacrificing the animals 48 hours after the last dose. Total RNA was extracted from the livers. miR-122 levels were assessed by microRNA specific northern blot (FIG. 6)

Treatment of normal mice with SPC3649 resulted in dramatically improved, dose-dependent reduction of miR-122. MicroRNA specific northern blot comparing SPC3649 with SPC3372 was performed (FIG. 6). SPC3649 completely blocked miR-122 at both 5 and 25 mg/kg as seen by the absence of mature single stranded miR-122 and only the presence of the duplex band between the LNA-antimiR and miR-122. Comparing duplex versus mature band on the northern blot SPC3649 seem equally efficient at 1 mg/kg as SPC3372 at 25 mg/kg.

Example 13

Assessment of Cholesterol Levels in Plasma in LNA Anti-miR122 Treated Mice

Total cholesterol level was measured in plasma using a colometric assay Cholesterol CP from ABX Pentra. Cholesterol was measured following enzymatic hydrolysis and oxidation (2.3). 21.5 µl water was added to 1.5 µl plasma. 250 µl reagent was added and within 5 min the cholesterol content measured at a wavelength of 540 nM. Measurements on each animal were made in duplicate. The sensitivity and linearity was tested with 2-fold diluted control compound (ABX Pentra N control). The cholesterol level was determined by subtraction of the background and presented relative to the cholesterol levels in plasma of saline treated mice.

FIG. 3 demonstrates a markedly lowered level of plasma cholesterol in the mice that received SPC3548 and SPC3549 compared to the saline control at Day 6.

Example 14

Assessment of miR-122a Target mRNA Levels in LNA antimiR-122a Treated Mice

Figure 4A:
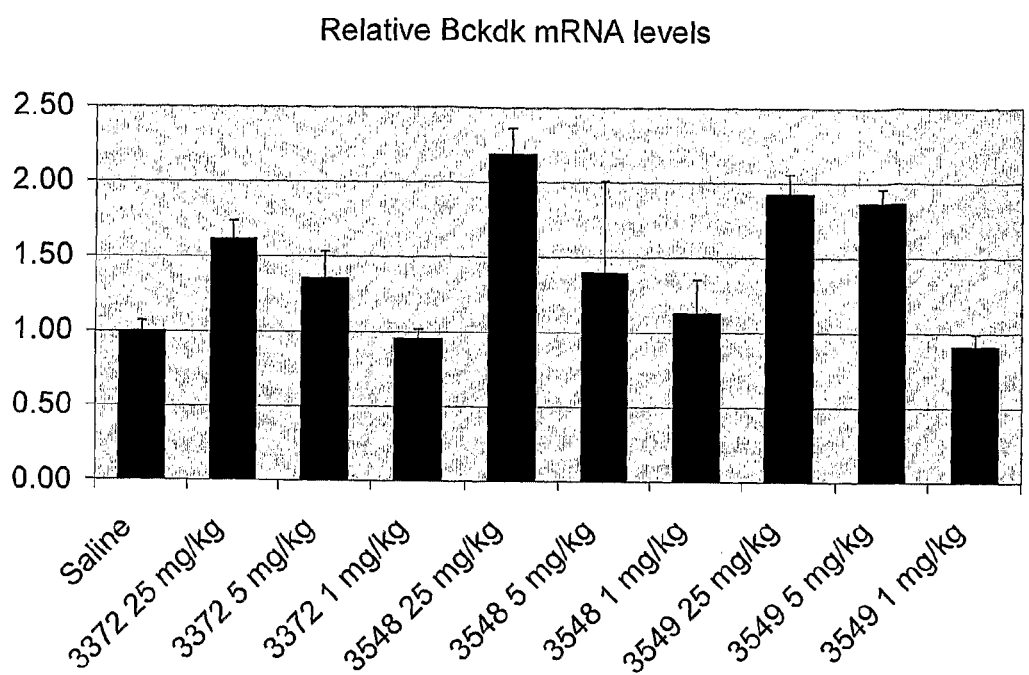
FIG. 4a. Assessment of relative Bckdk mRNA levels in LNA antimiR-122a treated mice in comparison with saline control mice using real-time quantitative RT-PCR.
Figure 4B:
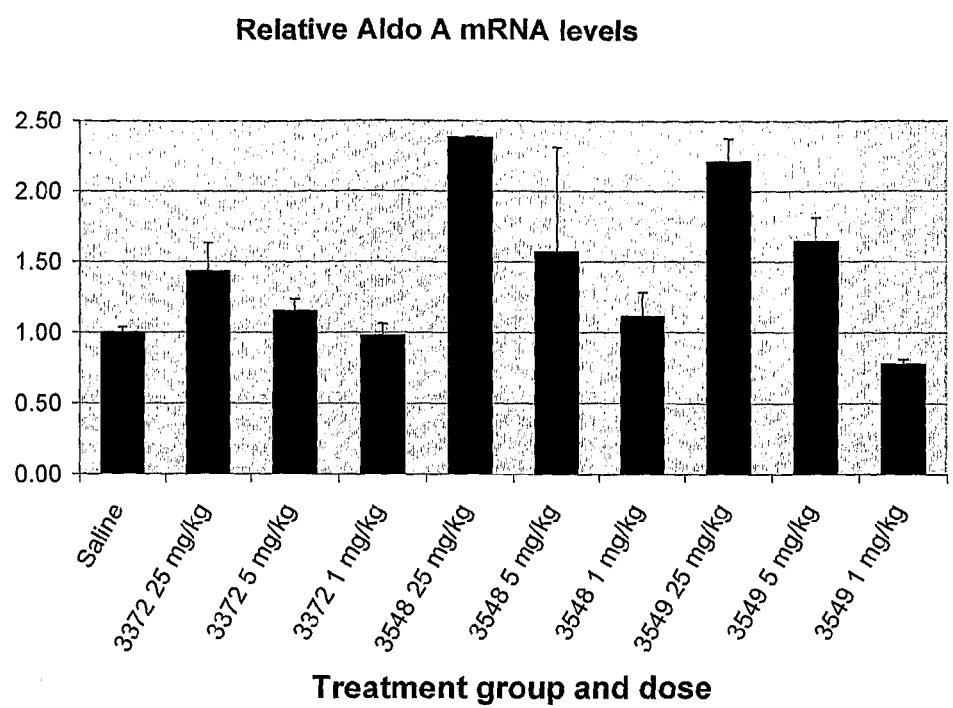
FIG. 4b. Assessment of relative aldolase A mRNA levels in LNA antimiR-122a treated mice in comparison with saline control mice using real-time quantitative RT-PCR.
Figure 4C:
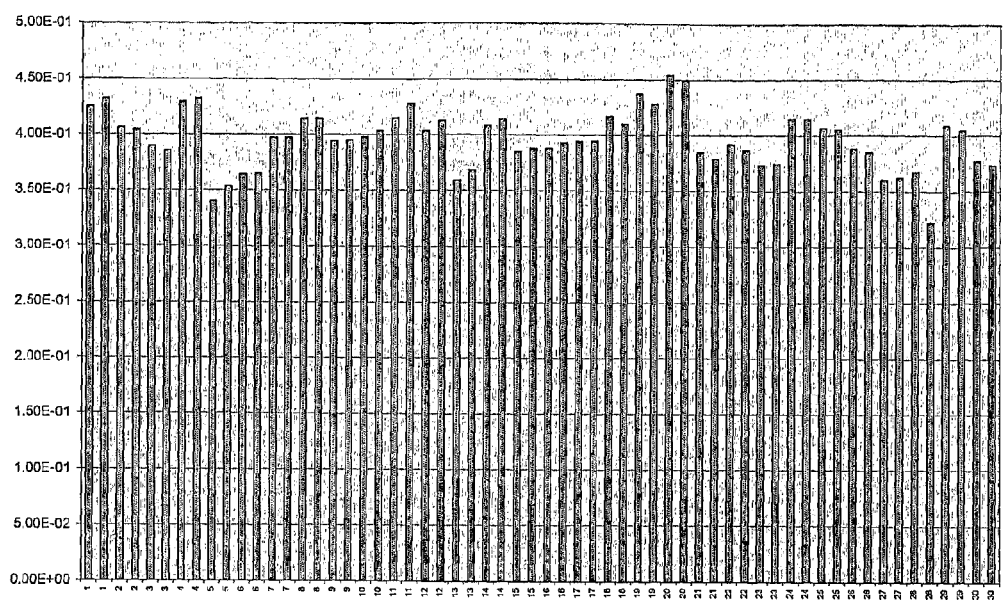
FIG. 4c. Assessment of GAPDH mRNA levels in LNA antimiR-122a treated mice (animals 4-30) in comparison with saline control mice (animals 1-3) using real-time quantitative RT-PCR.

The saline control and different LNA-antimiR-122a treated animals were sacrificed 48 hours after last dose (Day 6), and total RNA was extracted from liver samples as using Trizol reagent according to the manufacturer's recommendations (Invitrogen, USA). The mRNA levels were assessed by real-time quantitative RT-PCR for two miR-122a target genes, Bckdk (branched chain ketoacid dehydrogenase kinase, ENSMUSG00000030802) and aldolase A (aldoA, ENSMUSG00000030695), respectively, as well as for GAPDH as control, using Taqman assays according to the manufacturer's instructions (Applied biosystems, USA). FIGS. 4a and 4b demonstrate a clear dose-dependent upregulation of the two miR-122a target genes, Bckdk and AldoA, respectively, as a response to treatment with all three LNA antimiR-122a molecules (SPC3372, SPC3548, SPC3549). In contrast, the qPCR assays for GAPDH control did not reveal any differences in the GAPD mRNA levels in the LNA-antimiR-122a treated mice compared to the saline control animals (FIG. 4c). The Bckdk and AldoA mRNA levels were significantly higher in the SPC3548 and SPC3549 treated mice compared to the SPC3372 treated mice (FIGS. 4a and 4b), thereby demonstrating their improved in vivo efficacy.

Example 15

LNA Oligonucleotide Duration of Action In Vivo

In vivo study: Two groups of animals (21 mice per group) were treated in the following manner. Group 1 animals were injected with 0.2 ml saline by i.v. on 3 successive days, Group 2 received 25 mg/kg SPC3372 in the same manner. All doses were calculated from the Day 0 body weights of each animal.

After last dose (Day 3), 7 animals from each group were sacrificed on Day 9, Day 16 and Day 23, respectively. Prior to this, on each day, retro-orbital blood was collected in tubes containing EDTA and the plasma fraction harvested and stored frozen −80° C. for cholesterol analysis from each day. At sacrifice livers were dissected and one portion was cut into 5 mm cubes and immersed in 5 volumes of ice-cold RNAlater. A second portion was snap frozen in liquid nitrogen and stored for cryo-sectioning.

Figure 7:
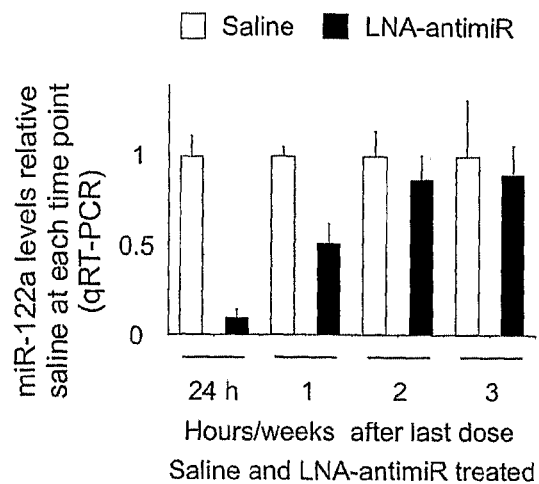
FIG. 7. Mice were treated with 25 mg/kg/day LNA-anti-miR or saline for three consecutive days and sacrificed 1, 2 or 3 weeks after last dose. Included are also the values from the animals sacrificed 24 hours after last dose (example 11 "old design"). miR-122 levels were assessed by qPCR and normalized to the mean of the saline group at each individual time point. Included are also the values from the animals sacrificed 24 hours after last dose (shown mean and SD, n=7, 24 h n=10). Sacrifice day 9, 16 or 23 corresponds to sacrifice 1, 2 or 3 weeks after last dose.).

Total RNA was extracted from liver samples as described above and analysed for miR-122a levels by microRNA specific QPCR. FIG. 7 (Sacrifice day 9, 16 or 23 correspond to sacrifice 1, 2 or 3 weeks after last dose) demonstrates a two-fold inhibition in the mice that received SPC3372 compared to the saline control, and this inhibition could still be detected at Day 16, while by Day 23 the mi122a levels approached those of the saline group.

Example 16

LNA Oligonucleotide Duration of Action In Vivo

In vivo study: Two groups of animals (21 mice per group) were treated in the following manner. Group 1 animals were injected with 0.2 ml saline by i.v. on 3 successive days, Group 2 received 25 mg/kg SPC3372 in the same manner. All doses were calculated from the Day 0 body weights of each animal.

After last dose (Day 3), 7 animals from each group were sacrificed on Day 9, Day 16 and Day 23, respectively. Prior to this, on each day, retro-orbital blood was collected in tubes containing EDTA and the plasma fraction harvested and stored frozen −80° C. for cholesterol analysis from each day. At sacrifice livers were dissected and one portion was cut into 5 mm cubes and immersed in 5 volumes of ice-cold RNAlater. A second portion was snap frozen in liquid nitrogen and stored for cryo-sectioning.

Figure 8:
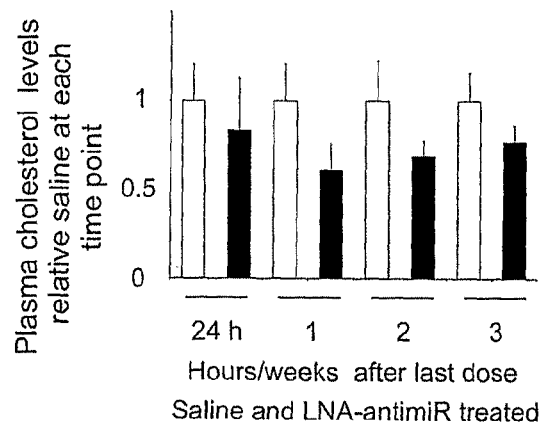
FIG. 8. Mice were treated with 25 mg/kg/day LNA-antimiR or saline for three consecutive days and sacrificed 1, 2 or 3 weeks after last dose. Included are also the values from the animals sacrificed 24 hours after last dose (example 11 "old design"). Plasma cholesterol was measured and normalized to the saline group at each time point (shown mean and SD, n=7, 24 h n=10).

Total RNA was extracted from liver samples as described above and analysed for miR-122a levels by microRNA specific QPCR. FIG. 8 demonstrates a two-fold inhibition in the mice that received SPC3372 compared to the saline control, and this inhibition could still be detected at Day 16, while by Day 23 the miR-122a levels approached those of the saline group.

As to examples 17-22, the following procedures apply:

NMRI mice were administered intravenously with SPC3372 using daily doses ranging from 2.5 to 25 mg/kg for three consecutive days. Animals were sacrificed 24 hours, 1, 2 or 3 weeks after last dose. Livers were harvested divided into pieces and submerged in RNAlater (Ambion) or snap-frozen. RNA was extracted with Trizol reagent according to the manufacturer's instructions (Invitrogen) from the RNAlater tissue, except that the precipitated RNA was washed in 80% ethanol and not vortexed. The RNA was used for mRNA TaqMan qPCR according to manufacturer (Applied biosystems) or northern blot (see below). The snap-frozen pieces were cryo-sectioned for in situ hybridizations.

Further, as to FIGS. 9-14, SPC3372 is designated LNA-antimiR and SPC3373 (the mismatch control) is designated "mm" instead of using the SPC number.

Example 17

Dose Dependent miR-122a Target mRNA Induction by SPC3372 Inhibition of miR-122a

Figure 9:
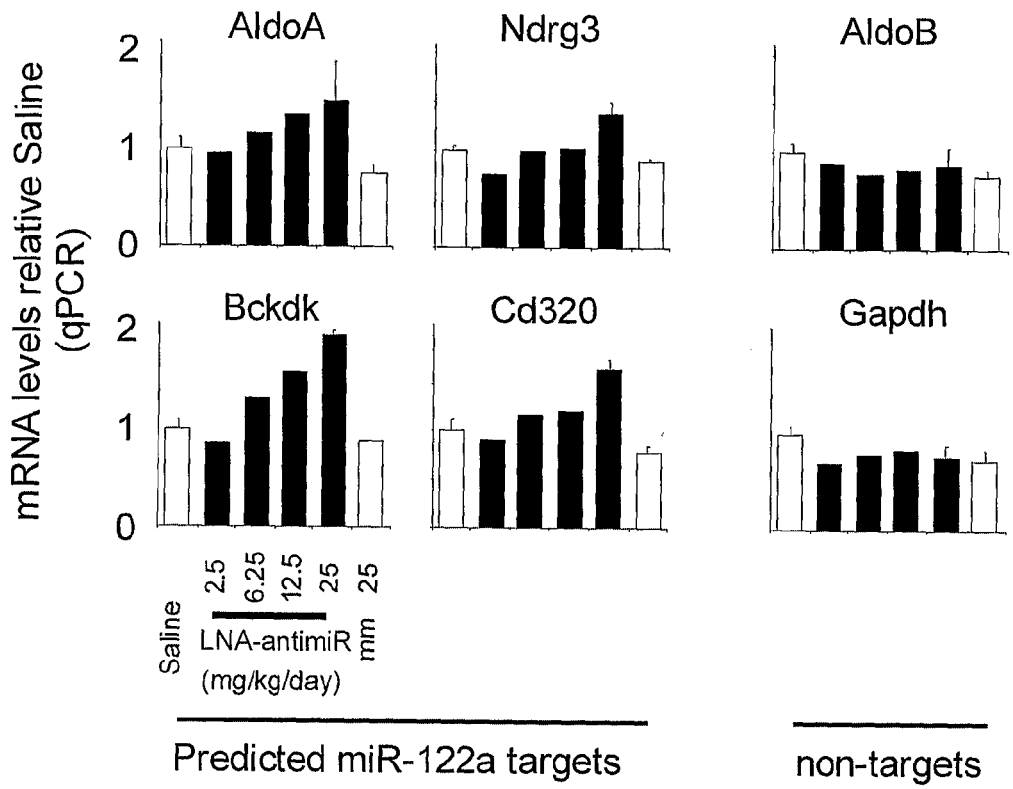
FIG. 9. Dose dependent miR-122a target mRNA induction by SPC3372 inhibition of miR-122a. Mice were treated with different SPC3372 doses for three consecutive days, as described above and sacrificed 24 hours after last dose. Total RNA extracted from liver was subjected to qPCR. Genes with predicted miR-122 target site and observed to be upregulated by microarray analysis were investigated for dose-dependent induction by increasing SPC3372 doses using qPCR. Total liver RNA from 2 to 3 mice per group sacrificed 24 hours after last dose were subjected to qPCR for the indicated genes. Shown in FIG. 9 is mRNA levels relative to Saline group, n=2-3 (2.5-12.5 mg/kg/day: n=2, no SD). Shown is also the mismatch control (mm, SPC3373).

Mice were treated with different SPC3372 doses for three consecutive days, as described above and sacrificed 24 hours after last dose. Total RNA extracted from liver was subjected to qPCR. Genes with predicted miR-122 target site and observed to be upregulated by microarray analysis were investigated for dose-dependent induction by increasing SPC3372 doses using qPCR. Total liver RNA from 2 to 3 mice per group sacrificed 24 hours after last dose were subjected to qPCR for the indicated genes. Shown in FIG. 9 is mRNA levels relative to Saline group, n=2-3 (2.5-12.5 mg/kg/day: n=2, no SD). Shown is also the mismatch control (mm, SPC3373).

Assayed genes: Nrdg3 Aldo A, Bckdk, CD320 with predicted miR-122 target site. Aldo B and Gapdh do not have a predicted miR-122a target site.

A clear dose-dependent induction was seen of the miR-122a target genes after treatment with different doses of SPC3372.

Example 18

Transient Induction of miR-122a Target mRNAs Following SPC3372 Treatment

NMRI female mice were treated with 25 mg/kg/day SPC3372 along with saline control for three consecutive days and sacrificed 1, 2 or 3 weeks after last dose, respectively. RNA was extracted from livers and mRNA levels of predicted miR-122a target mRNAs, selected by microarray data were investigated by qPCR. Three animals from each group were analysed.

Assayed genes: Nrdg3 Aldo A, Bckdk, CD320 with predicted miR-122 target site. Gapdh does not have a predicted miR-122a target site.

Figure 10:
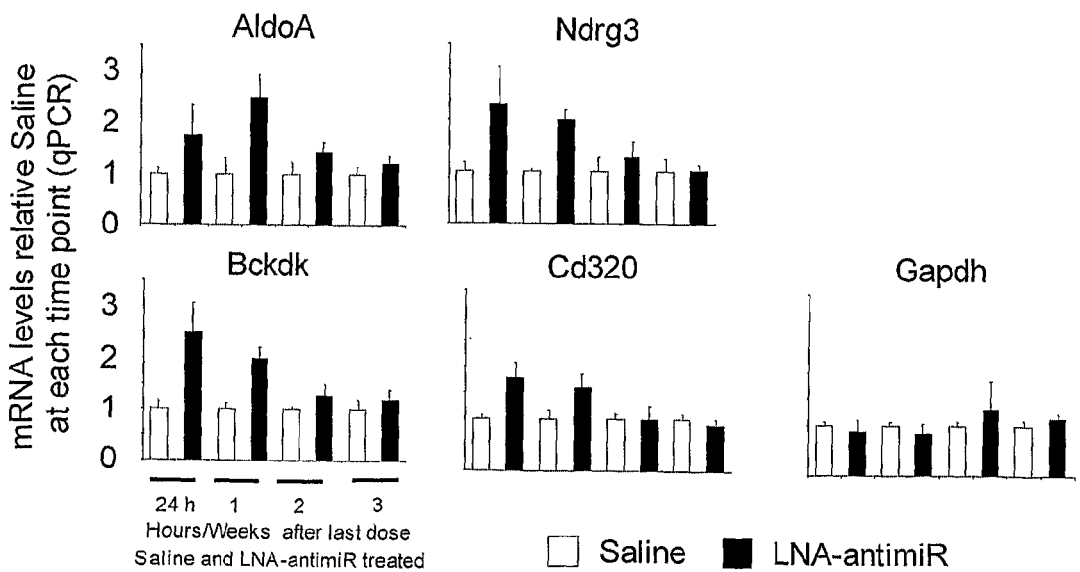
FIG. 10. Transient induction of miR-122a target mRNAs following SPC3372 treatment. NMRI female mice were treated with 25 mg/kg/day SPC3372 along with saline control for three consecutive days and sacrificed 1, 2 or 3 weeks after last dose, respectively. RNA was extracted from livers and mRNA levels of predicted miR-122a target mRNAs, selected by microarray data were investigated by qPCR. Three animals from each group were analysed.

A transient induction followed by a restoration of normal expression levels in analogy with the restoration of normal miR-122a levels was seen (FIG. 10).

mRNA levels are normalized to the individual GAPDH levels and to the mean of the Saline treated group at each individual time point. Included are also the values from the animals sacrificed 24 hours after last dose. Shown is mean and standard deviation, n=3 (24 h n=3)

Example 19

Induction of Vldlr in Liver by SPC3372 Treatment

The same liver RNA samples as in previous example were investigated for Vldlr induction.

Figure 11:
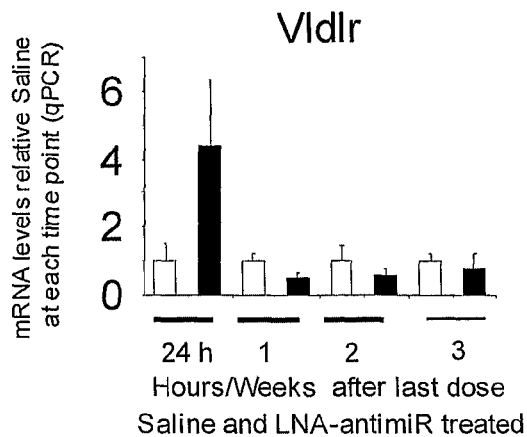
FIG. 11. Induction of Vldlr in liver by SPC3372 treatment. The same liver RNA samples as in previous example (FIG. 10) were investigated for Vldlr induction.

A transient up-regulation was seen after SPC3372 treatment, as with the other predicted miR-122a target mRNAs (FIG. 11)

Example 20

Stability of miR-122a/SPC3372 Duplex in Mouse Plasma

Figure 12:
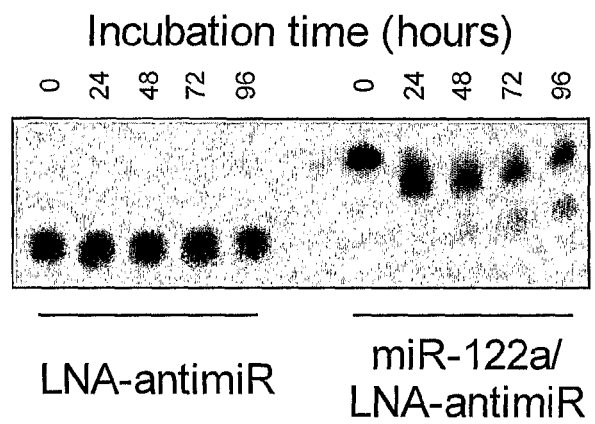
FIG. 12. Stability of miR-122a/SPC3372 duplex in mouse plasma. Stability of SPC3372 and SPC3372/miR-122a duplex were tested in mouse plasma at 37° C. over 96 hours. Shown in FIG. 12 is a SYBR-Gold stained PAGE.

Stability of SPC3372 and SPC3372/miR-122a duplex were tested in mouse plasma at 37° C. over 96 hours. Shown in FIG. 12 is a SYBR-Gold stained PAGE.

SPC3372 was completely stable over 96 hours. The SPC3372/miR-122a duplex was immediately truncated (degradation of the single stranded miR-122a region not covered by SPC3372) but thereafter almost completely stable over 96 hours.

The fact that a preformed SPC3372/miR-122 duplex showed stability in serum over 96 hours together with the high thermal duplex stability of SPC3372 molecule supported our notion that inhibition of miR-122a by SPC3372 was due to stable duplex formation between the two molecules, which has also been reported in cell culture (Naguibneva et al. 2006).

Example 21

Sequestering of Mature miR-122a by SPC3372 Leads to Duplex Formation

Figure 13:
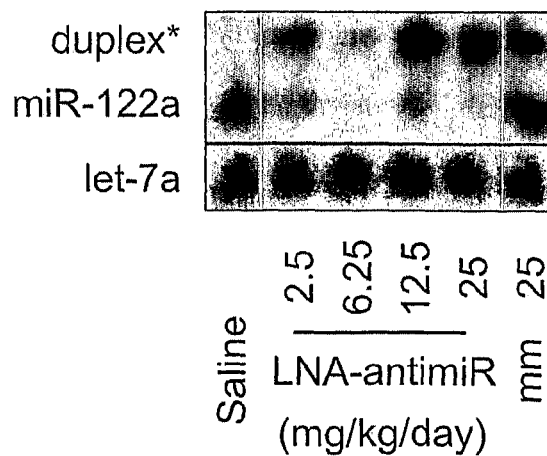
FIG. 13. Sequestering of mature miR-122a by SPC3372 leads to duplex formation. Shown in FIG. 13 is a membrane probed with a miR-122a specific probe (upper panel) and re-probed with a Let-7 specific probe (lower panel). With the miR-122 probe, two bands could be detected, one corresponding to mature miR-122 and one corresponding to a duplex between SPC3372 and miR-122.

The liver RNA was also subjected to microRNA Northern blot. Shown in FIG. 13 is a membrane probed with a miR-122a specific probe (upper panel) and re-probed with a Let-7 specific probe (lower panel). With the miR-122 probe, two bands could be detected, one corresponding to mature miR-122 and one corresponding to a duplex between SPC3372 and miR-122.

To confirm silencing of miR-122, liver RNA samples were subjected to small RNA northern blot analysis, which showed significantly reduced levels of detectable mature miR-122, in accordance with our real-time RT-PCR results. By comparison, the levels of the let-7a control were not altered. Interestingly, we observed dose-dependent accumulation of a shifted miR-122/SPC3372 heteroduplex band, suggesting that SPC3372 does not target miR-122 for degradation, but rather binds to the microRNA, thereby sterically hindering its function.

Northern blot analysis was performed as follows:

Preparation of northern membranes was done as described in Sempere et al. 2002, except for the following changes: Total RNA, 10 μg per lane, in formamide loading buffer (47.5% formamide, 9 mM EDTA, 0.0125% Bromophenol Blue, 0.0125% Xylene Cyanol, 0.0125% SDS) was loaded onto a 15% denaturing Novex TBE-Urea polyacrylamide gel (Invitrogen) without preheating the RNA. The RNA was electrophoretically transferred to a GeneScreen plus Hybridization Transfer Membrane (PerkinElmer) at 200 mA for 35 min. Membranes were probed with 32P-labelled LNA-modified oligonucleotides complimentary to the mature microRNAs*. The LNA oligonucleotides were labelled and hybridized to the membrane as described in (Válóczi et al. 2004) except for the following changes: The prehybridization and hybridization solutions contained 50% formamide, 0.5% SDS, 5×SSC, 5×Denhardt's solution and 20 μg/ml sheared denatured herring sperm DNA. Hybridizations were performed at 45° C. The blots were visualized by scanning in a Storm 860 scanner. The signal of the background membrane was subtracted from the radioactive signals originating from the miRNA bands. The values of the miR-122 signals were corrected for loading differences based on the let-7a signal. To determine the size of the radioactive signals the Decade Marker System (Ambion) was used according to the suppliers' recommendations.

Figure 14:
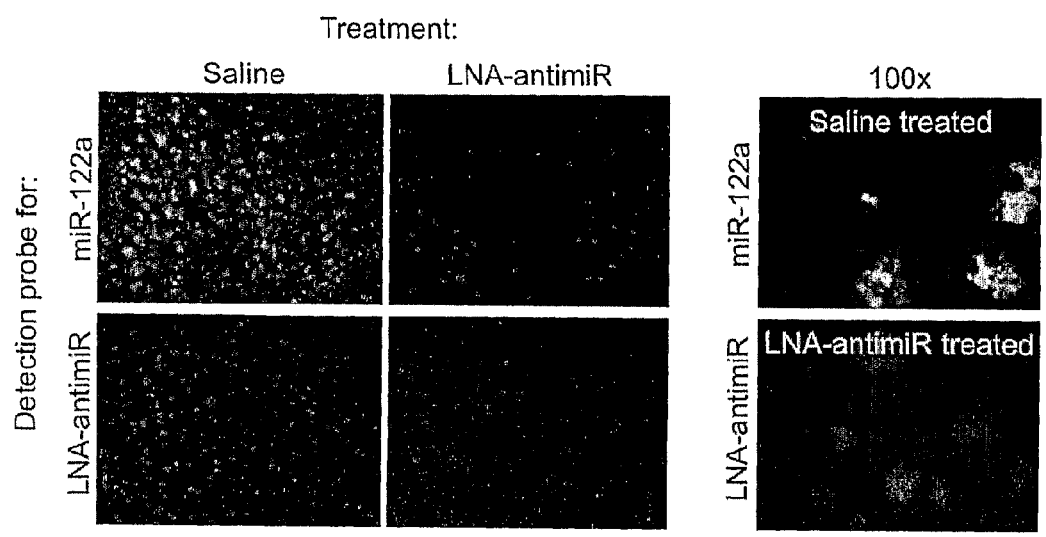
FIG. 14. miR-122a sequestering by SPC3372 along with SPC3372 distribution assessed by in situ hybridization of liver sections. Liver cryo-sections from treated animals were FIG. 15. Liver gene expression in miR-122 LNA-antimiR treated mice. Saline and LNA-antimiR treated mice were compared by genome-wide expression profiling using Affymetrix Mouse Genome 430 2.0 arrays. (a,1) Shown is number of probes displaying differentially expression in liver samples of LNA-antimiR-122 treated and saline treated mice 24 hours post treatment. (b,2) The occurrence of miR-122 seed sequence in differentially expressed genes. The plot shows the percentage of transcripts with at least one miR-122 seed recognition sequence in their 3' UTR. Random: Random sequences were generated and searched for miR-122 seed recognition sequences. Temporal liver gene expression profiles in LNA-antimiR treated mice. Mice were treated with 25 mg/kg/day LNA-antimiR or saline for three consecutive days and sacrificed 1, 2 or 3 weeks after last dose. Included are also the values from the animals sacrificed 24 hours after last dose. (c,3) RNA samples from different time points were also subjected to expression profiling. Hierarchical cluster analysis of expression profiles of genes identified as differentially expressed between LNA-antimiR and saline treated mice 24 hours, one week or three weeks post treatment. (d,4) Expression profiles of genes identified as differentially expressed between LNA-antimiR and saline treated mice 24 hours post treatment were followed over time. The expression ratios of up- and downregulated genes in LNA-antimiR treated mice approach 1 over the time-course, indicating a reversible effect of the LNA-antimiR treatment.

Example 22 miR-122a Sequestering by SPC3372 Along with SPC3372 Distribution Assessed by In Situ Hybridization of Liver Sections Liver cryo-sections from treated animals were subjected to in situ hybridizations for detection and localization of miR-122 and SPC3372 (FIG. 14). A probe complementary to miR-122 could detect miR-122a. A second probe was complementary to SPC3372. Shown in FIG. 14 is an overlay, in green is distribution and apparent amounts of miR-122a and SPC3372 and blue is DAPI nuclear stain, at 10× magnification. 100× magnifications reveal the intracellular distribution of miR-122a and SPC3372 inside the mouse liver cells.

The liver sections from saline control animals showed a strong miR-122 staining pattern over the entire liver section, whereas the sections from SPC3372 treated mice showed a significantly reduced patchy staining pattern. In contrast, SPC3372 molecule was readily detected in SPC3372 treated liver, but not in the untreated saline control liver. Higher magnification localized miR-122a to the cytoplasm in the hepatocytes, where the miR-122 in situ pattern was clearly compartmentalized, while SPC3372 molecule was evenly distributed in the entire cytoplasm.

Example 23

Micro Array Analysis

Figure 15:
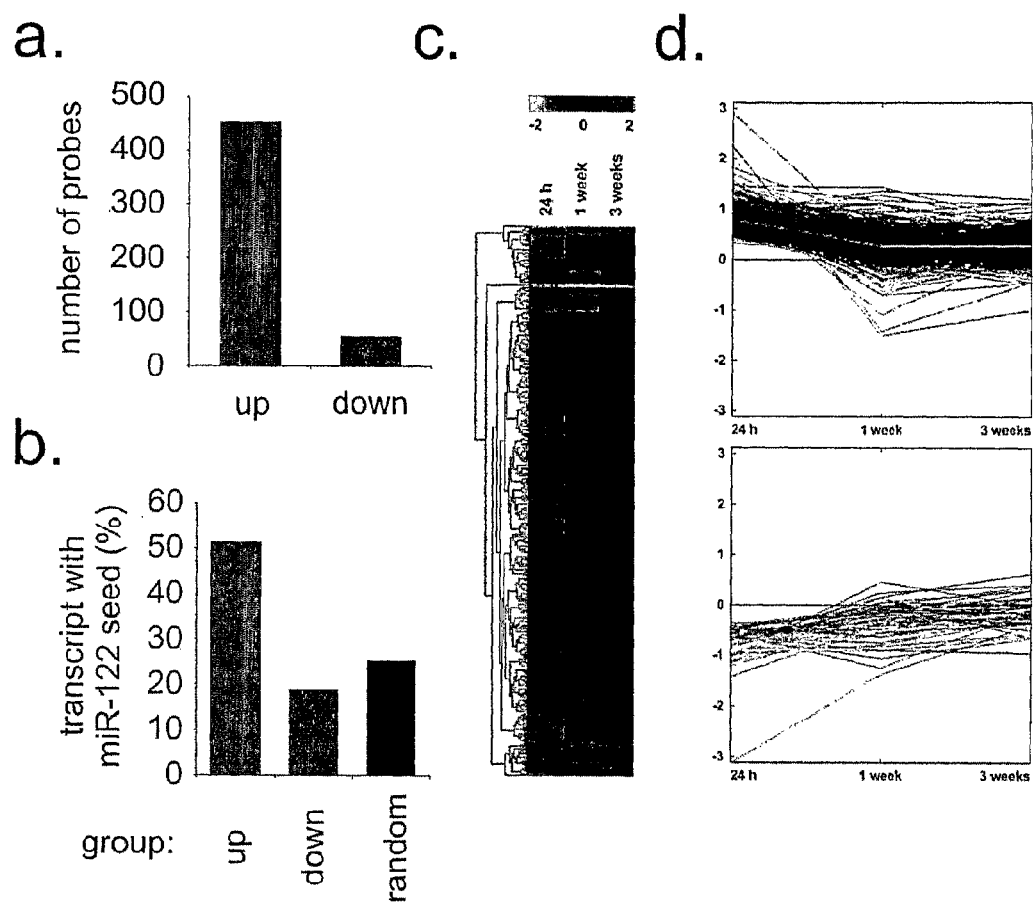

We carried out genome-wide expression profiling of total RNA samples from saline LNA-antimiR-122 treated and LNA mismatch control treated mice livers 24 hours after the last dose using Affymetrix Mouse Genome 430 2.0 arrays. Analysis of the array data revealed 455 transcripts that were upregulated in the LNA-antimiR treated mice livers compared to saline and LNA mismatch controls, while 54 transcripts were downregulated (FIG. 15a). A total of 415 of the upregulated and 53 downregulated transcripts could be identified in the Ensembl database. We subsequently examined the 3' untranslated regions (UTRs) of the differentially expressed mRNAs for the presence of the 6 nt sequence CACTCC, corresponding to the reverse complement of the nucleotide 2-7 seed region in mature miR-122. The number of transcripts having at least one miR-122 recognition sequence was 213 (51%) among the upregulated transcripts, and 10 (19%) within the downregulated transcripts, while the frequency in a random sequence population was 25%, implying that a significant pool of the upregulated mRNAs represent direct miR-122 targets in the liver (FIG. 15b).

The LNA-antimiR treatment showed maximal reduction of miR-122 levels at 24 hours, 50% reduction at one week and matched saline controls at three weeks after last LNA dose (Example 12 "old design"). This coincided with a markedly reduced number of differentially expressed genes between the two mice groups at the later time points. Compared to the 509 mRNAs 24 hours after the last LNA dose we identified 251 differentially expressed genes after one week, but only 18 genes after three weeks post treatment (FIGS. 15c and 15d). In general genes upregulated 24 hours after LNA-antimiR treatment then reverted towards control levels over the next two weeks (FIG. 15d).

In conclusion, a large portion of up-regulated/de-repressed genes after LNA-antimiR treatment are miR-122 targets, indicating a very specific effect for blocking miR-122. Also genes up-regulated/de-repressed approach normal levels 3 weeks after end of treatment, suggest a relative long therapeutic effect, but however not cause a permanent alteration, ie the effect is reversible.

Methods:

Gene Expression Profiling of LNA-antimiR Treated Mice.

Expression profiles of livers of saline and LNA-antimiR treated mice were compared. NMRI female mice were treated with 25 mg/kg/day of LNA-antimiR along with saline control for three consecutive days and sacrificed 24 h, 1, 2 or 3 weeks after last dose. Additionally, expression profiles of livers of mice treated with the mismatch LNA control oligonucleotide 24 h after last dose were obtained. Three mice from each group were analyzed, yielding a total of 21 expression profiles. RNA quality and concentration was measured using an Agilent 2100 Bioanalyzer and Nanodrop ND-1000, respectively. Total RNA was processed following the GeneChip Expression 3'-Amplification Reagents One-cycle cDNA synthesis kit instructions (Affymetrix Inc, Santa Clara, Calif., USA) to produce double-stranded cDNA. This was used as a template to generate biotin-labeled cRNA following manufacturer's specifications. Fifteen micrograms of biotin-labeled cRNA was fragmented to strands between 35 and 200 bases in length, of which 10 micrograms were hybridised onto Affymetrix Mouse Genome 430 2.0 arrays overnight in the GeneChip Hybridisation oven 6400 using standard procedures. The arrays were washed and stained in a GeneChip Fluidics Station 450. Scanning was carried out using the GeneChip Scanner 3000 and image analysis was performed using GeneChip Operating Software. Normalization and statistical analysis were done using the LIMMA software package for the R programming environment 27. Probes reported as absent by GCOS software in all hybridizations were removed from the dataset. Additionally, an intensity filter was applied to the dataset to remove probes displaying background-corrected intensities below 16. Data were normalized using quantile normalization 28. Differential expression was assessed using a linear model method. P values were adjusted for multiple testing using the Benjamini and Hochberg. Tests were considered to be significant if the adjusted p values were p<0.05. Clustering and visualization of Affymetrix array data were done using the MultiExperiment Viewer software 29.

Target Site Prediction

Transcripts with annotated 3' UTRs were extracted from the Ensembl database (Release 41) using the EnsMart data mining tool 30 and searched for the presence of the CACTCC sequence which is the reverse complement of the nucleotide 2-7 seed in the mature miR-122 sequence. As a background control, a set of 1000 sequences with a length of 1200 nt, corresponding to the mean 3' UTR length of the up- and downregulated transcripts at 24 h after last LNA-antimiR dose, were searched for the 6 nucleotide miR-122 seed matches. This was carried out 500 times and the mean count was used for comparison Example 24

Dose-Dependent Inhibition of miR-122 in Mouse Liver by LNA-antimiR is Enhanced as Compared to Antagomir Inhibition of miR-122

NMRI female mice were treated with indicated doses of LNA-antimiR (SPC3372) along with a mismatch control (mm, SPC3373), saline and antagomir (SPC3595) for three consecutive days and sacrificed 24 hours after last dose (as in example 11 "old design", n=5). miR-122 levels were analyzed by qPCR and normalized to the saline treated group. Genes with predicted miR-122 target site and up regulated in the expression profiling (AldoA, Nrdg3, Bckdk and CD320) showed dose-dependent de-repression by increasing LNA-antimiR doses measured by qPCR.

Figure 16:
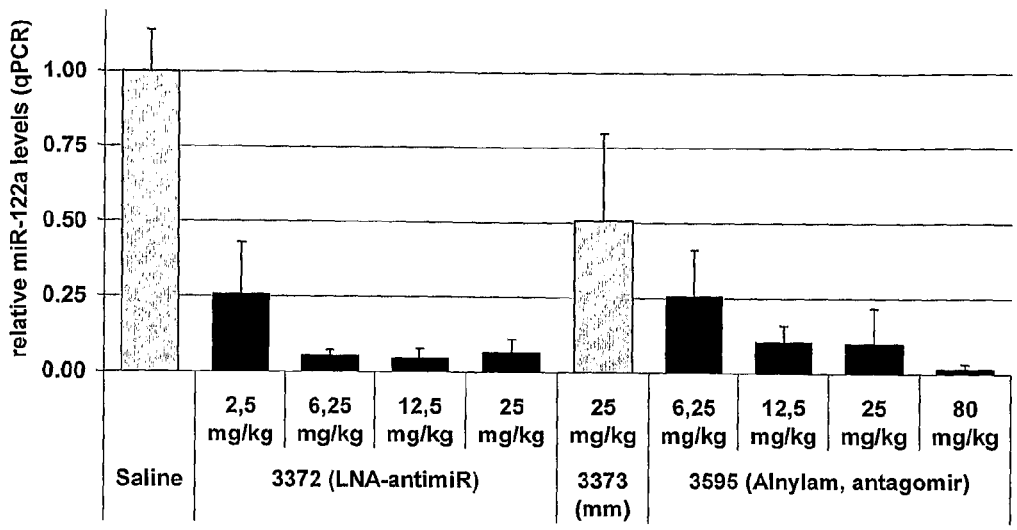
FIG. 16. The effect of treatment with SPC3372 and 3595 on miR-122 levels in mice livers.
Figure 17:
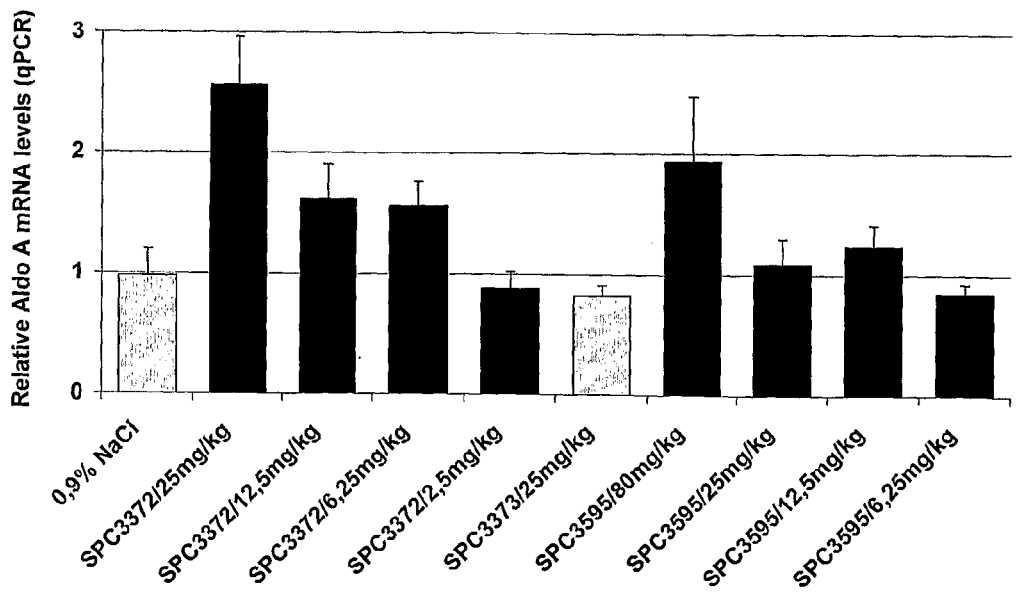
FIG. 17. The effect of treatment with SPC3372 and 3595 on Aldolase A levels in mice livers.
Figure 18:
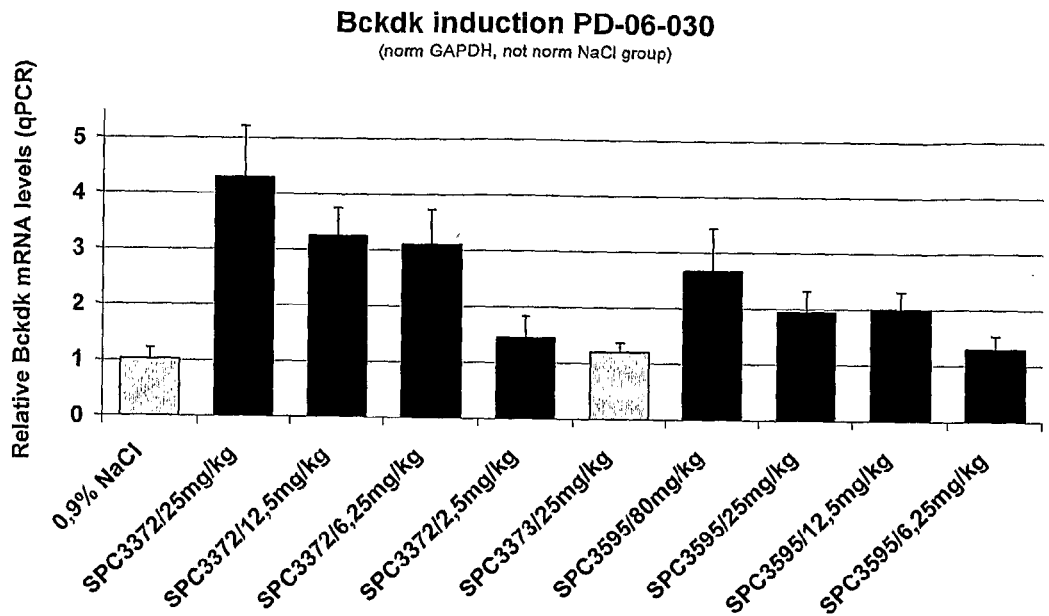
FIG. 18. The effect of treatment with SPC3372 and 3595 on Bckdk levels in mice livers.
Figure 19:
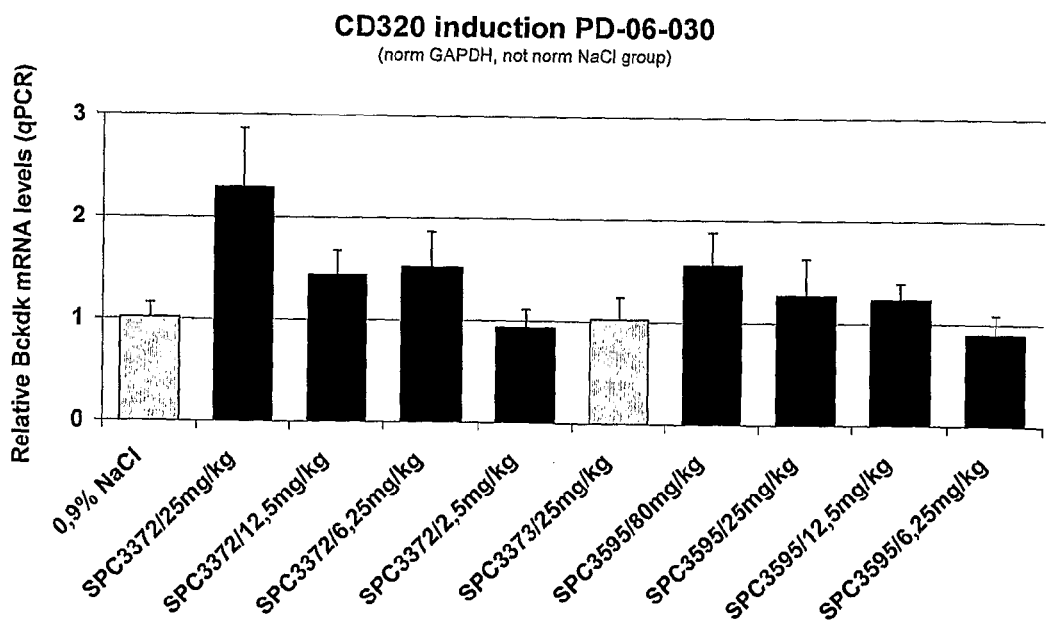
FIG. 19. The effect of treatment with SPC3372 and 3595 on CD320 levels in mice livers.
Figure 20:
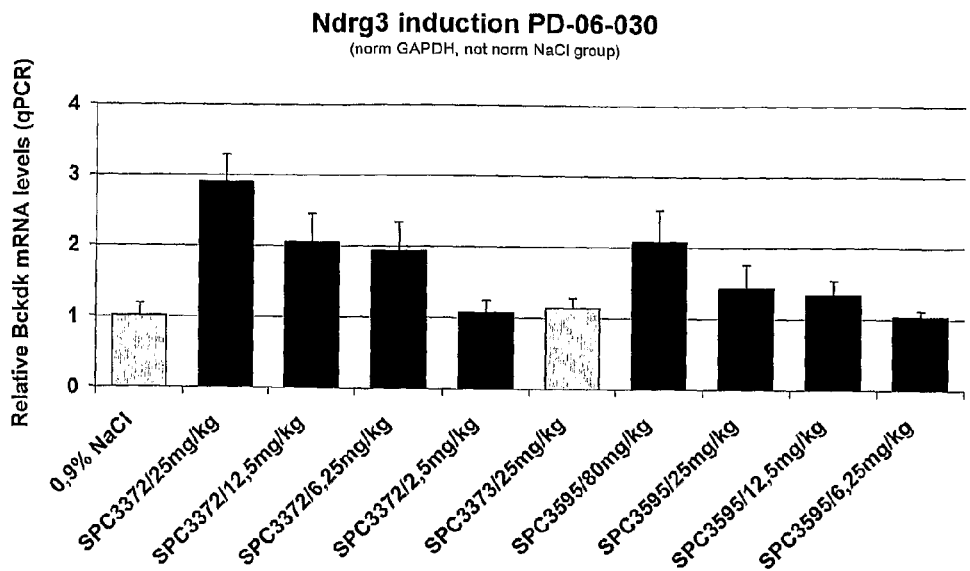
FIG. 20. The effect of treatment with SPC3372 and 3595 on Ndrg3 levels in mice livers.

The de-repression was consistently higher on all tested miR-122 target mRNAs (AldoA, Bckdk, CD320 and Nrdg3 FIG. 17, 18, 19, 20) in LNA-antimiR treated mice compared to antagomir treated mice. This was also indicated when analysing the inhibition of miR-122 by miR-122 specific qPCR (FIG. 16). Hence LNA-antimiRs give a more potent functional inhibition of miR-122 than corresponding dose antagomir.

Example 25

Inhibition of miR-122 by LNA-antimiR in Hypercholesterolemic Mice Along with Cholesterol Reduction and miR-122 Target mRNA De-Repression C57BL/6J female mice were fed on high fat diet for 13 weeks before the initiation of the SPC3649 treatment. This resulted in increased weight to 30-35 g compared to the weight of normal mice, which was just under 20 g, as weighed at the start of the LNA-antimiR treatment. The high fat diet mice lead to significantly increased total plasma cholesterol level of about 130 mg/dl, thus rendering the mice hypercholesterolemic compared to the normal level of about 70 mg/dl. Both hypercholesterolemic and normal mice were treated i.p. twice weekly with 5 mg/kg SPC3649 and the corresponding mismatch control SPC3744 for a study period of 5½ weeks. Blood samples were collected weekly and total plasma cholesterol was measured during the entire course of the study. Upon sacrificing the mice, liver and blood samples were prepared for total RNA extraction, miRNA and mRNA quantification, assessment of the serum transaminase levels, and liver histology.

Figure 21:
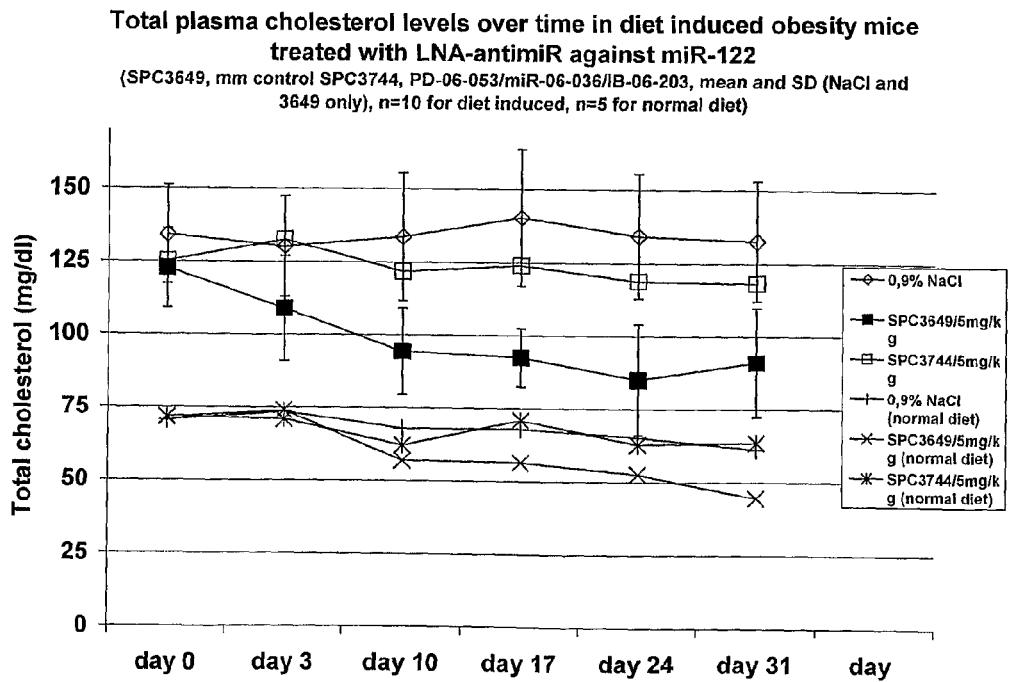
FIG. 21. The effect of long-term treatment with SPC3649 on total plasma cholesterol in hypercholesterolemic and normal mice. Weekly samples of blood plasma were obtained from the SPC3649 treated and saline control mice once weekly followed by assessment of total plasma cholesterol. The mice were treated with 5 mg/kg SPC3649, SPC3744 or saline twice weekly. Normal mice given were treated in parallel.

Treatment of hypercholesterolemic mice with SPC3649 resulted in reduction of total plasma cholesterol of about 30% compared to saline control mice already after 10 days and sustained at this level during the entire study (FIG. 21). The effect was not as pronounced in the normal diet mice. By contrast, the mismatch control SPC3744 did not affect the plasma cholesterol levels in neither hypercholesterolemic nor normal mice.

Figure 22:
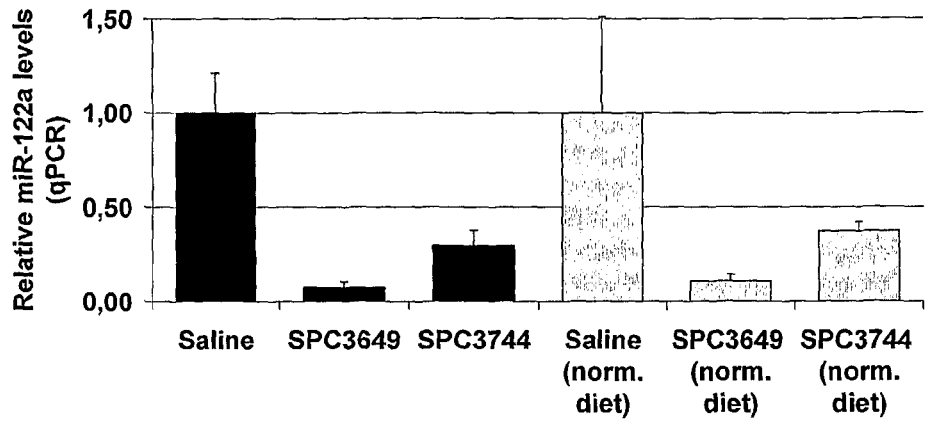
FIG. 22. The effect of long-term treatment with SPC3649 on miR-122 levels in hypercholesterolemic and normal mice.
Figure 23:
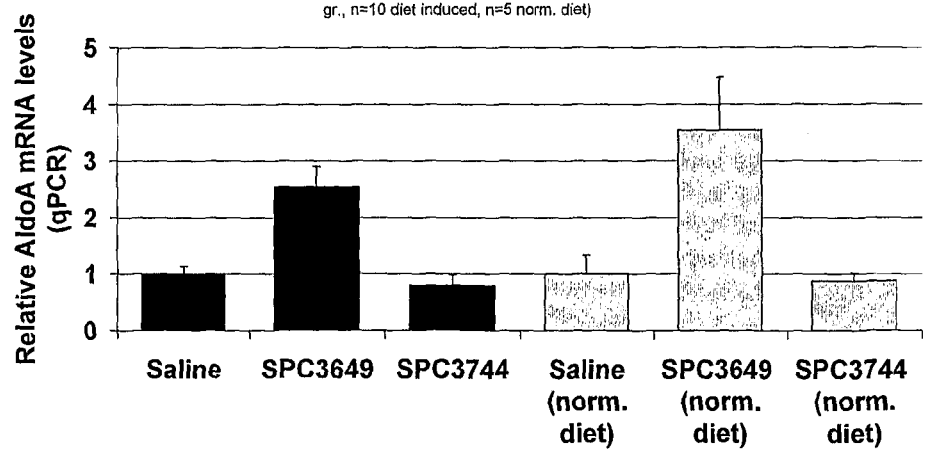
FIG. 23. The effect of long-term treatment with SPC3649 on Aldolase A levels in hypercholesterolemic and normal mice.
Figure 24:
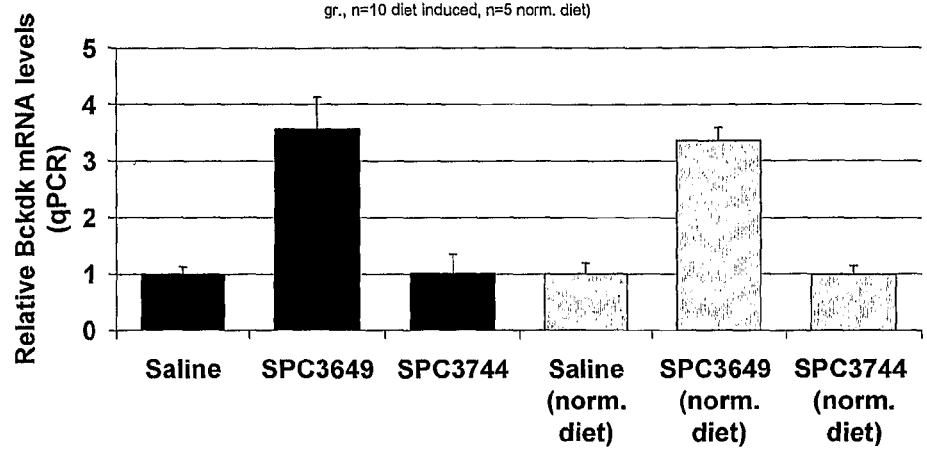
FIG. 24. The effect of long-term treatment with SPC3649 on Bckdk levels in hypercholesterolemic and normal mice.

Quantification of miR-122 inhibition and miR-122 target gene mRNA de-repression (AldoA and Bckdk) after the long-term treatment with SPC3649 revealed a comparable profile in both hypercholesterolemic and normal mice (FIG. 22, 23, 24), thereby demonstrating the potency of SPC3649 in miR-122 antagonism in both animal groups. The miR-122 qPCR assay indicated that also the mismatch control SPC3744 had an effect on miR-122 levels in the treated mice livers, albeit to a lesser extent compared to SPC3649. This might be a reduction associated with the stem-loop qPCR. Consistent with this notion, treatment of mice with the mismatch control SPC3744 did not result in any functional de-repression of the direct miR-122 target genes (FIGS. 23 and 24) nor reduction of plasma cholesterol (FIG. 21), implying that SPC3649-mediated antagonism of miR-122 is highly specific in vivo.

Figure 25:
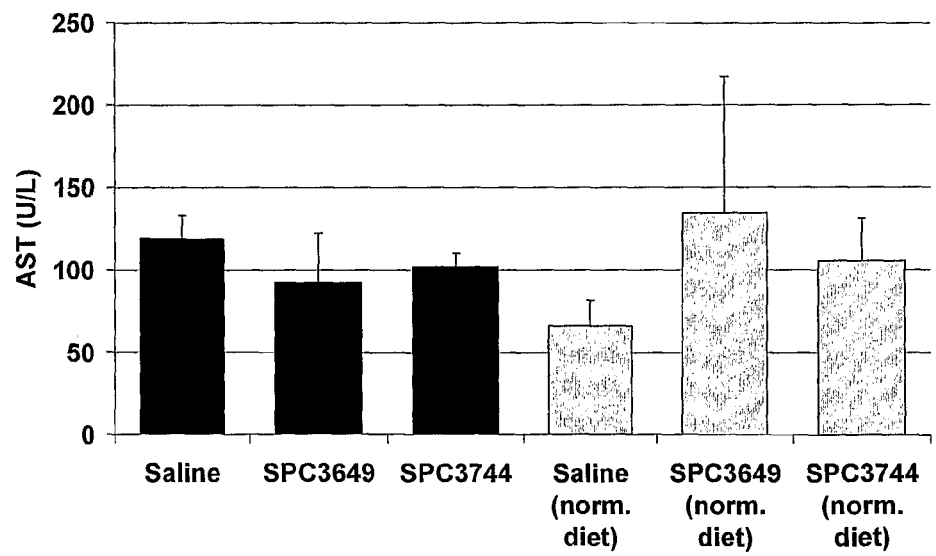
FIG. 25. The effect of long-term treatment with SPC3649 on AST levels in hypercholesterolemic and normal mice.
Figure 26:
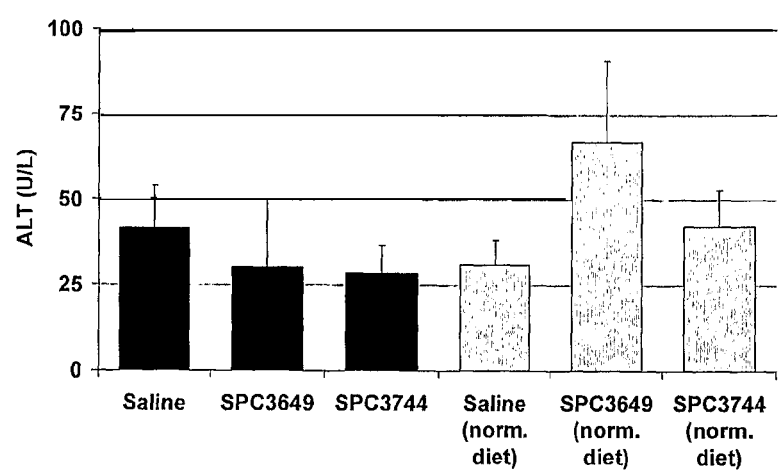
FIG. 26. The effect of long-term treatment with SPC3649 on ALT levels in hypercholesterolemic and normal mice.

Liver enzymes in hypercholesterolemic and normal mice livers were assessed after long term SPC3649 treatment. No changes in the alanine and aspartate aminotransferase (ALT and AST) levels were detected in the SPC3649 treated hypercholesterolemic mice compared to saline control mice (FIGS. 25 and 26). A possibly elevated ALT level was observed in the normal mice after long-term treatment with SPC3649 (FIG. 26).

Example 26

Methods for Performing the LNA-antimiR/Hypercholesterolemic Experiment and Analysis Mice and Dosing.

C57BL/63 female mice (Taconic M&B Laboratory Animals, Ejby, Denmark) were used. All substances were formulated in physiological saline (0.9% NaCl) to final concentration allowing the mice to receive an intraperitoneal injection volume of 10 ml/kg.

In the diet induced obesity study, the mice received a high fat (60EN %) diet (D12492, Research Diets) for 13 weeks to increase their blood cholesterol level before the dosing started. The dose regimen was stretched out to 5½ weeks of 5 mg/kg LNA-antimiR™ twice weekly. Blood plasma was collected once a week during the entire dosing period. After completion of the experiment the mice were sacrificed and RNA extracted from the livers for further analysis. Serum was also collected for analysis of liver enzymes.

Total RNA Extraction.

The dissected livers from sacrificed mice were immediately stored in RNA later (Ambion). Total RNA was extracted with Trizol reagent according to the manufacturer's instructions (Invitrogen), except that the precipitated RNA pellet was washed in 80% ethanol and not vortexed.

MicroRNA-Specific Quantitative RT-PCR.

The miR-122 and let-7a microRNA levels were quantified with TaqMan microRNA Assay (Applied Biosystems) following the manufacturer's instructions. The RT reaction was diluted ten times in water and subsequently used for real time PCR amplification according to the manufacturer's instructions. A two-fold cDNA dilution series from liver total RNA of a saline-treated animal or mock transfected cells cDNA reaction (using 2.5 times more total RNA than in samples) served as standard to ensure a linear range (Ct versus relative copy number) of the amplification. Applied Biosystems 7500 or 7900 real-time PCR instrument was used for amplification.

Quantitative RT-PCR mRNA quantification of selected genes was done using standard TaqMan assays (Applied Biosystems). The reverse transcription reaction was carried out with random decamers, 0.5 µg total RNA, and the M-MLV RT enzyme from Ambion according to a standard protocol. First strand cDNA was subsequently diluted 10 times in nuclease-free water before addition to the RT-PCR reaction mixture. A two-fold cDNA dilution series from liver total RNA of a saline-treated animal or mock transfected cells cDNA reaction (using 2.5 times more total RNA than in samples) served as standard to ensure a linear range (Ct versus relative copy number) of the amplification. Applied Biosystems 7500 or 7900 real-time PCR instrument was used for amplification.

Metabolic Measurements.

Immediately before sacrifice retro-orbital sinus blood was collected in EDTA-coated tubes followed by isolation of the plasma fraction. Total plasma cholesterol was analysed using ABX Pentra Cholesterol CP (Horiba Group, Horiba ABX Diagnostics) according to the manufacturer's instructions.

Liver Enzymes (ALT and AST) Measurement

Serum from each individual mouse was prepared as follows: Blood samples were stored at room temperature for 2 h before centrifugation (10 min, 3000 rpm at room temperature). After centrifugation, serum was harvested and frozen at −20° C.

ALT and AST measurement was performed in 96-well plates using ALT and AST reagents from ABX Pentra according to the manufacturer's instructions. In short, serum samples were diluted 2.5 fold with $H_2O$ and each sample was assayed in duplicate. After addition of 50 µl diluted sample or standard (multical from ABX Pentra) to each well, 200 µl of 37° C. AST or ALT reagent mix was added to each well. Kinetic measurements were performed for 5 min with an interval of 30s at 340 nm and 37° C. using a spectrophotometer.

Example 27

Modulation of Hepatitis C Replication by LNA-antimiR (SPC3649)

Oligos used in this example (uppercase: LNA, lowercase DNA, LNA Cs are methyl, and LNAs are preferably B-D-oxy (o subscript after LNA residue):

SPC3649 (LNA-antimiR targeting miR-122,
was in the initial small scale synthesis designated SPC3549)
5'-$^mC_s{}^oc_sA_s{}^ot_st_sG_s{}^oT_s{}^oc_sa_s{}^mC_s{}^oa_s{}^mC_s{}^ot_s{}^mC_s{}^{om}C^o$-3'
SPC3648 (LNA-antimiR targeting miR-122,
was in the initial small scale synthesis designated SPC3548)
5'-$A_s{}^ot_st_sG_s{}^oT_s{}^oc_sa_s{}^mC_s{}^oa_s{}^mC_s{}^ot_s{}^mC_s{}^{om}C^o$-3'
SPC3550 (4 nt mismatch control to SPC3649) SEQ ID 63
5'-$^mC_s{}^oc_sA_s{}^ot_st_s{}^mC_s{}^oT_s{}^og_sa_s{}^mC_s{}^oc_s{}^mC_s{}^ot_sA_s{}^{om}C^o$-3'
2'OMe anti-122: full length (23 nt) 2'OMe modified oligo complementary to miR-122
2'OMe Ctrl: scrambled 2'OMe modified control Hepatitis C (HCV) replication has been shown to be facilitated by miR-122 and consequently, antagonizing miR-122 has been demonstrated to affect HCV replication in a hepatoma cell model in vitro. We assess the efficacy of SPC3649 reducing HCV replication in the Huh-7 based cell model. The different LNA-antimiR molecules along with a 2' OMe antisense and scramble oligonucleotide are transfected into Huh-7 cells, HCV is allowed to replicate for 48 hours.

Total RNA samples extracted from the Huh-7 cells are subjected to Northern blot analysis.

Example 28

Enhanced LNA-antimiR™ Antisense Oligonucleotide Targeting miR-21 Mature miR-21 Sequence from Sanger Institute miRBase

```
>hsa-miR-21 MIMAT0000076
                                    (SEQ ID NO 4)
UAGCUUAUCAGACUGAUGUUGA >mmu-miR-21 MIMAT0000530
                                    (SEQ ID NO 64)
UAGCUUAUCAGACUGAUGUUGA
```

Sequence of Compounds:

```
SPC3521 miR-21
                                    (SEQ ID NO 65)
5'-FAM TCAgtctgataaGCTa-3'  (gap-mer design)

SPC3870 miR-21(mm)
                                    (SEQ ID NO 66)
5'-FAM TCCgtcttagaaGATa-3'

SPC3825 miR-21
                                    (SEQ ID NO 67)
5'-FAM TcTgtCAgaTaCgAT-3'  (new design)

SPC3826 miR-21(mm)
                                    (SEQ ID NO 68)
5'-FAM TcAgtCTgaTaAgCT-3'

SPC3827 miR-21
                                    (SEQ ID NO 69)
5'-FAM TcAGtCTGaTaAgCT-3'  (new, enhanced design)
```

All compounds have a fully or almost fully thiolated backbone and have here also a FAM label in the 5' end.

miR-21 has been show to be up-regulated in both glioblastoma (Chan et al. Cancer Research 2005, 65 (14), p 6029) and breast cancer (Iorio et al. Cancer Research 2005, 65 (16), p 7065) and hence has been considered a potential 'oncogenic' microRNA. Chan et al, also show induction of apoptosis in glioblastoma cells by antagonising miR-21 with 2'OMe or LNA modified antisense oligonucleotides. Hence, agents antagonising miR-21 have the potential to become therapeutics for treatment of glioblastoma and other solid tumours, such as breast cancer. We present an enhanced LNA modified oligonucleotide targeting miR-21, an LNA-antimiR™, with surprisingly good properties to inhibit miR-21 suited for the abovementioned therapeutic purposes.

Suitable therapeutic administration routes are, for example, intracranial injections in glioblastomas, intratumoral injections in glioblastoma and breast cancer, as well as systemic delivery in breast cancer Inhibition of miR-21 in U373 Glioblastoma Cell Line and MCF-7 Breast Cancer Cell Line.

Efficacy of current LNA-anitmiR™ is assessed by transfection at different concentrations, along with control oligonucleotides, into U373 and MCF-7 cell lines known to express miR-21 (or others miR-21 expressing cell lines as well). Transfection is performed using standard Lipofectamine2000 protocol (Invitrogen). 24 hours post transfection, the cells are harvested and total RNA extracted using the Trizol protocol (Invitrogen). Assessment of miR-21 levels, depending on treatment and concentration used is done by miR-21 specific, stem-loop real-time RT-PCR (Applied Biosystems), or alternatively by miR-21 specific non-radioactive northern blot analyses. The detected miR-21 levels compared to vehicle control reflects the inhibitory potential of the LNA-antimiR™.

Functional Inhibition of miR-21 by Assessment of miR-21 Target Gene Up-Regulation.

The effect of miR-21 antagonism is investigated through cloning of the perfect match miR-21 target sequence behind a standard Renilla luciferase reporter system (between coding sequence and 3' UTR, psiCHECK-2, Promega)—see Example 29. The reporter construct and LNA-antimiR™ will be co-transfected into miR-21 expressing cell lines (f. ex. U373, MCF-7). The cells are harvested 24 hours post transfection in passive lysis buffer and the luciferase activity is measured according to a standard protocol (Promega, Dual Luciferase Reporter Assay System). The induction of luciferase activity is used to demonstrate the functional effect of LNA-antimiR™ antagonising miR-21.

Example 29

Luciferase Reporter Assay for Assessing Functional Inhibition of microRNA by LNA-antimiRs and Other microRNA Targeting Oligos: Generalisation of New and Enhanced New Design as Preferred Design for Blocking microRNA Function Oligos used in this example (uppercase: LNA, lowercase: DNA) to assess LNA-antimiR de-repressing effect on luciferase reporter with microRNA target sequence cloned by blocking respective microRNA:

```
target: hsa-miR-122a MIMAT0000421
uggagugugacaaugguguuugu
screened in HUH-7 cell line expressing miR-122
```

| Oligo #, target microRNA, oligo sequence | Design |
| --- | --- |
| 3962:miR-122 5'-ACAAacaccattgtcacacTCCA-3' | Full complement, gap |
| 3965:miR-122 5'-acaaacACCATTGTcacactcca-3' | Full complement, block |
| 3972:miR-122 5'-acAaaCacCatTgtCacActCca-3' | Full complement, LNA_3 |
| 3549 (3649):miR-122 5'-CcAttGTcaCaCtCC-3' | New design |
| 3975:miR-122 5'-CcAtTGTcaCACtCC-3' | Enhanced new design |

```
target: hsa-miR-19b MIMAT0000074
ugugcaaauccaugcaaaacuga
screened HeLa cell line expressing miR-19b
```

| Oligo #, target microRNA, oligo sequence | Design |
| --- | --- |
| 3963:miR-19b 5'-TCAGttttgcatggatttgCACA-3' | Full complement, gap |
| 3967:miR-19b 5'-tcagttTTGCATGGatttgcaca-3' | Full complement, block |
| 3973:miR-19b 5'-tcAgtTttGcaTggAttTgcAca-3' | Full complement, LNA_3 |
| 3560:miR-19b 5'-TgCatGGatTtGcAC-3' | New design |
| 3976:miR-19b 5'-TgCaTGGatTTGcAC-3' | Enhanced new design |

```
target: hsa-miR-155 MIMAT0000646
uuaaugcuaaucgugauagggg
screen in 518A2 cell line expressing miR-155
```

| Oligo #, target microRNA, oligo sequence | Design |
| --- | --- |
| 3964:miR-155 5'-CCCCtatcacgattagcaTTAA-3' | Full complement, gap |
| 3968:miR-155 5'-cccctaTCACGATTagcattaa-3' | Full complement, block |
| 3974:miR-155 5'-cCccTatCacGatTagCatTaa-3' | Full complement, LNA_3 |
| 3758:miR-155 5'-TcAcgATtaGcAtTA-3' | New design |
| 3818:miR-155 5'-TcAcGATtaGCAtTA-3' | Enhanced new design |

SEQ ID NOs as before.

A reporter plasmid (psiCheck-2 Promega) encoding both the Renilla and the Firefly variants of luciferase was engineered so that the 3'UTR of the Renilla luciferase includes a single copy of a sequence fully complementary to the miRNA under investigation.

Cells endogenously expressing the investigated miRNAs (HuH-7 for miR-122a, HeLa for miR-19b, 518A2 for miR-155) were co-transfected with LNA-antimiRs or other miR binding oligonucleotides (the full complementary ie full length) and the corresponding microRNA target reporter plasmid using Lipofectamine 2000 (Invitrogen). The transfection and measurement of luciferase activity were carried out according to the manufacturer's instructions (Invitorgen Lipofectamine 2000/Promega Dual-luciferase kit) using 150 000 to 300 000 cells per well in 6-well plates. To compensate for varying cell densities and transfection efficiencies the Renilla luciferase signal was normalized with the Firefly luciferase signal. All experiments were done in triplicate.

Figure 27:
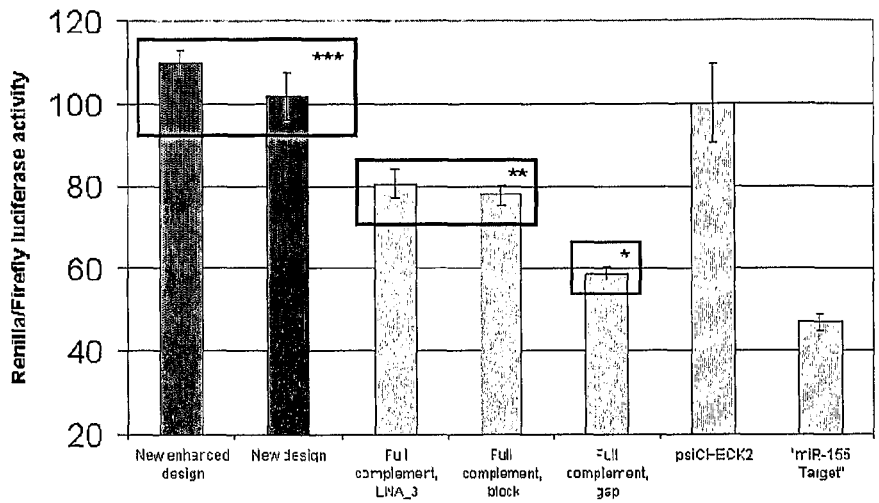
FIG. 27. Modulation of HCV replication by SPC3649 in a Huh-7 cell model. Northern blot analysis of HCV RNA in Huh-7 cells after transfection with different LNA-antimiR (SPC3648, SPC3649 and SPC3550) and 2' OMe antago-mir-122 molecules (upper panel). The hybridisation signal intensities were quantified and normalized to spectrin mRNA signals in each lane (lower panel).
Figure 28:
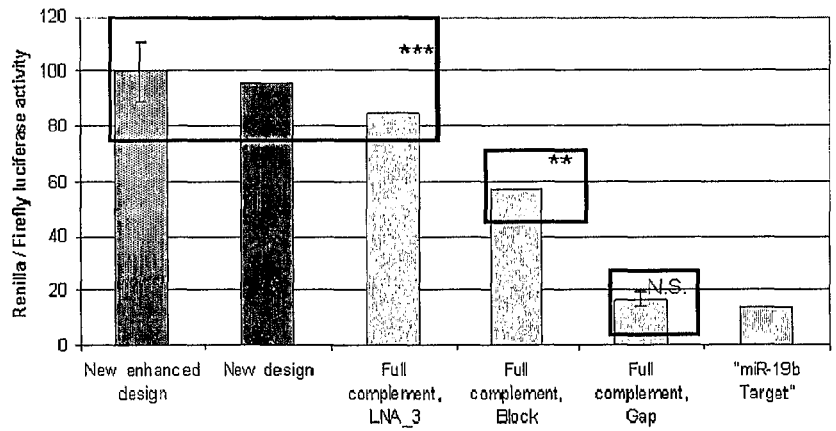
FIG. 28. Functional de-repression of renilla luciferase with miR-19b target by miR-19b blocking oligonucleotides in an endogenously miR-19b expressing cell line, HeLa. "miR-19b target" is the plasmid with miR-19b target but not co-transfected with oligo blocking miR-19b and hence represent fully miR-19b repressed renilla luciferase expression.
Figure 29:
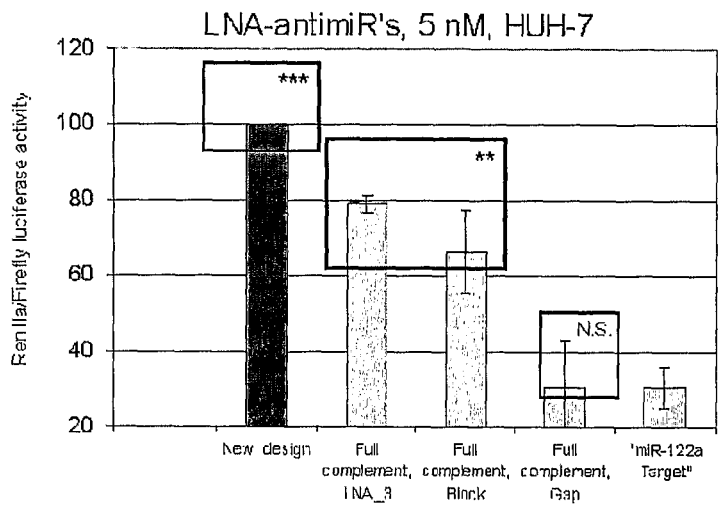
FIG. 29. Functional de-repression of renilla luciferase with miR-122 target by miR-122 blocking oligonucleotides in an endogenously miR-122 expressing cell line, Huh-7. "miR-122 target" is the corresponding plasmid with miR-122 target but not co-transfected with oligo blocking miR-122 and hence represent fully miR-122 repressed renilla luciferase expression.
Figure 30:
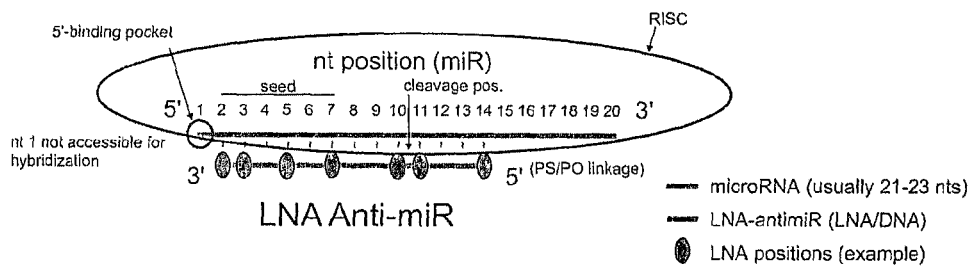
FIG. 30. Diagram illustrating the alignment of an oligonucleotide according to the invention and a microRNA target.

Surprisingly, new design and new enhanced design were the best functional inhibitors for all three microRNA targets, miR-155, miR-19b and miR-122 (FIG. 27, 28, 29). The results are summarized in following table 3.

Result summary:

TABLE 3

Degree of de-repression of endogenous miR-155, miR-19b and miR-122a function by various designs of LNA-antimiR's.

| Design | miR-155 | miR-19b | miR-122a |
|---|---|---|---|
| New enhanced design | *** | *** | no data |
| New design | *** | *** | *** |
| Full complement, LNA_3 | ** | *** | ** |
| Full complement, block | ** | ** | ** |
| Full complement, gap | * | not signif. | not signif. |

REFERENCES

Abelson, J. F. et al. 2005. Science 310: 317-20.
Bartel, D. P. 2004. Cell 116: 281-297.
Boehm, M., Slack, F. 2005. Science. 310:1954-7.
Brennecke, J. et al. 2003 Cell 113: 25-36.
Calin, G. A. et al. 2002. Proc. Natl. Acad. Sci. USA 99: 15524-15529.
Calin, G. A. et al. 2004. Proc. Natl. Acad. Sci. U.S.A. 101: 2999-3004.
Calin, G. A. et al. 2005. N. Engl. J. Med. 353:1793-801
Chan, J. A. et al. 2005. Cancer Res. 65:6029-33.
Chen, C. Z., et al. 2004. Science 303: 83-86.
Chen, J. F., et al. 2005. Nat Genet. December 25, advance online publication.
Eis, P. S. et al. 2005. Proc Natl Acad Sci USA. 102: 3627-32.
Giraldez, A. J. et al. 2005. Science 308: 833-838.
Griffiths-Jones, S. et al. 2004. Nucleic Acids Res. 32: D109-D111.
Griffiths-Jones, S., et al. 2006. Nucleic Acids Res. 34: D140-4
He, L. et al. 2005. Nature 435: 828-833.
Hornstein, E. et al. 2005. Nature 438: 671-4.
Hutvagner, G. et al 2001. Science 293: 834-838.
Hutvágner, G. et al. 2004. PLoS Biology 2: 1-11.
Iorio, M. V. et al. 2005. Cancer Res. 65: 7065-70.
Jin, P. et al. 2004. Nat Cell Biol. 6: 1048-53.
Johnson, S. M. et al. 2005. Cell 120: 635-647.
Jopling, C. L. et al. 2005. Science 309:1577-81.
Ketting, R. F. et al. 2001. Genes Dev. 15: 2654-2659.
Kwon, C. et al. 2005. Proc Natl Acad Sci USA. 102: 18986-91.
Landthaler, M. et al. 2004. Curr. Biol. 14: 2162-2167.
Leaman, D. et al. 2005. Cell 121: 1097-108.
Lee, Y., et al. 2003. Nature 425: 415-419.
Li, X. and Carthew, R. W. 2005. Cell 123: 1267-77.
Lu. J. et al. 2005. Nature 435: 834-838.
Michael, M. Z. et al. 2003. Mol. Cancer Res. 1: 882-891.
Nelson, P. et al. 2003. TIBS 28: 534-540.
Paushkin, S., et al. 2002. Curr. Opin. Cell Biol. 14: 305-312.
Poy, M. N. et al. 2004. Nature 432: 226-230.
Wienholds, E. et al. 2005. Science 309: 310-311.
Yekta, S. et al. 2004. Science 304: 594-596.
Zhao, Y. et al. 2005. Nature 436: 214-220.

The invention claimed is:

1. An oligonucleotide with a length of 15 or 16 nucleobase units for inhibition of microRNA-155, wherein the oligonucleotide comprises a core nucleobase sequence from positions one to six, two to seven or from positions three to eight, counting from the 3' end of 3'-ttacga-5' (SEQ ID NO: 8), wherein;

(a) at least one nucleobase unit in said sequence have been substituted by its corresponding LNA unit;

(b) the nucleobase sequence of the oligonucleotide is complementary to a human microRNA-155 sequence;

(c) the oligonucleotide does not comprise a region of more than 5 consecutive DNA units;

(d) the oligonucleotide comprises at least one phosphorothioate internucleoside linkage;

(e) the oligonucleotide comprises at least one DNA unit; and, wherein said oligonucleotide can educe the level of microRNA-155.

2. The oligonucleotide according to claim 1, wherein the oligonucleotide has a length of 15 nucleobase units.

3. The oligonucleotide according to claim 1, wherein the oligonucleotide has a length of 16 nucleobase units.

4. The oligonucleotide according to claim 1, wherein at least two DNA units from positions one to six, two to seven, or three to eight of the oligonucleotide, counting from the 3' end, have been substituted by their corresponding LNA units and wherein the LNA units are separated by at least one DNA unit.

5. The oligonucleotide according to claim 1, wherein at least three DNA units from positions one to six, two to seven, or three to eight of the oligonucleotide, counting from the 3' end, have been substituted by their corresponding LNA units and wherein the LNA units are separated by at least one DNA unit.

6. The oligonucleotide according to claim 1, wherein no more than 2 consecutive nucleobase units from positions one to six, two to seven, or three to eight of the oligonucleotide, counting from the 3' end, are DNA units.

7. The oligonucleotide according to claim 1, wherein 2 to 6 nucleobase units from positions one to six, two to seven, or three to eight of the oligonucleotide, counting from the 3' end, are LNA units.

8. The oligonucleotide according to claim 5, wherein the first nucleobase unit of the oligonucleotide, counting from the 3' end, is a nucleotide analogue, such as an LNA unit.

9. The oligonucleotide according to claim 5 wherein the oligonucleotide comprises at least one region consisting of at least two consecutive LNA units.

10. The oligonucleotide according to claim 1 wherein the nucleobase motif for the three 5' most nucleobase units of the oligonucleotide is selected from the group consisting of Xxx, xXx, xxX, XXx, XxX, xXX and XXX, wherein "X" denotes a LNA unit, and "x" denotes a DNA unit.

11. The oligonucleotide according to claim 1 wherein the oligonucleotide is essentially incapable of recruiting RNaseH based cleavage of a complementary single stranded RNA molecule.

12. The oligonucleotide according to claim 1 wherein the oligonucleotide is capable of forming a duplex with a complementary single stranded RNA nucleic acid molecule with phosphodiester internucleoside linkages, wherein the duplex has a $T_m$ of at least about 70° C.

13. Toe oligonucleotide according to claim 1, wherein the LNA unit or units are beta D oxy-LNA units.

14. The oligonucleotide according to claim 1, wherein all the internucleoside linkages are phosphorothioate linkages.

15. The oligonucleotide according to claim 1, of a formula selected from the group consisting of:

(SEQ ID NO: 32)
5'-TcAcgATtaGcAtTA-3';

(SEQ ID NO: 33)
5'-TcAcGATtaGCAtTA-3';
and, (SEQ ID NO: 37)
5'-TC$^F$AC$^F$G$^F$ATT$^F$A$^F$GC$^F$AT$^F$TA-3', wherein:

a lowercase letter identifies a DNA unit, an upper case letter without superscript identifies a LNA unit, and a capital letter followed by a superscript $^F$ refers to 2' fluoro DNA units.

16. The oligonucleotide according to claim 15, wherein all, the internucleoside linkages are phosphorothioate linkages.

17. The oligonucleotide according to claim 15, wherein the LNA units are beta-D-oxy LNA units.

18. An oligonucleotide that is selected from the group consisting of $5'-T_s{}^oC_sA_s{}^oc_sg_sA_s{}^oT_s{}^ot_sa_sG_s{}^oc_sA_s{}^ot_sT_s{}^oA^o-3'$;  (SEQ ID NO: 32)
and, $5'-T_s{}^oC_sA_s{}^oc_sG_s{}^oA_s{}^oT_s{}^ot_sa_sG_s{}^{om}C_s{}^oA_s{}^ot_sT_s{}^oA^o-3'$,  (SEQ ID NO:33)

wherein:
a lowercase letter identifies a DNA unit,
an upper case letter identifies a LNA, unit,
$^mC$ identifies a 5-methylcytosine LNA,
subscript $_s$ identifies a phosphorothioate internucleoside linkage,
and the LNA units are beta-D-oxy, as identified by a $^o$ superscript after the LNA units.

19. A composition comprising the oligonucleotide according to claim 1, and pharmaceutically acceptable diluent, carrier or adjuvant, or combinations thereof.

20. A composition comprising the oligonucleotide according to claim 18, and a pharmaceutically acceptable diluent, carrier or adjuvant, or combinations thereof.

21. The oligonucleotide according to claim 1, wherein the oligonucleotide comprises a core nucleobase sequence from positions two to seven.

* * * * *

SEQUENCE LISTING

```
<160> NUMBER OF SEQ ID NOS: 110

<210> SEQ ID NO 1
<211> LENGTH: 23
<212> TYPE: RNA
<213> ORGANISM: Homo sapiens

<400> SEQUENCE: 1
uggaguguga caauggguguu ugu                                          23

<210> SEQ ID NO 2
<211> LENGTH: 23
<212> TYPE: RNA
<213> ORGANISM: Homo sapiens

<400> SEQUENCE: 2
ugugcaaauc caugcaaaac uga                                          23

<210> SEQ ID NO 3
<211> LENGTH: 22
<212> TYPE: RNA
<213> ORGANISM: Homo sapiens

<400> SEQUENCE: 3
```

```
uuaaugcuaa ucgugauagg gg                                              22

<210> SEQ ID NO 4
<211> LENGTH: 22
<212> TYPE: RNA
<213> ORGANISM: Homo sapiens

<400> SEQUENCE: 4
uagcuuauca gacugauguu ga                                              22

<210> SEQ ID NO 5
<211> LENGTH: 22
<212> TYPE: RNA
<213> ORGANISM: Homo sapiens

<400> SEQUENCE: 5
uuuguucguu cggcucgcgu ga                                              22

<210> SEQ ID NO 6
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 6 tttgca                                                                 6

<210> SEQ ID NO 7
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 7 acactc                                                                 6

<210> SEQ ID NO 8
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 8 agcatt                                                                 6

<210> SEQ ID NO 9
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 9 cgaaca                                                                 6

<210> SEQ ID NO 10
<211> LENGTH: 6
<212> TYPE: DNA
<213> ORGANISM: Artificial Sequence
<220> FEATURE:
<223> OTHER INFORMATION: Synthetic oligonucleotide
```

```
<400> SEQUENCE: 10 ataagc                                                                    6

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 20, 21, 22, 23
<223> OTHER INFORMATION: LNA modified nucleotide

<400> SEQUENCE: 11
acaaacacca ttgtcacact cca                                                23

<210> SEQ ID NO 12
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 7, 8, 9, 10, 11,  12, 13, 14
<223> OTHER INFORMATION: LNA modified nucleotide

<400> SEQUENCE: 12
acaaacacca ttgtcacact cca                                                23

<210> SEQ ID NO 13
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 6, 9, 12, 15, 18, 21
<223> OTHER INFORMATION: LNA modified nucleotide

<400> SEQUENCE: 13
acaaacacca ttgtcacact cca                                                23

<210> SEQ ID NO 14
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide

<400> SEQUENCE: 14
ccattgtcac actcc                                                         15

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 5, 6, 7, 10, 11, 12, 14, 15
<223> OTHER INFORMATION: LNA modified nucleotide
```

-continued

```
<400> SEQUENCE: 15
ccattgtcac actcc                                                      15

<210> SEQ ID NO 16
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 7, 8, 9, 10, 12, 13
<223> OTHER INFORMATION: LNA modified nucleotide

<400> SEQUENCE: 16
attgtcacac tcc                                                        13

<210> SEQ ID NO 17
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 5, 6, 7, 8, 10, 11
<223> OTHER INFORMATION: LNA modified nucleotide

<400> SEQUENCE: 17
tgtcacactc c                                                          11

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-OME-RNA units

<400> SEQUENCE: 18
ccattgtcac actcc                                                      15

<210> SEQ ID NO 19
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-fluoro-DNA units

<400> SEQUENCE: 19
ccattgtcac actcc                                                      15

<210> SEQ ID NO 20
```

```
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 20, 21, 22, 23
<223> OTHER INFORMATION: LNA modified nucleotide

<400> SEQUENCE: 20
tcagttttgc atggatttgc aca                                          23

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 7, 8, 9, 10, 11, 12, 13, 14
<223> OTHER INFORMATION: LNA modified nucleotide

<400> SEQUENCE: 21
tcagttttgc atggatttgc aca                                          23

<210> SEQ ID NO 22
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 6, 9, 12, 15, 18, 21
<223> OTHER INFORMATION: LNA modified nucleotide

<400> SEQUENCE: 22
tcagttttgc atggatttgc aca                                          23

<210> SEQ ID NO 23
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide

<400> SEQUENCE: 23
tgcatggatt tgcac                                                   15

<210> SEQ ID NO 24
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 5, 6, 7, 10, 11, 12, 14, 15
<223> OTHER INFORMATION: LNA modified nucleotide

<400> SEQUENCE: 24
tgcatggatt tgcac                                                   15
```

```
<210> SEQ ID NO 25
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 4, 5, 7, 8, 9, 10, 12, 13
<223> OTHER INFORMATION: LNA modified nucleotide

<400> SEQUENCE: 25
catggatttg cac                                                          13

<210> SEQ ID NO 26
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 5, 6, 7, 8 , 10, 11
<223> OTHER INFORMATION: LNA modified nucleotide

<400> SEQUENCE: 26
tggatttgca c                                                            11

<210> SEQ ID NO 27
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-OME-RNA units

<400> SEQUENCE: 27
tgcatggatt tgcac                                                        15

<210> SEQ ID NO 28
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-fluoro DNA units

<400> SEQUENCE: 28
tgcatggatt tgcac                                                        15

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: 1, 2, 3, 4, 19, 20, 21, 22
<223> OTHER INFORMATION: LNA modified nucleotide

<400> SEQUENCE: 29
cccctatcac gattagcatt aa                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 7, 8, 9, 10, 11, 12, 13, 14
<223> OTHER INFORMATION: LNA modified nucleotide

<400> SEQUENCE: 30
cccctatcac gattagcatt aa                                              22

<210> SEQ ID NO 31
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 5, 8, 11, 14, 17, 20
<223> OTHER INFORMATION: LNA modified nucleotide

<400> SEQUENCE: 31
cccctatcac gattagcatt aa                                              22

<210> SEQ ID NO 32
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide

<400> SEQUENCE: 32
tcacgattag catta                                                      15

<210> SEQ ID NO 33
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 5, 6, 7, 10, 11, 12, 14, 15
<223> OTHER INFORMATION: LNA modified nucleotide

<400> SEQUENCE: 33
tcacgattag catta                                                      15

<210> SEQ ID NO 34
<211> LENGTH: 13
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_feature
<222> LOCATION: 1, 2, 3, 4, 5, 7, 8, 9, 10, 12, 13
<223> OTHER INFORMATION: LNA modified nucleotide

<400> SEQUENCE: 34
acgattagca tta                                                              13

<210> SEQ ID NO 35
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 5, 6, 7, 9, 10, 11
<223> OTHER INFORMATION: LNA modified nucleotide

<400> SEQUENCE: 35
gattagcatt a                                                                11

<210> SEQ ID NO 36
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 8, 10, 12, 14, 15
<223> OTHER INFORMATION: LNA modified nucleotide
<220> FEATURE:
<221> NAME/KEY: misc_feature
<222> LOCATION: 2, 4, 5, 9, 11, 13
<223> OTHER INFORMATION: 2-prime-OME RNA units

<400> SEQUENCE: 36
tcacgattag catta                                                            15

<210> SEQ ID NO 37
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-fluoro DNA units

<400> SEQUENCE: 37
tcacgattag catta                                                            15

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 19, 20, 21, 22
<223> OTHER INFORMATION: LNA modified nucleotide

<400> SEQUENCE: 38
```
tcaacatcag tctgataagc ta                                          22

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 7, 8, 9, 10, 11, 12, 13, 14
<223> OTHER INFORMATION: LNA modified nucleotide

<400> SEQUENCE: 39
tcaacatcag tctgataagc ta                                          22

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 6, 9, 12, 15, 18, 19, 21
<223> OTHER INFORMATION: LNA modified nucleotide

<400> SEQUENCE: 40
tcatcatcag tctgataagc tt                                          22

<210> SEQ ID NO 41
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide

<400> SEQUENCE: 41
tcagtctgat aagct                                                  15

<210> SEQ ID NO 42
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 5, 6, 7, 10, 11, 12, 14, 15
<223> OTHER INFORMATION: LNA modified nucleotide

<400> SEQUENCE: 42
tcagtctgat aagct                                                  15

<210> SEQ ID NO 43
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 7, 8, 9, 10, 12, 13
<223> OTHER INFORMATION: LNA modified nucleotide

<400> SEQUENCE: 43
agtctgataa gct            13

<210> SEQ ID NO 44
<211> LENGTH: 11
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 5, 7, 8, 9, 10, 11
<223> OTHER INFORMATION: LNA modified nucleotide

<400> SEQUENCE: 44
tctgataagc t            11

<210> SEQ ID NO 45
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-OME RNA units

<400> SEQUENCE: 45
tcagtctgat aagct            15

<210> SEQ ID NO 46
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-fluoro DNA units

<400> SEQUENCE: 46
tcagtctgat aagct            15

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 19, 20, 21, 22
<223> OTHER INFORMATION: LNA modified nucleotide

<400> SEQUENCE: 47
tctcgcgtgc cgttcgttct tt            22

<210> SEQ ID NO 48
<211> LENGTH: 22
<212> TYPE: DNA

```
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 7, 8, 9, 10, 11, 12, 13, 14
<223> OTHER INFORMATION: LNA modified nucleotide

<400> SEQUENCE: 48
tctcgcgtgc cgttcgttct tt                                    22

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 6, 9, 12, 15, 18, 21
<223> OTHER INFORMATION: LNA modified nucleotide

<400> SEQUENCE: 49
tctcgcgtgc cgttcgttct tt                                    22

<210> SEQ ID NO 50
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide

<400> SEQUENCE: 50
gtgccgttcg ttctt                                            15

<210> SEQ ID NO 51
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 5, 6, 7, 10, 11, 12, 14, 15
<223> OTHER INFORMATION: LNA modified nucleotide

<400> SEQUENCE: 51
gtgccgttcg ttctt                                            15

<210> SEQ ID NO 52
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 5, 7, 9, 10, 11, 12, 13
<223> OTHER INFORMATION: LNA modified nucleotide

<400> SEQUENCE: 52
gccgttcgtt ctt                                              13

<210> SEQ ID NO 53
<211> LENGTH: 11
```

```
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 4, 6, 7, 8, 9, 10, 11
<223> OTHER INFORMATION: LNA modified nucleotide

<400> SEQUENCE: 53
cgttcgttct t                                                          11

<210> SEQ ID NO 54
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-OME RNA units

<400> SEQUENCE: 54
gtgccgttcg ttctt                                                      15

<210> SEQ ID NO 55
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10, 12, 14, 15
<223> OTHER INFORMATION: LNA modified nucleotide
<220> FEATURE:
<221> NAME/KEY: misc_feature
<222> LOCATION: 2, 4, 5, 8, 9, 11, 13
<223> OTHER INFORMATION: 2-prime-fluoro DNA units

<400> SEQUENCE: 55
gtgccgttcg ttctt                                                      15

<210> SEQ ID NO 56
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(16)
<223> OTHER INFORMATION: phosphorothioate linkage
<220> FEATURE:
<221> NAME/KEY: misc_feature
<222> LOCATION: 2, 8, 14
<223> OTHER INFORMATION: LNA modified, 5-prime methylated cytosine
<220> FEATURE:
<221> NAME/KEY: misc_feature
<222> LOCATION: 5, 11
<223> OTHER INFORMATION: LNA modified nucleotide

<400> SEQUENCE: 56
ccattgtcac actcca                                                     16

<210> SEQ ID NO 57
```

```
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(16)
<223> OTHER INFORMATION: phosphorothioate linkage
<220> FEATURE:
<221> NAME/KEY: misc_feature
<222> LOCATION: 3, 6, 9
<223> OTHER INFORMATION: LNA modified nucleotide
<220> FEATURE:
<221> NAME/KEY: misc_feature
<222> LOCATION: 12, 15
<223> OTHER INFORMATION: LNA modified, 5-prime methylated cytosine

<400> SEQUENCE: 57
ccattgtcac actcca                                                        16

<210> SEQ ID NO 58
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(16)
<223> OTHER INFORMATION: phosphorthioate linkage
<220> FEATURE:
<221> NAME/KEY: misc_feature
<222> LOCATION: 1, 2, 14, 15
<223> OTHER INFORMATION: LNA modified, 5-prime methylated cytosine
<220> FEATURE:
<221> NAME/KEY: misc_feature
<222> LOCATION: 3, 13
<223> OTHER INFORMATION: LNA modified nucleotide

<400> SEQUENCE: 58
ccattgtcac actcca                                                        16

<210> SEQ ID NO 59
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(15)
<223> OTHER INFORMATION: phosphorothioate linkage
<220> FEATURE:
<221> NAME/KEY: misc_feature
<222> LOCATION: 1, 10, 12, 14, 15
<223> OTHER INFORMATION: LNA modified, 5-prime methylated cytosine
<220> FEATURE:
<221> NAME/KEY: misc_feature
<222> LOCATION: 3, 6, 7
<223> OTHER INFORMATION: LNA modified nucleotide

<400> SEQUENCE: 59
ccattgtcac actcc                                                         15

<210> SEQ ID NO 60
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
```

```
<222> LOCATION: (1)...(15)
<223> OTHER INFORMATION: phosphorothioate linkage
<220> FEATURE:
<221> NAME/KEY: misc_feature
<222> LOCATION: 1, 6, 10, 12, 15
<223> OTHER INFORMATION: LNA modified, 5-prime methylated cytosine
<220> FEATURE:
<221> NAME/KEY: misc_feature
<222> LOCATION: 3, 7, 14
<223> OTHER INFORMATION: LNA modified nucleotide, LNA cytosines are
      methylated

<400> SEQUENCE: 60
ccattctgac cctac                                                    15

<210> SEQ ID NO 61
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(16)
<223> OTHER INFORMATION: phosphorothioate linkage
<220> FEATURE:
<221> NAME/KEY: misc_feature
<222> LOCATION: 3, 6, 9, 12
<223> OTHER INFORMATION: LNA modified nucleotide
<220> FEATURE:
<221> NAME/KEY: misc_feature
<222> LOCATION: 15
<223> OTHER INFORMATION: LNA modified, 5-prime methylated cytosine

<400> SEQUENCE: 61
ccattgtctc aatcca                                                   16

<210> SEQ ID NO 62
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)...(13)
<223> OTHER INFORMATION: phosphorothioate linkage
<220> FEATURE:
<221> NAME/KEY: misc_feature
<222> LOCATION: 1, 4, 5
<223> OTHER INFORMATION: LNA modified nucleotide
<220> FEATURE:
<221> NAME/KEY: misc_feature
<222> LOCATION: 8, 10, 12, 13
<223> OTHER INFORMATION: LNA modified, 5-prime methylated cytosine
<220> FEATURE:

<400> SEQUENCE: 62
attgtcacac tcc                                                      13

<210> SEQ ID NO 63
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: Phosphorothioate linkage
<220> FEATURE:
<221> NAME/KEY: misc_feature
<222> LOCATION: 1, 6, 10, 12, 15
```

```
<223> OTHER INFORMATION: LNA modified, 5-prime-methylated cytosine
<220> FEATURE:
<221> NAME/KEY: misc_feature
<222> LOCATION: 3, 7, 14
<223> OTHER INFORMATION: LNA modified nucleotide

<400> SEQUENCE: 63
ccattctgac cctac                                                          15

<210> SEQ ID NO 64
<211> LENGTH: 22
<212> TYPE: RNA
<213> ORGANISM: Homo sapiens

<400> SEQUENCE: 64
uagcuuauca gacugauguu ga                                                  22

<210> SEQ ID NO 65
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 13, 14, 15
<223> OTHER INFORMATION: LNA modified nucleotide

<400> SEQUENCE: 65
tcagtctgat aagcta                                                         16

<210> SEQ ID NO 66
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 3, 13, 14, 15
<223> OTHER INFORMATION: LNA modified nucleotide

<400> SEQUENCE: 66
tccgtcttag aagata                                                         16

<210> SEQ ID NO 67
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10  12, 14, 15
<223> OTHER INFORMATION: LNA modified nucleotide

<400> SEQUENCE: 67
tctgtcagat acgat                                                          15

<210> SEQ ID NO 68
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 6, 7, 10  12, 14, 15
<223> OTHER INFORMATION: LNA modified nucleotide
```

```
<400> SEQUENCE: 68
tcagtctgat aagct                                                    15

<210> SEQ ID NO 69
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 3, 4, 6, 7, 8, 10  12, 14, 15
<223> OTHER INFORMATION: LNA modified nucleotide

<400> SEQUENCE: 69
tcagtctgat aagct                                                    15

<210> SEQ ID NO 70
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 70 atttgca                                                              7

<210> SEQ ID NO 71
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 71 gatttgca                                                             8

<210> SEQ ID NO 72
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 72 ggatttgca                                                            9

<210> SEQ ID NO 73
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 73 cacactc                                                              7

<210> SEQ ID NO 74
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 74
```

```
tcacactc                                                        8

<210> SEQ ID NO 75
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 75 gtcacactc                                                       9

<210> SEQ ID NO 76
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 76 tagcatt                                                         7

<210> SEQ ID NO 77
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 77 ttagcatt                                                        8

<210> SEQ ID NO 78
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 78 attagcatt                                                       9

<210> SEQ ID NO 79
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 79 acgaaca                                                         7

<210> SEQ ID NO 80
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 80 aacgaaca                                                        8

<210> SEQ ID NO 81
<211> LENGTH: 9
<212> TYPE: DNA
<213> ORGANISM: Artificial Sequence
```

```
<220> FEATURE:
<223> OTHER INFORMATION: Synthetic oligonucleotide

<400> SEQUENCE: 81 gaacgaaca                                                                      9

<210> SEQ ID NO 82
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 15
<223> OTHER INFORMATION: LNA modified, 5-prime methylated cytosine
<220> FEATURE:
<221> NAME/KEY: misc_feature
<222> LOCATION: 6, 9, 12
<223> OTHER INFORMATION: LNA modified nucleotide

<400> SEQUENCE: 82
tgcatggatt tgcaca                                                             16

<210> SEQ ID NO 83
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 15
<223> OTHER INFORMATION: LNA modified, 5-prime metylated cytosine
<220> FEATURE:
<221> NAME/KEY: misc_feature
<222> LOCATION: 6, 9, 12
<223> OTHER INFORMATION: LNA modified nucleotide

<400> SEQUENCE: 83
tgcatggatt tgcac                                                              15

<210> SEQ ID NO 84
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 13
<223> OTHER INFORMATION: LNA modified, 5-prime methylated cytosine
<220> FEATURE:
<221> NAME/KEY: misc_feature
<222> LOCATION: 4, 7, 10
<223> OTHER INFORMATION: LNA modified nucleotide

<400> SEQUENCE: 84
catggatttg cac                                                                13

<210> SEQ ID NO 85
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 4, 6, 8, 10, 12, 14
<223> OTHER INFORMATION: LNA modified nucleotide
```

```
<400> SEQUENCE: 85
tgcatggatt tgcac                                                   15

<210> SEQ ID NO 86
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 4, 6, 8, 10, 12
<223> OTHER INFORMATION: LNA modified nucleotide

<400> SEQUENCE: 86
catggatttg cac                                                     13

<210> SEQ ID NO 87
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 13
<223> OTHER INFORMATION: LNA modified, 5-prime methylated cytosine
<220> FEATURE:
<221> NAME/KEY: misc_feature
<222> LOCATION: 4, 5, 8, 10, 12
<223> OTHER INFORMATION: LNA modified nucleotide

<400> SEQUENCE: 87
catggatttg cac                                                     13

<210> SEQ ID NO 88
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 15
<223> OTHER INFORMATION: LNA modified, 5-prime methylated cytosine
<220> FEATURE:
<221> NAME/KEY: misc_feature
<222> LOCATION: 1, 6, 7, 10, 12, 14
<223> OTHER INFORMATION: LNA modified nucleotide

<400> SEQUENCE: 88
tgcatggatt tgcac                                                   15

<210> SEQ ID NO 89
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 15
<223> OTHER INFORMATION: LNA modified, 5-prime methylated cytosine
<220> FEATURE:
<221> NAME/KEY: misc_feature
<222> LOCATION: 1, 5, 7, 9, 10, 12, 14
<223> OTHER INFORMATION: LNA modified nucleotide

<400> SEQUENCE: 89
tgcatggatt tgcaca                                                  16
```

```
<210> SEQ ID NO 90
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 8
<223> OTHER INFORMATION: LNA modified 5-prime metylated cytosine
<220> FEATURE:
<221> NAME/KEY: misc_feature
<222> LOCATION: 5, 11
<223> OTHER INFORMATION: LNA modified nucleotide

<400> SEQUENCE: 90
ccattgtcac actcca                                                   16

<210> SEQ ID NO 91
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 14
<223> OTHER INFORMATION: LNA modified, 5-prime methylated
<220> FEATURE:
<221> NAME/KEY: misc_feature
<222> LOCATION: 5, 8, 11
<223> OTHER INFORMATION: LNA modified nucleotide

<400> SEQUENCE: 91
ccattgtaac tctcca                                                   16

<210> SEQ ID NO 92
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 12, 15
<223> OTHER INFORMATION: LNA modified, 5-prime methylated cytosine
<220> FEATURE:
<221> NAME/KEY: misc_feature
<222> LOCATION: 3, 6, 9
<223> OTHER INFORMATION: LNA modified nucleotide

<400> SEQUENCE: 92
ccattgtcac actcca                                                   16

<210> SEQ ID NO 93
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 8, 14
<223> OTHER INFORMATION: LNA modified, 5-prime methylated cytosine
<220> FEATURE:
<221> NAME/KEY: misc_feature
<222> LOCATION: 5, 11
<223> OTHER INFORMATION: LNA modified nucleotide

<400> SEQUENCE: 93
```
ccattgtcac actcc                                                      15

<210> SEQ ID NO 94
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 6, 12
<223> OTHER INFORMATION: LNA modified, 5-prime methylated cytosine
<220> FEATURE:
<221> NAME/KEY: misc_feature
<222> LOCATION: 3, 9
<223> OTHER INFORMATION: LNA modified nucleotide

<400> SEQUENCE: 94
attgtcacac tcc                                                        13

<210> SEQ ID NO 95
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 12, 15
<223> OTHER INFORMATION: LNA modified, 5-prime methylated cytosine
<220> FEATURE:
<221> NAME/KEY: misc_feature
<222> LOCATION: 3, 6, 9
<223> OTHER INFORMATION: LNA modified nucleotide

<400> SEQUENCE: 95
ccattgtcac actcc                                                      15

<210> SEQ ID NO 96
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 10, 13
<223> OTHER INFORMATION: LNA modified, 5-prime methylated cytosine
<220> FEATURE:
<221> NAME/KEY: misc_feature
<222> LOCATION: 1, 4, 7
<223> OTHER INFORMATION: LNA modified nucleotide

<400> SEQUENCE: 96
attgtcacac tcc                                                        13

<210> SEQ ID NO 97
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 6, 8, 10, 12
<223> OTHER INFORMATION: LNA modified, 5-prime methylated cytosine
<220> FEATURE:
<221> NAME/KEY: misc_feature
<222> LOCATION: 2, 4
<223> OTHER INFORMATION: LNA modified nucleotide

<400> SEQUENCE: 97
attgtcacac tcc                                                      13

<210> SEQ ID NO 98
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 8, 10, 12, 13
<223> OTHER INFORMATION: LNA modified, 5-prime methylated cytosine
<220> FEATURE:
<221> NAME/KEY: misc_feature
<222> LOCATION: 1, 4, 5
<223> OTHER INFORMATION: LNA modified nucleotide

<400> SEQUENCE: 98
attgtcacac tcc                                                      13

<210> SEQ ID NO 99
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 10, 12, 14, 15
<223> OTHER INFORMATION: LNA modified, 5-prime methylated cytosine
<220> FEATURE:
<221> NAME/KEY: misc_feature
<222> LOCATION: 3, 6, 7
<223> OTHER INFORMATION: LNA modified nucleotide

<400> SEQUENCE: 99
ccattgtcac actcc                                                    15

<210> SEQ ID NO 100
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 15
<223> OTHER INFORMATION: LNA modified, 5-prime methylated cytosine
<220> FEATURE:
<221> NAME/KEY: misc_feature
<222> LOCATION: 4, 7, 11
<223> OTHER INFORMATION: LNA modified nucleotide

<400> SEQUENCE: 100
ccattgtcac actcca                                                   16

<210> SEQ ID NO 101
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 14, 15
<223> OTHER INFORMATION: LNA modified, 5-prime methylated cytosine
<220> FEATURE:
<221> NAME/KEY: misc_feature
<222> LOCATION: 3, 13
<223> OTHER INFORMATION: LNA modified nucleotide

```
<400> SEQUENCE: 101
ccattgtcac actcca                                               16

<210> SEQ ID NO 102
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 2, 11
<223> OTHER INFORMATION: LNA modified, 5-prime methylated cytosine
<220> FEATURE:
<221> NAME/KEY: misc_feature
<222> LOCATION: 5, 8, 14
<223> OTHER INFORMATION: LNA modified nucleotide

<400> SEQUENCE: 102
tcacgattag cattaa                                               16

<210> SEQ ID NO 103
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 5
<223> OTHER INFORMATION: LNA modified, 5-prime methylated cytosine
<220> FEATURE:
<221> NAME/KEY: misc_feature
<222> LOCATION: 2, 8, 11, 14
<223> OTHER INFORMATION: LNA modified nucleotide

<400> SEQUENCE: 103
atcacgatta gcatta                                               16

<210> SEQ ID NO 104
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 11
<223> OTHER INFORMATION: LNA modified, 5-prime methylated cytosine
<220> FEATURE:
<221> NAME/KEY: misc_feature
<222> LOCATION: 1, 3, 5, 7, 9, 13, 15
<223> OTHER INFORMATION: LNA modified nucleotide

<400> SEQUENCE: 104
tcacgattag cattaa                                               16

<210> SEQ ID NO 105
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 12
<223> OTHER INFORMATION: LNA modified, 5-prime methylated cytosine
<220> FEATURE:
<221> NAME/KEY: misc_feature
<222> LOCATION: 1, 4, 6, 8, 10, 14
<223> OTHER INFORMATION: LNA modified nucleotide
```

<400> SEQUENCE: 105
atcacgatta gcatta                                                       16

<210> SEQ ID NO 106
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 5
<223> OTHER INFORMATION: LNA modified, 5-prime methylated cytosine
<220> FEATURE:
<221> NAME/KEY: misc_feature
<222> LOCATION: 2, 8, 11, 14
<223> OTHER INFORMATION: LNA modified nucleotide

<400> SEQUENCE: 106
gagccgaacg aacaa                                                        15

<210> SEQ ID NO 107
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3
<223> OTHER INFORMATION: LNA modified, 5-prime methylated cytosine
<220> FEATURE:
<221> NAME/KEY: misc_feature
<222> LOCATION: 6, 9, 12
<223> OTHER INFORMATION: LNA modified nucleotide

<400> SEQUENCE: 107
gccgaacgaa caa                                                          13

<210> SEQ ID NO 108
<211> LENGTH: 15
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 5, 9, 13
<223> OTHER INFORMATION: LNA modified, 5-prime methylated cytosine
<220> FEATURE:
<221> NAME/KEY: misc_feature
<222> LOCATION: 1, 3, 7, 11, 15
<223> OTHER INFORMATION: LNA modified nucleotide

<400> SEQUENCE: 108
gagccgaacg aacaa                                                        15

<210> SEQ ID NO 109
<211> LENGTH: 13
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 3, 7, 11
<223> OTHER INFORMATION: LNA modified, 5-prime methylated cytosine
<220> FEATURE:
<221> NAME/KEY: misc_feature
<222> LOCATION: 1, 5, 9, 13

```
<223> OTHER INFORMATION: LNA modified nucleotide

<400> SEQUENCE: 109
gccgaacgaa caa                                                              13

<210> SEQ ID NO 110
<211> LENGTH: 15
<212> TYPE: DNA
<213> ORGANISM: Artificial Sequence
<220> FEATURE:
<223> OTHER INFORMATION: Synthetically generated oligonucleotide

<400> SEQUENCE: 110
ccattgtcac actcc                                                            15
```